US012773437B2

(12) United States Patent
Evgin et al.

(10) Patent No.: US 12,773,437 B2
(45) Date of Patent: Oct. 27, 2026

(54) ONCOLYTIC VIRUSES AND METHODS FOR USING ONCOLYTIC VIRUSES

(71) Applicant: Mayo Foundation for Medical Education and Research, Rochester, MN (US)

(72) Inventors: Laura Evgin, Rochester, MN (US); Richard G. Vile, Rochester, MN (US); Amanda L Huff, Rochester, MN (US); Timothy J. Kottke, Oronoco, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1421 days.

(21) Appl. No.: 17/433,784

(22) PCT Filed: Mar. 12, 2020

(86) PCT No.: PCT/US2020/022252
§ 371 (c)(1),
(2) Date: Aug. 25, 2021

(87) PCT Pub. No.: WO2020/190609
PCT Pub. Date: Sep. 24, 2020

(65) Prior Publication Data

US 2022/0143116 A1 May 12, 2022

Related U.S. Application Data

(60) Provisional application No. 62/819,333, filed on Mar. 15, 2019.

(51) Int. Cl.
*A61K 35/768* (2015.01)
*A61K 31/7105* (2006.01)
(Continued)

(52) U.S. Cl.
CPC ........ *A61K 35/768* (2013.01); *A61K 31/7105* (2013.01); *A61K 35/761* (2013.01);
(Continued)

(58) Field of Classification Search
CPC .. A61K 35/768; A61K 35/76; A61K 31/7105; A61K 35/761; A61K 35/763;
(Continued)

(56) References Cited

U.S. PATENT DOCUMENTS

2015/0111836 A1* 4/2015 Kotler ............ C12Y 305/04014 435/6.13
2018/0171029 A1 6/2018 Harris et al.

FOREIGN PATENT DOCUMENTS

WO WO 2014/092647 6/2014
WO WO 2017/004130 1/2017
(Continued)

OTHER PUBLICATIONS

Huff et al. "APOBEC3 Mediates Resistance to Oncolytic Viral Therapy" Molecular Therapy: Oncolytics, vol. 11, Dec. 2018 (Year: 2018).*
(Continued)

*Primary Examiner* — Tracy Vivlemore
*Assistant Examiner* — Lauren K Van Buren
(74) *Attorney, Agent, or Firm* — Fish & Richardson P.C.

(57) ABSTRACT

This document relates to methods and materials for treating cancer. For example, engineered viruses (e.g., oncolytic viruses) encoding one or more inhibitors of apolipoprotein B editing complex 3B (APOBEC3B) polypeptide activity or expression and methods for using such viruses as an oncolytic agent (e.g., to treat cancer) are provided. For example, one or more engineered oncolytic viruses encoding one or
(Continued)

more inhibitors of APOBEC3B polypeptide activity or expression can be administered to a mammal having cancer to treat that mammal.

13 Claims, 32 Drawing Sheets

Specification includes a Sequence Listing.

(51) Int. Cl.
*A61K 35/17* (2025.01)
*A61K 35/761* (2015.01)
*A61K 35/763* (2015.01)
*A61K 38/17* (2006.01)
*A61K 40/11* (2025.01)
*A61K 40/31* (2025.01)
*A61K 40/42* (2025.01)
*A61P 35/00* (2006.01)
*C12N 15/113* (2010.01)
*C12N 15/86* (2006.01)

(52) U.S. Cl.
CPC ........ *A61K 35/763* (2013.01); *A61K 38/1774* (2013.01); *A61K 40/11* (2025.01); *A61K 40/31* (2025.01); *A61K 40/4271* (2025.01); *A61P 35/00* (2018.01); *C12N 15/1135* (2013.01); *C12N 15/86* (2013.01); *A61K 2239/57* (2023.05); *C12N 2310/531* (2013.01); *C12N 2320/31* (2013.01); *C12N 2320/32* (2013.01); *C12N 2760/20232* (2013.01); *C12N 2760/20243* (2013.01)

(58) Field of Classification Search
CPC .... A61K 38/1774; A61K 40/11; A61K 40/31; A61K 40/4271; A61K 2239/57; A61K 35/766; A61P 35/00; A61P 31/12; A61P 31/14; A61P 31/20; A61P 35/02; A61P 35/04; C12N 15/1135; C12N 15/86; C12N 2310/531; C12N 2320/31; C12N 2320/32; C12N 2760/20232; C12N 2760/20243; C12N 2330/51; C12N 2740/13043; C12N 15/113; C12N 15/63; Y02A 50/30
See application file for complete search history.

(56) References Cited

FOREIGN PATENT DOCUMENTS

| | | |
|---|---|---|
| WO | WO 2017/004165 | 1/2017 |
| WO | WO-2017004130 A1 * | 1/2017 |
| WO | WO 2018/064208 | 4/2018 |

OTHER PUBLICATIONS

Renner et al. "Replicating Retroviral Vectors for Gene Therapy of Solid Tumors" Section 3.3.3. RNA Interference Section from the Edited Volume "Novel Gene Therapy Approaches" Published Feb. 13, 2013. (Year: 2013).*
Extended Search Report in European Appln. No. 20773898.0, dated Dec. 7, 2022, 6 pages.
Adli, "The CRISPR tool kit for genome editing and beyond," Nat. Communications, May 15, 2018, 9(1):1911.
Benci et al., "Tumor Interferon Signaling Regulates a Multigenic Resistance Program to Immune Checkpoint Blockade," Cell, Dec. 1, 2016, 167(6):1540-1554.e12.
Bezu et al., "Combinatorial strategies for the induction of immunogenic cell death," Front. Immunology, Apr. 24, 2015, 6:187, 11 pages.
Blackham et al., "Variation in susceptibility of human malignant melanomas to oncolytic vesicular stomatitis virus," Surgery, Mar. 2013, 153(3):333-343.
Boichard et al., "High expression of PD-1 ligands is associated with kataegis mutational signature and APOBEC3 alterations," Oncoimmunology, Mar. 15, 2017, 6(3):e1284719, 11 pages.
Boisgerault et al., "Functional cloning of recurrence-specific antigens identifies molecular targets to treat tumor relapse," Mol. Therapy, Aug. 2013, 21(8):1507-1516.
Bonvin et al., "Interferon-inducible expression of APOBEC3 editing enzymes in human hepatocytes and inhibition of hepatitis B virus replication," Hepatology, Jun. 2006, 43(6):1364-1374.
Burns et al., "APOBEC3B is an enzymatic source of mutation in breast cancer," Nature, Feb. 6, 2013, 494(7437):366-370.
Burns et al., "Evidence for APOBEC3B mutagenesis in multiple human cancers," Nat. Genetics, Jul. 14, 2013, 45(9):977-983.
Campbell et al., "New and TALENted Genome Engineering Toolbox," Circ, Research, Aug. 16, 2013, 113(5):571-587.
Carlson et al., "Establishment, maintenance and in vitro and in vivo applications of primary human glioblastoma multiforme (GBM) xenograft models for translational biology studies and drug discovery," Curr. Protoc. Pharmacology, Mar. 2011, Chapter 14(14):Unit14. 16, 23 pages.
Cescon et al., "APOBEC3B expression in breast cancer reflects cellular proliferation, while a deletion polymorphism is associated with immune activation," Proc. Natl. Acad. Sci. USA, Mar. 3, 2015, 112(9):2841-2846.
Chen et al., "The preferred nucleotide contexts of the AID/APOBEC cytidine deaminases have differential effects when mutating retrotransposon and virus sequences compared to host genes, " PLoS Comput. Biology, Mar. 31, 2017, 13(3):e1005471, 32 pages.
Chiocca, "Oncolytic viruses," Nat. Rev. Cancer, Dec. 2002, 2(12):938-950.
Chou et al., "B-Myb Induces APOBEC3B Expression Leading to Somatic Mutation in Multiple Cancers," Sci. Reports, Mar. 9, 2017, 7:44089, 11 pages.
Conticello et al., "Evolution of the AID/APOBEC family of polynucleotide (deoxy)cytidine deaminases," Mol. Biol. Evolution, Feb. 2005, 22(2):367-377.
Corrigan et al., "Talimogene Laherparepvec: An Oncolytic Virus Therapy for Melanoma," Ann. Pharmacotherapy, Mar. 28, 2017, 51(8):675-681.
Escobar-Zarate et al., "Overcoming cancer cell resistance to VSV oncolysis with JAK1/2 inhibitors," Cancer Gene Therapy, Sep. 13, 2013, 20(10):582-589.
Evgin et al., "Suboptimal T-cell Therapy Drives a Tumor Cell Mutator Phenotype That Promotes Escape from First-Line Treatment," Cancer Immunol. Research, Apr. 2, 2019, 7(5):828-840.
Garcia-Diaz et al., "Interferon Receptor Signaling Pathways Regulating PD-L1 and PD-L2 Expression," Cell Reports, May 9, 2017, 19(6):1189-1201.
Harris et al., "Retroviral restriction by APOBEC proteins," Nat. Rev. Immunology, Nov. 2004, 4(11):868-877.
Henderson et al., "APOBEC-mediated cytosine deamination links PIK3CA helical domain mutations to human papillomavirus-driven tumor development," Cell Reports, Jun. 5, 2014, 7(6):1833-1841.
Hogquist et al., "T cell receptor antagonistic peptides induce positive selection," Cell, Jan. 14, 1994, 76(1):17-27.
Holohan et al., "Cancer drug resistance: an evolving paradigm," Nat. Rev. Cancer, Oct. 2013, 13(10):714-726.
Hu et al., "Epstein-Barr Virus Infection of Mammary Epithelial Cells Promotes Malignant Transformation," EBioMedicine, May 21, 2016, 9:148-160.
Huff et al., "APOBEC3 mediates resistance to oncolytic viral therapy," Mol. Ther. Oncolytics, Aug. 29, 2018, 11:1-13.
Thawar et al., "Oncolytic Viruses-Natural and Genetically Engineered Cancer Immunotherapies," Front. Oncology, Sep. 11, 2017, 7:202, 11 pages.

(56) References Cited

OTHER PUBLICATIONS

Kaluza et al., "Adoptive T cell therapy promotes the emergence of genomically altered tumor escape variants," Int. J. Cancer, Aug. 15, 2012, 131(4):844-854.
Kaluza et al., "Adoptive transfer of cytotoxic T lymphocytes targeting two different antigens limits antigen loss and tumor escape," Hum. Gene Therapy, Oct. 2012, 23(10):1054-1064.
Kottke et al., "Detecting and targeting tumor relapse by its resistance to innate effectors at early recurrence," Nat. Medicine, Nov. 17, 2013, 19(12):1625-1631.
Kottke et al., "Subversion of NK Cell and TNF-alpha Immune Surveillance Drives Tumor Recurrence," Cancer Immunol, Research, Nov. 2017, 5(11):1029-1045.
Law et al., "The DNA cytosine deaminase APOBEC3B promotes tamoxifen resistance in ER-positive breast cancer," Sci. Advances, Oct. 7, 2016, 2(10):e1601737, 9 pages.
Lawler et al., "Oncolytic Viruses in Cancer Treatment: A Review," JAMA Oncology, Jun. 1, 2017, 3(6):841-849.
Leonard et al., "APOBEC3G Expression Correlates with T-Cell Infiltration and Improved Clinical Outcomes in High-grade Serous Ovarian Carcinoma," Clin. Cancer Research, Sep. 15, 2016, 22(18):4746-4755.
Leonard et al., "The PKC/NF-kappaB signaling pathway induces APOBEC3B expression in multiple human cancers," Cancer Research, Nov. 2015, 75(21):4538-4547.
Lichty et al., "Going viral with cancer immunotherapy," Nat. Rev. Cancer, Jul. 3, 2014, 14:559-567.
MacMillan et al., "APOBEC3 inhibition of mouse mammary tumor virus infection: the role of cytidine deamination versus inhibition of reverse transcription," J. Virology, May 2013, 87(9):4808-4817.
Maruyama et al., "Classical NF-kappaB pathway is responsible for APOBEC3B expression in cancer cells," Biochem. Biophys. Res. Communications, Sep. 23, 2016, 478(3):1466-1471.
McGranahan et al., "Allele-Specific HLA Loss and Immune Escape in Lung Cancer Evolution," Cell, Oct. 26, 2017, 171(6): 1259-1271. e11.
Mehta et al., "IFN-alpha and lipopolysaccharide upregulate APOBEC3 mRNA through different signaling pathways," J. Immunology, Oct. 15, 2012, 189(8):4088-4103.
Mertz et al., "Risks at the DNA Replication Fork: Effects upon Carcinogenesis and Tumor Heterogeneity," Genes, Jan. 2017, 8(1):46, 21 pages.
Milewska et al., "APOBEC3-mediated restriction of RNA virus replication," Sci. Reports, Apr. 13, 2018, 8(1):5960, 12 pages.
Moerdyk-Schauwecker et al., "Resistance of pancreatic cancer cells to oncolytic vesicular stomatitis virus: role of type I interferon signaling," Virology, Feb. 5, 2013, 436(1):221-234.
Mohanram et al., "IFN-alpha induces APOBEC3G, F, and A in immature dendritic cells and limits HIV-1 spread to CD4+ T cells," J. Immunology, Apr. 1, 2013, 190(7):3346-3353.
Nair et al., "Biochemical and biological studies of mouse APOBEC3," J. Virology, Apr. 2014, 88(7):3850-3860.
Nowarski et al., "Hypermutation by intersegmental transfer of APOBEC3G cytidine deaminase," Nat. Struct. Mol. Biology, 15(10):1059-1066.
Obuchi et al., "Development of recombinant vesicular stomatitis viruses that exploit defects in host defense to augment specific oncolytic activity," J. Virology, Aug. 2003, 77(16):8843-8856.
Olson et al., "APOBEC Enzymes as Targets for Virus and Cancer Therapy," Cell Chem. Biology, Jan. 18, 2018, 25(1):36-49.
Pak et al., "The role of amino-terminal sequences in cellular localization and antiviral activity of APOBEC3B," J. Virology, Sep. 2011, 85(17):8538-8547.
PCT International Preliminary Report on Patentability in International Appln. No. PCT/US2020/022252, dated Sep. 16, 2021, 8 pages.
PCT International Search Report and Written Opinion in International Appln. No. PCT/US2020/022252, dated Jun. 17, 2020, 11 pages.
Pol et al., "Trial Watch: Oncolytic viruses for cancer therapy," Oncoimmunology, Jun. 1, 2014, 3(6):e28694, 13 pages.
Pol et al., "Trial Watch-Oncolytic viruses and cancer therapy," Oncoimmunology, Feb. 26, 2016, 5(2):el117740, 15 pages.
Roberts et al., "An APOBEC cytidine deaminase mutagenesis pattern is widespread in human cancers," Nat. Genetics, Jul. 14, 2013, 45(9):970-976.
Sanchez-Perez et al., "Synergy of adoptive T-cell therapy with intratumoral suicide gene therapy is mediated by host NK cells," Gene Therapy, Apr. 19, 2007, 14(13):998-1009.
Schmid et al., "Evidence for a TCR affinity threshold delimiting maximal CD8 T cell function," J. Immunology, Mar. 29, 2010, 184(9):4936-4946.
Seplyarskiy et al., "APOBEC-induced mutations in human cancers are strongly enriched on the lagging DNA strand during replication," Genome Research, Feb. 2016, 26(2):174-182.
Sharma et al., "APOBEC3A cytidine deaminase induces RNA editing in monocytes and macrophages," Nat. Communications, Apr. 21, 2015, 6:6881, 15 pages.
Sharma et al., "The double-domain cytidine deaminase APOBEC3G is a cellular site-specific RNA editing enzyme," Sci. Reports, Dec. 15, 2016, 6:39100, 12 pages.
Sheehy et al., "Isolation of a human gene that inhibits HIV-1 infection and is suppressed by the viral Vif protein," Nature, Jul. 14, 2002, 418(6898):646-650.
Shi et al., "Structural basis for targeted DNA cytosine deamination and mutagenesis by APOBEC3A and APOBEC3B," Nat. Struct. Mol. Biology, Dec. 19, 2016, 24(2):131-139.
Smid et al., "Breast cancer genome and transcriptome integration implicates specific mutational signatures with immune cell infiltration," Nat. Communications, Sep. 26, 2016, 7:12910, 9 pages.
Stauffer Thompson et al., "Multiple-hit inhibition of infection by defective interfering particles," J. Gen. Virology, Apr. 2009, 90(Pt 4):888-899.
Suspene et al., "Genetic editing of herpes simplex virus 1 and Epstein-Barr herpesvirus genomes by human APOBEC3 cytidine deaminases in culture and in vivo," J. Virology, Jul. 5, 2011, 85(15):7594-7602.
Swanton et al., "APOBEC Enzymes: Mutagenic Fuel for Cancer Evolution and Heterogeneity," Cancer Discovery, Jul. 2015, 5(7):704-712.
Takeda et al., "IFN-gamma is required for cytotoxic T cell-dependent cancer genome immunoediting," Nat. Communications, Feb. 24, 2017, 8:14607, 13 pages.
Vile et al., "Generation of an anti-tumour immune response in a non-immunogenic tumour: HSVtk-killing in vivo stimulates a mononuclear cell infiltrate and a Th1-like profile of intratumoural cytokine expression," Int. J. Cancer, Apr. 10, 1997, 71(2):267-274.
Vile et al., "Systemic gene therapy of murine melanoma using tissue specific expression of the HSVtk gene involves an immune component," Cancer Research, Dec. 1, 1994, 54(23):6228-6234.
Walker et al., "APOBEC family mutational signatures are associated with poor prognosis translocations in multiple myeloma." Nat. Communications, Apr. 23, 2015, 6:6997, 11 pages.
Wang et al., "APOBEC3 deaminases induce hypermutation in human papillomavirus 16 DNA upon beta interferon stimulation," J. Virology, Jan. 2014, 88(2):1308-1317.
Whelan et al., "Efficient recovery of infectious vesicular stomatitis virus entirely from cDNA clones," Proc. Natl. Acad. Sci. USA, Aug. 29, 1995, 92(18):8388-8392.

* cited by examiner

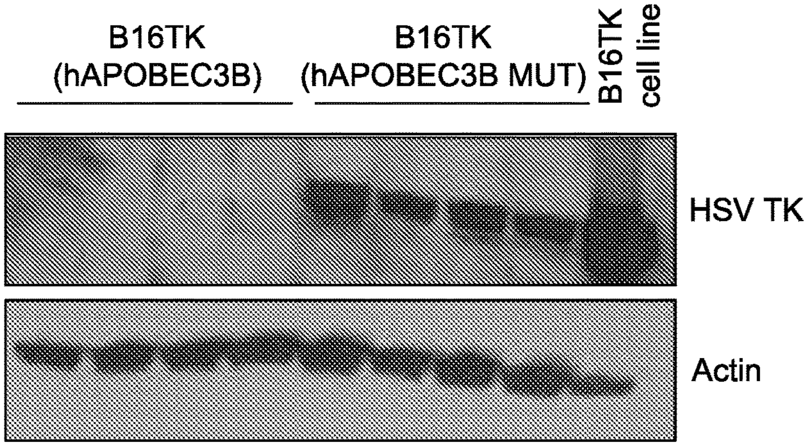

FIG. 20D

| | | | | | | | | | | | |
|---|---|---|---|---|---|---|---|---|---|---|---|
| | | | | | | | | hAPOBEC3B Motif | | | |
| Reference | 1 | | | | | | | | | | 33 |
| HSV-1TK: | ATG | GCT | TCG | TAC | CCC | TGC | CAT | CAA | CAC | GCG | TCT |
| Translation: | Met | A | S | Y | P | C | H | Q | H | A | S |
| B16TK (hAPOBEC3B) | ATG | GCT | TCG | TAC | CCC | TGC | CAT | TAA | CAC | GCG | TCT |
| | ATG | GCT | TCG | TAC | CCC | TGC | CAT | TAA | CAC | GCG | TCT |
| | ATG | GCT | TCG | TAC | CCC | TGC | CAT | TAA | CAC | GCG | TCT |
| | ATG | GCT | TCG | TAC | CCC | TGC | CAT | TAA | CAC | GCG | TCT |
| Translation: | Met | A | S | Y | P | C | H | Stop | H | A | S |
| B16TK (hAPOBEC3B MUT) | ATG | GCT | TCG | TAC | CCC | TGC | CAT | CAA | CAC | GCG | TCT |
| | ATG | GCT | TCG | TAC | CCC | TGC | CAT | CAA | CAC | GCG | TCT |
| | ATG | GCT | TCG | TAC | CCC | TGC | CAT | CAA | CAC | GCG | TCT |
| | ATG | GCT | TCG | TAC | CCC | TGC | CAT | CAA | CAC | GCG | TCT |
| Translation: | Met | A | S | Y | P | C | H | Q | H | A | S |

FIG. 20E

SEQUENCE LISTING

```
<160> NUMBER OF SEQ ID NOS: 17

<210> SEQ ID NO 1
<211> LENGTH: 29
<212> TYPE: DNA
<213> ORGANISM: Artificial
<220> FEATURE:
<223> OTHER INFORMATION: nucleic acid encoding a shRNA molecules that
      can target APOBEC3B

<400> SEQUENCE: 1

gagcagatag taaggttcct ggctacaca                                   29
```

<210> SEQ ID NO 2
<211> LENGTH: 29
<212> TYPE: DNA
<213> ORGANISM: Artificial
<220> FEATURE:
<223> OTHER INFORMATION: nucleic acid encoding a shRNA molecules that
can target APOBEC3B

<400> SEQUENCE: 2
gcagccatcg caaatgctat tcaccgatc 29

<210> SEQ ID NO 3
<211> LENGTH: 29
<212> TYPE: DNA
<213> ORGANISM: Artificial
<220> FEATURE:
<223> OTHER INFORMATION: nucleic acid encoding a shRNA molecules that
can target APOBEC3B

<400> SEQUENCE: 3
aaccaacgag tcaagcatct ctgctacta 29

<210> SEQ ID NO 4
<211> LENGTH: 29
<212> TYPE: DNA
<213> ORGANISM: Artificial
<220> FEATURE:
<223> OTHER INFORMATION: nucleic acid encoding a shRNA molecules that
can target APOBEC3B

<400> SEQUENCE: 4
ggaaaggatt ggagataatc agcaggcgc 29

<210> SEQ ID NO 5
<211> LENGTH: 20
<212> TYPE: DNA
<213> ORGANISM: Artificial
<220> FEATURE:
<223> OTHER INFORMATION: synthetic primer

<400> SEQUENCE: 5
tcatgaccac agtccatgcc 20

<210> SEQ ID NO 6
<211> LENGTH: 20
<212> TYPE: DNA
<213> ORGANISM: Artificial
<220> FEATURE:
<223> OTHER INFORMATION: synthetic primer

<400> SEQUENCE: 6
tcagctctgg gatgaccttg 20

<210> SEQ ID NO 7
<211> LENGTH: 21
<212> TYPE: DNA
<213> ORGANISM: Artificial
<220> FEATURE:
<223> OTHER INFORMATION: synthetic primer

<400> SEQUENCE: 7
atgggaccat tctgtctggg a 21

<210> SEQ ID NO 8
<211> LENGTH: 20

<212> TYPE: DNA
<213> ORGANISM: Artificial
<220> FEATURE:
<223> OTHER INFORMATION: synthetic primer

<400> SEQUENCE: 8
tcaagacacg ggggtccaag 20

<210> SEQ ID NO 9
<211> LENGTH: 8
<212> TYPE: PRT
<213> ORGANISM: Artificial
<220> FEATURE:
<223> OTHER INFORMATION: T cell stimulating peptide

<400> SEQUENCE: 9

Ser Ile Ile Asn Phe Glu Lys Leu
1 5

<210> SEQ ID NO 10
<211> LENGTH: 9
<212> TYPE: PRT
<213> ORGANISM: Artificial
<220> FEATURE:
<223> OTHER INFORMATION: T cell stimulating peptide

<400> SEQUENCE: 10

Lys Val Pro Arg Asn Gln Asp Trp Leu
1 5

<210> SEQ ID NO 11
<211> LENGTH: 20
<212> TYPE: DNA
<213> ORGANISM: Artificial
<220> FEATURE:
<223> OTHER INFORMATION: synthetic primer

<400> SEQUENCE: 11
atgggctcca tcggcgcagc 20

<210> SEQ ID NO 12
<211> LENGTH: 21
<212> TYPE: DNA
<213> ORGANISM: Artificial
<220> FEATURE:
<223> OTHER INFORMATION: synthetic primer

<400> SEQUENCE: 12
ccgtctacac aaaggggaat t 21

<210> SEQ ID NO 13
<211> LENGTH: 24
<212> TYPE: DNA
<213> ORGANISM: Artificial
<220> FEATURE:
<223> OTHER INFORMATION: synthetic primer

<400> SEQUENCE: 13
cacgcagatg cagtcggggc ggcg 24

<210> SEQ ID NO 14
<211> LENGTH: 23
<212> TYPE: DNA
<213> ORGANISM: Artificial
<220> FEATURE:
<223> OTHER INFORMATION: synthetic primer

```
<400> SEQUENCE: 14

ctggtggccc tgggttcgcg cga                                             23


<210> SEQ ID NO 15
<211> LENGTH: 20
<212> TYPE: DNA
<213> ORGANISM: Artificial
<220> FEATURE:
<223> OTHER INFORMATION: synthetic primer

<400> SEQUENCE: 15

gcgttcgtgg ccctcatccc                                                 20


<210> SEQ ID NO 16
<211> LENGTH: 22
<212> TYPE: DNA
<213> ORGANISM: Artificial
<220> FEATURE:
<223> OTHER INFORMATION: synthetic primer

<400> SEQUENCE: 16

gcctgggcct tggacgtctt gg                                              22


<210> SEQ ID NO 17
<211> LENGTH: 21
<212> TYPE: DNA
<213> ORGANISM: Artificial
<220> FEATURE:
<223> OTHER INFORMATION: synthetic primer

<400> SEQUENCE: 17

agggcgcaac gccgtacgtc g                                               21
```

ONCOLYTIC VIRUSES AND METHODS FOR USING ONCOLYTIC VIRUSES

CROSS-REFERENCE TO RELATED APPLICATIONS

This application is a National Stage application under 35 U.S.C. § 371 of International Application No. PCT/US2020/022252, having an International Filing Date of Mar. 12, 2020, which claims priority to U.S. Application Ser. No. 62/819,333, filed Mar. 15, 2019. The disclosure of the prior application is considered part of (and is incorporated by reference in) the disclosure of this application.

SEQUENCE LISTING

The instant application contains a Sequence Listing which has been submitted electronically in ASCII format and is hereby incorporated by reference in its entirety. Said ASCII copy, created on Mar. 11, 2020, is named 07039-1892US1_sequence.txt and is 4 KB bytes in size.

BACKGROUND

1. Technical Field

This document relates to methods and materials for treating cancer. For example, this document provides engineered viruses (e.g., oncolytic viruses) containing nucleic acid encoding one or more inhibitors of apolipoprotein B editing complex 3B (APOBEC3B) polypeptide activity or expression and methods for using such viruses as an oncolytic agent (e.g., to treat cancer). For example, one or more engineered oncolytic viruses encoding one or more inhibitors of APOBEC3B polypeptide activity or expression can be administered to a mammal having cancer to treat that mammal.

2. Background Information

Oncolytic virotherapy has been developed for the treatment of cancer as it combines tumor-tropic cytotoxicity with a highly inflammatory anti-viral response that can activate cellular anti-tumor responses. Strategies such as tropism targeting and arming of the virus with immune stimulatory cytokines to promote the recruitment of immune cells to the tumor have significantly improved the inherent anti-cancer properties of viral therapy (Jhawar et al. *Front Oncol* 7:202 (2017); and Lichty et al., *Nat Rev Cancer* 14:559-567 (2014)). The FDA approval of the Herpes simplex virus (HSV)-based viral therapy Talimogene laherparepvec (Tvec), Imlygic, in 2015 demonstrates the clinical significance of these viral-based platforms (Lawler et al., *JAMA Oncol* 3:841-849 (2017); and Corrigan et al., *Ann Pharmacother* 51:675-681 (2017)). Despite the ability to enhance viral-mediated tumor cell killing and immune activation, clinical responses are observed in only a subset of patients (Pol et al. *Oncoimmunology* 3:e28694 (2014); and Pol et al. *Oncoimmunology* 5:e1117740 (2016)).

SUMMARY

Suboptimal (e.g., incomplete) T cell activation and limited effector function induces APOBEC3B upregulation in targeted tumor cells (e.g., tumor cells directly in contact with T cell activity) and in bystander tumor cells (e.g., tumor cells which are physically separated from the T cells themselves yet are exposed to T cell-derived factors). Upregulation of APOBEC3B in a cell can induce mutations that can provide that cell with a selective advantage to develop immunotherapy (e.g., oncolytic immunotherapy) escape and/or resistance.

This document provides methods and materials for treating cancer. For example, this document provides viral nucleic acid (e.g., viral vectors) as well as viruses (e.g., oncolytic viruses) that encode (e.g., that are engineered to encode) one or more inhibitors of APOBEC3B polypeptide activity or expression. In some cases, viral nucleic acid provided herein and oncolytic viruses provided herein encoding one or more inhibitors of APOBEC3B polypeptide activity or expression can be used as an oncolytic agent (e.g., to treat cancer). For example, one or more oncolytic viruses encoding one or more inhibitors of APOBEC3B polypeptide activity or expression can be administered to a mammal having cancer to treat that mammal.

APOBEC3B is a factor that can restrict the potency of oncolytic viruses (e.g., oncolytic VSVs). For example, VSV infection of cancer cells (e.g., B16 murine melanoma cells) can upregulate APOBEC3B expression in an IFNβ-dependent manner, which is responsible for the evolution of virus-resistant cancer cell populations. As demonstrated herein, in vivo administration of oncolytic virus particles having nucleic acid encoding an inhibitor of APOBEC3B expression or activity (e.g., short hairpin RNA (shRNA) designed to inhibit APOBEC3B expression) to a mammal having cancer can result in an increased level of in vivo oncolytic activity against the cancer cells and/or a reduced level of resistance to the oncolytic therapy by cancer cells within the mammal (as compared to the levels observed using comparable oncolytic virus particles lacking the nucleic acid encoding an inhibitor of APOBEC3B expression or activity).

In some cases, an inhibitor of APOBEC3B polypeptide activity or expression (or nucleic acid constructs or viruses encoding an inhibitor of APOBEC3B polypeptide activity or expression) can be used in combination with immunotherapy (e.g., therapy involving the use of engineered T cells such as chimeric antigen receptor (CAR) T cells) to increase the level of anti-cancer activity against the cancer cells and/or to reduce the level of resistance to the immunotherapy by cancer cells within the mammal (as compared to the levels observed using the immunotherapy without inhibiting APOBEC3B expression or activity). For example, a virus (e.g., an oncolytic virus) encoding an inhibitor of APOBEC3B polypeptide activity or expression can be used in combination with CART cell therapy to treat cancer within a mammal (e.g., a human) in a manner that results in a reduced level of cancer cell resistance to the CAR T cell therapy within the mammal (as compared to the level observed using a comparable virus lacking nucleic acid encoding an inhibitor of APOBEC3B polypeptide activity or expression in combination with the CAR T cell therapy in a comparable mammal).

In general, one aspect of this document features methods for treating a mammal having cancer where the methods can include, or consist essentially of, administering a composition including an oncolytic virus to the mammal, thereby reducing the number of cancer cells within the mammal, where the oncolytic virus can include nucleic acid encoding an inhibitor of APOBEC3B polypeptide activity or expression, and where the level of cancer cell resistance development to the oncolytic virus within the mammal is reduced as compared to the level that develops in a comparable mammal administered a comparable oncolytic virus lacking the nucleic acid encoding the inhibitor. The mammal can be a human. The cancer can be breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, or lymphoma. The oncolytic virus can be a vesicular stomatitis virus (VSV), a Maraba virus (MARAV), a herpes simplex virus (HSV), a vaccinia virus (VV), a measles virus (MV), or a poliovirus (PV). For example, the oncolytic virus can be a VSV. The inhibitor of APOBEC3B polypeptide activity or expression can be a short hairpin RNA (shRNA) that can target nucleic acid encoding the APOBEC3B polypeptide. The nucleic acid encoding the shRNA can include a nucleic acid sequence set forth in SEQ ID NO:1, SEQ ID NO:2, SEQ ID NO:3, or SEQ ID NO:4. The composition can include from about $10^3$ plaque-forming units (PFUs) to about $10^{13}$ PFUs of oncolytic viruses. The composition can include oncolytic viruses at a multiplicity of infection (MOI) of from about 0.0000001 to about 10000.

In another aspect, this document features methods for treating a mammal having cancer where the methods can include, or consist essentially of, administering an oncolytic virus to the mammal, thereby reducing the number of cancer cells within the mammal, and administering nucleic acid or a virus to the mammal, where the nucleic acid or a virus includes nucleic acid encoding an inhibitor of APOBEC3B polypeptide activity or expression, where a reduced level of cancer cell resistance to the oncolytic virus develops within the mammal as compared to the level that develops in a comparable mammal administered the oncolytic virus in the absence of the nucleic acid encoding the inhibitor and in the absence of the virus containing the nucleic acid. The mammal can be a human. The cancer can be breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, or lymphoma. The virus can be a retrovirus, a lentivirus, an adenoviruses, an adeno-associated virus, a VSV, a MARAV, a HSV, a VV, a MV, or a PV. For example, the virus can be a VSV. The oncolytic virus can be a VSV, a HSV, a VV, an AV, a MV, or a PV. For example, the oncolytic virus can be a VSV. The inhibitor of APOBEC3B polypeptide activity or expression can be a shRNA that can target nucleic acid encoding the APOBEC3B polypeptide. The nucleic acid encoding the shRNA can include a nucleic acid sequence set forth in SEQ ID NO:1, SEQ ID NO:2, SEQ ID NO:3, or SEQ ID NO:4. The composition can include from about $10^3$ PFUs to about $10^{13}$ PFUs of oncolytic viruses. The composition can include oncolytic viruses at a MOI of from about 0.0000001 to about 10000.

In another aspect, this document features methods for treating a mammal having cancer where the methods can include, or consist essentially of, administering a composition including a virus to the mammal, thereby reducing the number of cancer cells within the mammal, where the virus can include nucleic acid encoding an inhibitor of APOBEC3B polypeptide activity or expression, and where the level of cancer cell resistance development to an oncolytic virus within the mammal is reduced as compared to the level that develops in a comparable mammal administered a comparable oncolytic virus lacking the nucleic acid encoding the inhibitor. The mammal can be a human. The cancer can be breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, or lymphoma. The virus can be a VSV, a MARAV, a HSV, a VV, a MV, or a PV. The virus can be an oncolytic virus. The virus can be a non-oncolytic virus. The inhibitor of APOBEC3B polypeptide activity or expression can be a shRNA that can target nucleic acid encoding the APOBEC3B polypeptide. The nucleic acid encoding the shRNA can include a nucleic acid sequence set forth in SEQ ID NO:1, SEQ ID NO:2, SEQ ID NO:3, or SEQ ID NO:4. The composition can include from about $10^3$ PFUs to about $10^{13}$ PFUs of oncolytic viruses. The composition can include oncolytic viruses at a MOI of from about 0.0000001 to about 10000.

In another aspect, this document features methods for treating a mammal having cancer where the methods can include, or consist essentially of, administering T cells to the mammal, thereby reducing the number of cancer cells within the mammal, and administering nucleic acid or a virus to the mammal, where the nucleic acid or a virus includes nucleic acid encoding an inhibitor of APOBEC3B polypeptide activity or expression, where a reduced level of cancer cell resistance to the T cells develops within the mammal as compared to the level that develops in a comparable mammal administered the T cells in the absence of the nucleic acid encoding the inhibitor and in the absence of the virus containing said nucleic acid. The mammal can be a human. The cancer can be breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, or lymphoma. The T cells can be CAR T cells. The inhibitor of APOBEC3B polypeptide activity or expression can be a shRNA that can target nucleic acid encoding the APOBEC3B polypeptide. The nucleic acid encoding the shRNA can include a nucleic acid sequence set forth in SEQ ID NO:1, SEQ ID NO:2, SEQ ID NO:3, or SEQ ID NO:4. The composition comprises from about $10^3$ PFUs to about $10^{13}$ PFUs of said oncolytic viruses. The composition can include oncolytic viruses at a MOI of from about 0.0000001 to about 10000.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Figure 1A:
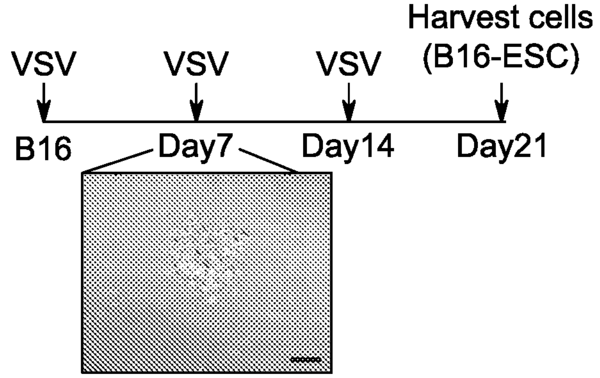
FIG. 1. Generation of VSV-resistant tumor cell populations. (A) Schematic of generation of VSV resistant tumor cell populations. $2\times10^4$ B16 cells were infected at an MOI of 0.01 with VSV-GFP. Wells were washed every 2 days to remove dead cells. 7 days later surviving cells were visible in the wells (A, inset). Bar represents 0.25 mm. On day 7, wells were trypsinized and cells washed 3× in PBS before being re-plated and re-infected at MOI of 0.01 (VSV-GFP). On day 21 after the first infection surviving cells (B16-ESC) were counted (B). (C) Flow cytometry of B16-ESC cells 21 days following initial VSV infection (open histogram) and uninfected parental B16 cells (gray histogram) for GFP expression. Events shown are gate from live cell populations. (D) $2\times10^4$ B16 or B16-ESC were mock infected or infected at an MOI of 0.01 with VSV-GFP. Number of surviving cells was counted 24, 48, 72, and 96 hours post infection. Means±SD of triplicate wells are shown. ns P>0.05; *P≤0.05; P≤0.01; *P≤0.001.

FIG. 2. VSV-resistance is associated with IFN-β-dependent APOBEC3 induction. (A) Levels of IFN-β were measured from supernatants of wells in which $10^5$ B16 cells were either mock infected, or were infected with VSV-GFP at an MOI of 0.01, at 0 (pre-infection), 48 or 96 hours post treatment (Means±SD of triplicate wells are shown). (B) Levels of murine APOBEC3 were measured from lysates of wells in which $10^5$ B16 cells were either mock infected, or were infected with VSV-GFP at an MOI of 0.01, at 0 (pre-infection), 24, 48, 72 or 96 hours post treatment (Means±SD of triplicate wells are shown). (C) Expression of murine APOBEC3 was measured by western blot (upper panel) and qrtPCR (lower panel) from $10^5$ B16 cells infected with VSV-GFP at an MOI of 0.01 at 24 and 48 hours post infection. Levels were normalized to uninfected control. (D) Levels of murine APOBEC3 were measured by ELISA (left panel) and western blot (right panel) from $10^5$ B16 cells infected with VSV-GFP at an MOI of 0.01 at 0 (pre-infection), 48, or 96 hours post treatment either with a control IgG, a polyclonal anti-IFN-β antibody or with AEB071 (10 μM) (Means±SD of triplicate wells are shown). (E) $2\times10^4$ B16 cells were infected at an MOI of 0.01 with VSV-GFP either with a control IgG, a polyclonal anti-IFN-β antibody or with AEB071 (10 μM) (triplicate wells per treatment). Wells were washed every 2 days to remove dead cells. On day 7, wells were trypsinized and cells washed 3× in PBS before being re-plated and re-infected at an MOI of 0.01 (VSV-GFP). This was repeated for one more cycle of 7 day infection. On day 21 after the first infection surviving cells were counted. (F) Expression of APOBEC3 RNA was measured by qrtPCR from $10^5$ B16 or B16-ESC cells. Means±SD of triplicate wells are shown. ns P>0.05; *P≤0.05; P≤0.01; *P≤0.001.

FIG. 3. Knockdown of APOBEC3 reduces the generation of virus-resistant tumor cell populations. (A) $2\times10^4$ B16 cells were infected at an MOI of 0.01 with VSV-GFP or VSV-IFN-β either in the presence, or absence, of AEB071 (10 μM). Wells were washed every 2 days to remove dead cells. 7 days later surviving cells were visualized by crystal violet staining. (B) $2\times10^4$ B16 cells were infected at an MOI of 0.01 with VSV-GFP or VSV-IFN-β in the presence, or absence, of AEB071 (10 μM). Wells were washed every 2 days to remove dead cells. On day 7, wells were trypsinized and cells washed 3× in PBS before being re-plated and re-infected at MOI of 0.01 (VSV-GFP or VSV-IFN-β). This was repeated for one more cycle of 7 day infection. On day 21 after the first infection surviving cells were counted. Means±SD of triplicate wells are shown. (C) Western blot detection of murine APOBEC3 levels in B16 cells transduced with scrambled shRNA, shAPOBEC3 clone 1, shAPOBEC3 clone 2, or left untransduced (D) qrtPCR of APOBEC3 transcripts from parental B16, or B16 transduced with scrambled shRNA or shAPOBEC3 RNA. (E) Levels of murine APOBEC3 were measured from $10^5$ B16 (shAPOBEC3) or B16(scrambled shRNA) cells infected with VSV-GFP or VSV-IFN-β at an MOI of 0.01 at 48 hours post treatment (Means±SD of triplicate wells are shown). (F) $2\times10^4$ B16(shAPOBEC3) or B16(scrambled) cells were infected at an MOI of 0.01 with VSV-GFP or VSV-IFN-β. Wells were washed every 2 days to remove dead cells. On day 7, wells were trypsinized and cells washed 3× in PBS before being re-plated and re-infected at MOI of 0.01 (VSV-GFP or VSV-IFNβ). This was repeated for one more cycle of 7 day infection. On day 21 after the first infection surviving cells were counted. Means±SD of triplicate wells are shown. ns P>0.05; *P≤0.05; P≤0.01; *P≤0.001.

Figure 4:
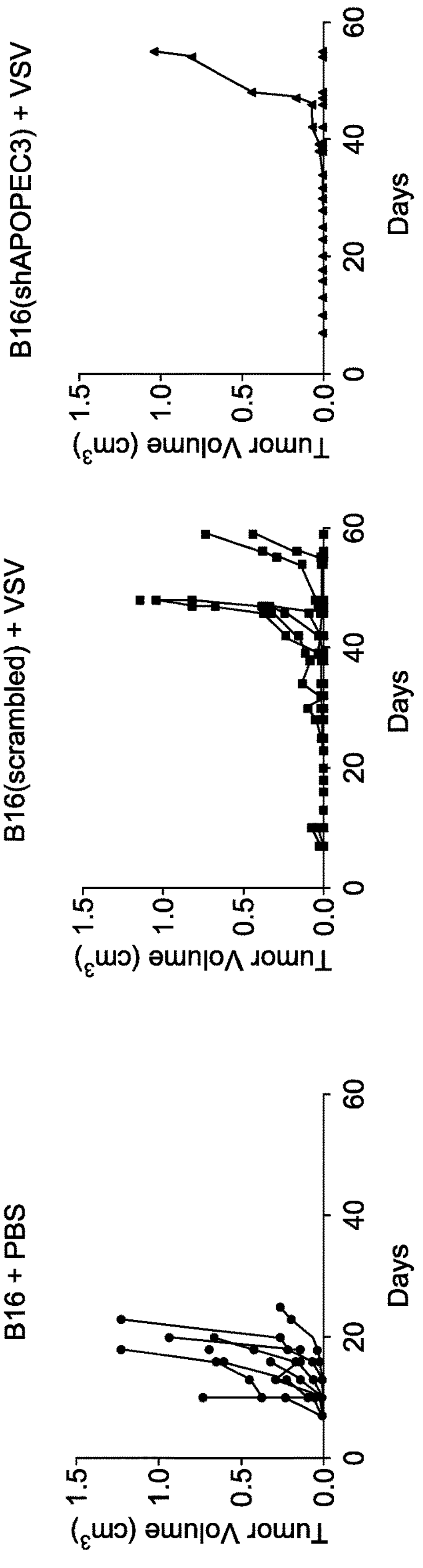

FIG. 4. Knock down of APOBEC3 improves VSV therapy in vivo. C57Bl/6 mice were injected subcutaneously with $2\times10^5$ B16(shAPOBEC3) or B16(scrambled) cells. On days 3, 5, 7, 10, 12, 14, 17, 19, 21, the site of tumor cell injection was injected with PBS or VSV-GFP ($1\times10^8$ pfu). The number of mice with detectable tumors (>0.2 cm diameter) at day 55 is shown. Cumulative results from two separate experiments, n=8 mice per group.

FIG. 5. Knock down of human APOBEC3B improves VSV therapy in human melanomas. (A, left panel) Western blot of hAPOBEC3B expressed in Mel888 cells infected with VSV encoding shRNAs against hAPOBEC3B at an MOT of 0.01; (A, right panel) western blot of hAPOBEC3B expressed in uninfected Mel888 cells or in Mel888 infected with VSV-GFP at an MOT of 0.01, at a shorter exposure than in 5A, left. (B,C) Kaplan Meier survival (B) and tumor volumes (C) of nude mice which were injected subcutaneously with $10^6$ Mel888 cells. On days 3, 5, 7, 10, 12, 14, 17, 19, and 21, tumors were injected with PBS, $10^6$ pfu VSV-GFP, or a combined dose of $10^7$ pfu of VSV-shAPOBEC3 (shRNAs 1-4), n=7 mice per group.

FIG. 6. Overexpression of human APOBEC3B enhances tumor cell escape in vitro. (A) Tumor cell lines were engineered to overexpress human APOBEC3B following infection with either pBABE-Hygro APOBEC3B or pBABE-Hygro APOBEC3B Mut. 48 hours post infection, bulk populations of cells were selected in hygromycin for 2 weeks and used for experiments. (B,C) $10^5$ murine B16 or human Mel888 cells were mock infected (Lane1), or were infected at an MOT of 10 with APOBEC3B MUT (Lane 2) or APOBEC3B (Lane 3) expressing viruses. Expression of hAPOBEC3B was assayed by western blot (B) at 72 hours or 14 days post infection or by qrtPCR at 72 hours post infection (C). (D) $10^4$ B16 parental, B16 APOBEC3B MUT, and B16-APOBEC3B overexpressing cells were plated in triplicate wells per cell line and growth was measured over 96 hours by counting viable cells. Cells were also grown for 96 hours and then trypsinized, viable cells counted, and $10^4$ viable cells were re-plated and grown for a further 96 hours. This regimen was repeated for a total of 20 days in culture. The number of viable cells at the end of the 20 day culture was measured as shown. (21 day time point represents the number of cells of each line grown in the last 96 hr period from an initial plating of $10^4$ viable cells). (E) $2\times10^4$ B16-APOBEC3B or B16-APOBEC3B MUT cells were infected at an MOT of 0.01 with VSV-GFP (triplicate wells per treatment). Wells were washed every 2 days to remove dead cells. On day 7, wells were trypsinized and cells washed 3× in PBS before being re-plated and re-infected at MOT of 0.01 (VSV-GFP). This was repeated for one more cycle of 7 day infection. On day 21 after the first infection surviving cells were counted. $2\times10^4$ GL261-APOBEC3B or GL261-APOBEC3B MUT cells (F), or MEL888-APOBEC3B or MEL888-APOBEC3B MUT cells (G) were infected at an MOI of 0.01 with VSV-GFP (triplicate wells per treatment). Wells were washed every 2 days to remove dead cells. On day 7, wells were trypsinized and cells washed 3× in PBS before being re-plated and re-infected at MOI of 0.01 (VSV-GFP). This was repeated for one more cycle of 7 day infection. On day 21 after the first infection surviving cells were counted. Means±SD of triplicate wells are shown. ns P>0.05; *P≤0.05; P≤0.01; *P≤0.001. (H) Cell survival 120 hours following infection of $10^5$ B16 Parental Cells with no virus, or with pBabe Hygro APOBEC3B or pBabeHygro APBEC3B MUT viruses (MOI ~10) in the presence of polybrene (triplicate wells per infection).

Figure 7A:
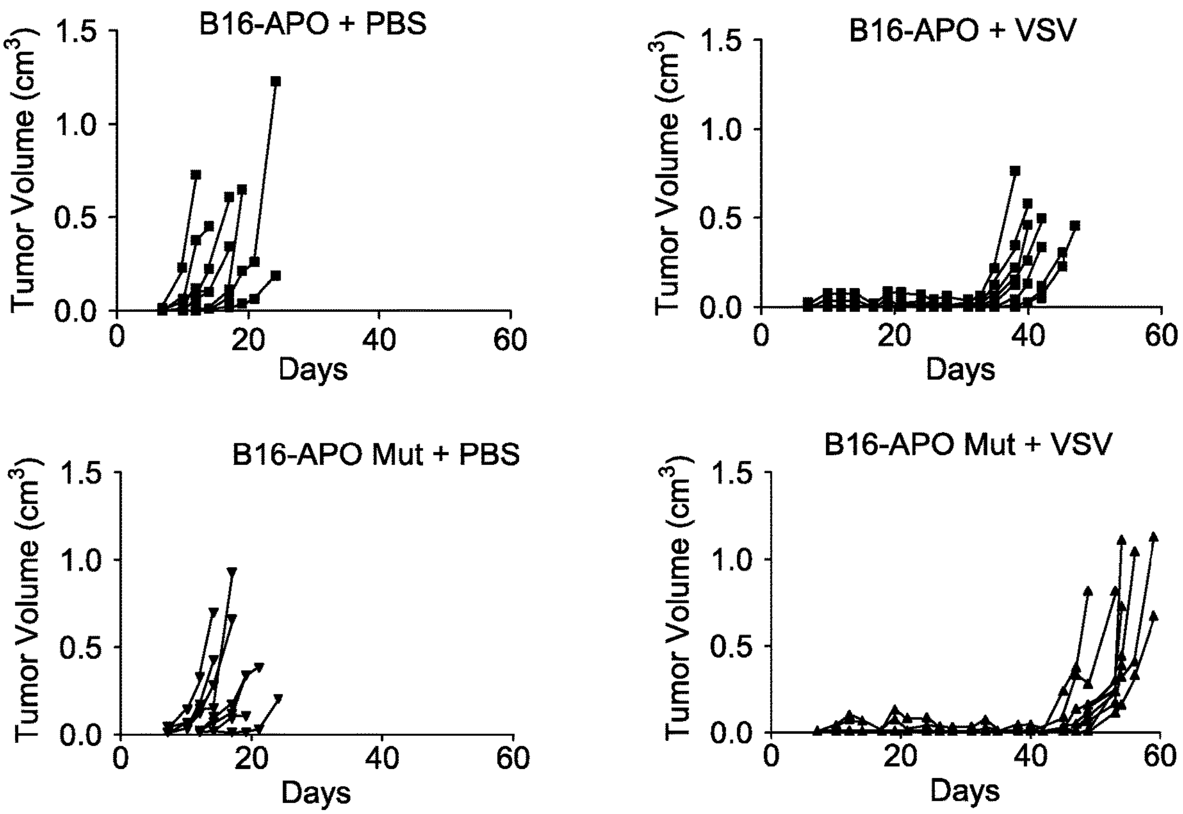
Figure 7B:
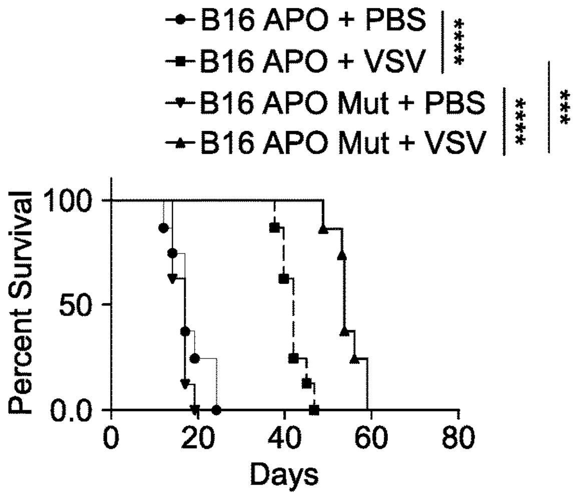

FIG. 7. Overexpression of APOBEC3B decreases the efficacy of VSV therapy in vivo. C57Bl/6 mice were injected subcutaneously with $2\times10^5$ B16(APOBEC3B) or B16 (APOBEC3B-MUT) cells. On days 10, 12, 14, 17, 19, 21, 24, 26, and 28 the site of tumor cell injection was injected with PBS or VSV-GFP ($1\times10^8$ pfu). Tumor growth (A) and overall survival (B) are shown. The number of mice with detectable tumors (>0.2 cm diameter) at day 55 is shown. Cumulative results from two separate experiments, n=8 mice per group. C. Tumors were collected at time of sacrifice and viral titer determined by plaque assay. Means±SD of triplicate wells are shown. ns P>0.05; *P≤0.05; P≤0.01; *P≤0.001.

FIG. 8. APOBEC3B directly affects the fitness of VSV. (A) $2\times10^4$ B16-APOBEC3B or B16-APOBEC3B MUT cells were infected at an MOI of 0.01 with VSV-GFP from a parental stock of titer $5\times10^9$ pfu/ml (triplicate wells per treatment). Wells were washed every 2 days to remove dead cells. On day 7, supernatant was removed and the wells were trypsinized and cells washed 3× in PBS before being re-plated. These re-plated cells were then re-infected with the 7 day virus supernatants for a further 7 days. This was repeated for one more cycle of 7 day infection. On day 21 after the first infection, virus was recovered (VSV-ESC) and titered. Means±SD of triplicate wells are shown. (B) Parental stock VSV-GFP or VSV-ESC viruses were used to infect $10^5$ parental B16 cells at an MOI of 0.01 (as determined from the titers in (A)). 5 days after infection, surviving cells were counted. (C) $1\times10^6$ B16-APOBEC3B MUT or B16-APOBEC3B cells were infected at an MOI of 0.01 for 24 hours. Virus from supernatant was collected and 1 mL of supernatant was used to re-infect a fresh monolayer of $1\times10^6$ B16-APOBEC3B MUT or B16-APOBEC3B cells. Viral supernatants collected from serial passage were diluted from $10^{-1}$-$10^6$ and used to infect $2\times10^4$ BHK cells. The virus was allowed to adsorb for 1 hour at 37° C. and then washed from the well followed by infection with VSV-GFP stock virus at an MOI of 20. Supernatant was collected 24 h post infection and analyzed by plaque assay to determine titer of virus produced. Means±SD of triplicate wells are shown. ns P>0.05; *P≤0.05; P≤0.01; *P≤0.001.

FIG. 9. Tumor experienced CD8 T cells enhance escape from therapy. B16TK cells were treated with 5 μg/mL of ganciclovir (GCV) (A) or reovirus at an MOI of 0.1. (B) Cell viability was measured using Cell titer blue and normalized to untreated cells. (C) Schematic timeline for the generation of escape variants. $10^4$ B16TK cells were plated in the presence of GCV (5 μg/ml) or reovirus (MOI 0.1) for 7 days. Wells were washed with PBS, cultured in medium for 7 days, then treated with GCV or reovirus, respectively, for a further 7 days. (D) B16TK cells treated according to FIG. 9C were counted on day 21. (E) B16TK cells were co-cultured for 72 hours with purified CD8 T cells from untreated C57BL/6 mice (Naïve) or from mice that had previously rejected B16TK tumors following treatment with GCV (Tumor Experienced; T.E.) at an E:T ratio of 10:1. Surviving tumor cells counted (left y-axis). IFNγ in the supernatant was measured by ELISA (right y-axis). (F) B16TK cells were cultured according to FIG. 9C either with no added T cells, or with purified naïve or T.E. CD8 T cells at an E:T ratio of 10:1. Surviving tumor cells were counted at the end of the 21 day culture period. Mean±SD of triplicate wells per treatment is shown for all panels. ns P>0.05; *P≤0.05; P≤0.01; *P≤0.001.

Figure 10B:
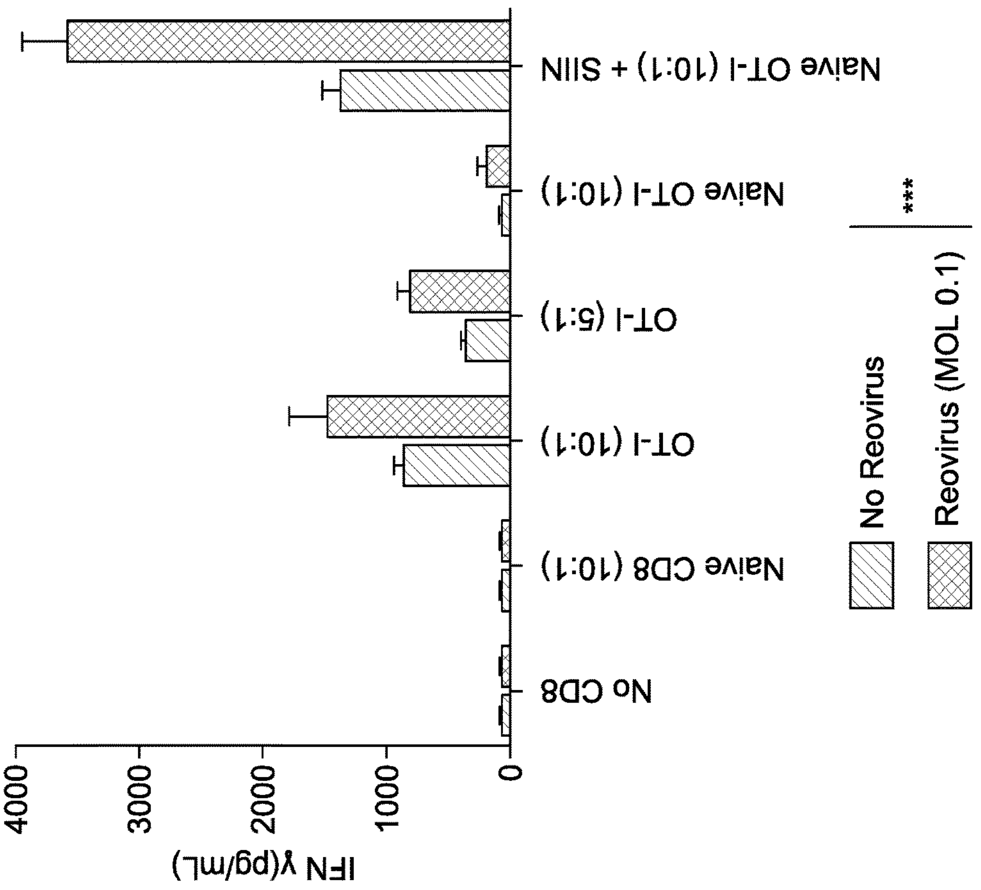

FIG. 10. (A) $10^4$ B 16 cells (not expressing the HSV TK gene and therefore not sensitive to GCV) were co-cultured for 72 hours with purified CD8 T cells from untreated C57Bl/6 mice (Naïve) or from mice that had previously rejected B 16TK tumors following treatment with GCV (Tumor Experienced; T. E.) at an effector to target ratio of 10:1. At the end of the 72 hour co-culture, cells were washed three times to remove T cells and surviving tumor cells counted (left y-axis). IFNγ in the supernatant was measured by ELISA (right y-axis). (B) $10^4$ B 16OVA cells were plated in triplicate wells for 12 hours, with or without reovirus at an MOI of 0.1, in the presence of no added CD8 T cells, CD8 T cells from naïve C57BU6 mice (effector to target ratio of 10:1), 4 day in vitro activated OT-I CD8 T cells at effector to target (E:T) ratios of 10:1 or 5:1, naïve OT-I CD8 T cells, or with naïve OT-I CD8 T cells in the presence of SIINFEKL peptide (SEQ ID NO:9) at 5 μg/ml. The concentration of IFNγ was measured in the supernatants by ELISA. Means±SD of triplicate wells are shown. ns P>0.05; *p≤0.05; p≤0.01; *p≤0.001.

Figure 11:
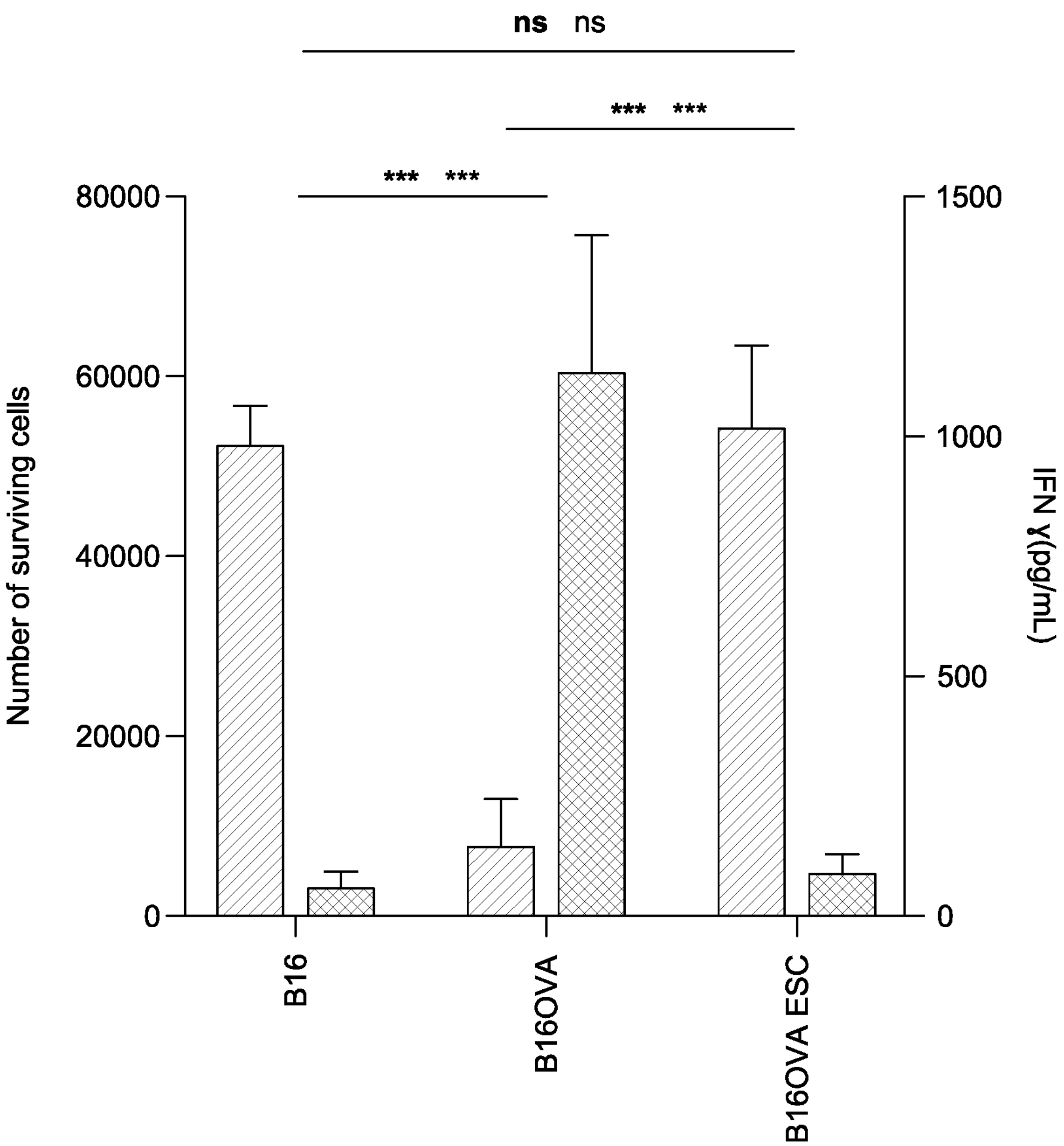

FIG. 11. $10^4$ B16, B16ova or B16ova ESC (B16ova cells grown for 21 days with OT-I T cells at an E:T ratio of 1:1), pre-treated with IFNγ for 24 hours, cells were co-cultured with 4 day activated OT-I T cells for 72 hours in triplicate wells at an E:T ratio of 10:1. Supernatants were harvested for IFNγ by ELISA. Cultures were washed with PBS three times to remove T cells, trypsinized and surviving cells were counted. Means±SD of triplicate wells are shown. ns P>0.05; *p≤0.05; p≤0.01; *p≤0.001.

Figure 12A:
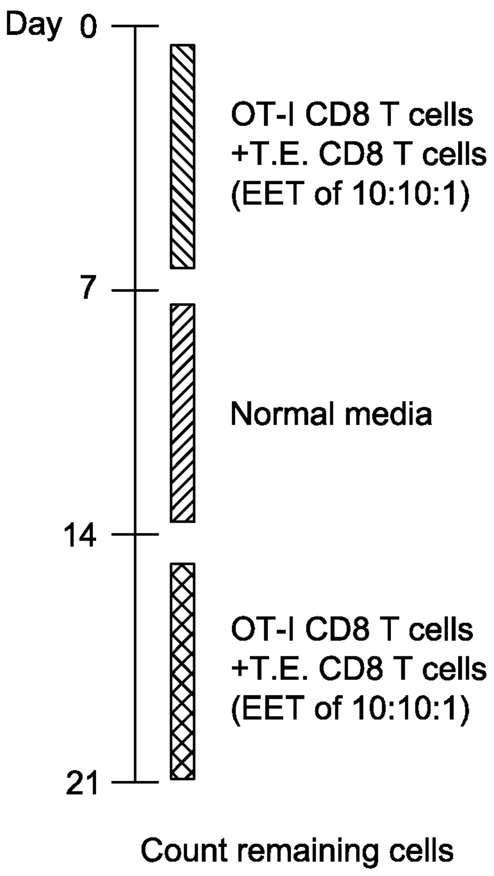

FIG. 12. The T cell mutator phenotype is associated with C to T mutation. (A) Timeline for the generation of B16OVA escape variants. B16OVA cells were plated in the presence of in vitro activated OT-I CD8 T cells and purified T.E. CD8 T cells at an effector to effector to target (E:E:T) ratio of 10:10:1 for 7 days. Wells were washed 3 times with PBS and cultured in normal medium for a further 5 days. Surviving cells were then cultured again in the presence of 4-day in vitro activated OT-I CD8 T cells and T.E. CD8 T cells (E:E:T ratio 10:10:1) for 7 days. (B) The ovalbumin gene was sequenced from discrete colonies of surviving cells on day 21 following treatment from FIG. 12A.

FIG. 13. Incomplete T cell killing of targets promotes mAPOBEC3 activation in bystander tumor cells. (A) B16TK cells were plated in the presence of no T cells, with CD8 T cells from naïve mice at an effector to target ratio of 10:1, in vitro activated OT-I CD8 T cells at an effector to target ratio of 1:1, with CD8 T cells from tumor experienced (T.E.) mice at an effector to target ratio of 10:1, or with PMA at 10 or 25 ng/ml, for 12 hours. mAPOBEC3 expression in tumor cells was assessed by qRT-PCR. mAPOBEC3 expression levels were normalized to GAPDH and presented as fold change relative to untreated cells ±SD. (B) B16OVA cells were plated in the presence of in vitro activated OT-I CD8 T cells at various E:T ratios for 12 hours. (C) B16TK cells were plated in the presence of T.E. CD8 T cells at various E:T ratios for 12 hours. Tumor cells were lysed and the level of mAPOBEC3 was measured by ELISA. Mean±SD of triplicate wells per treatment is shown. (D) Western blot for mAPOBEC3 in cells treated with PMA (25 ng/ml), or naïve or T.E. CD8 T cells, as described in (C) is shown. (E) B16OVA cells were plated in the presence of no added CD8 T cells, naïve CD8 T cells (E:T ratio 10:1), naïve CD8 T cells activated in vitro with α CD3 antibody, in vitro activated OT-I CD8T cells at E:T ratios of 10:1 or 5:1, naïve OT-I CD8 T cells, or with naïve OT-I CD8 T cells in the presence of SIINFEKL (SEQ ID NO:9) peptide at 5 μg/ml. The concentration of IFNγ in the supernatant at 12 hours was measured by ELISA (right y-axis). The levels of APOBEC3 in B16OVA cells were measured by ELISA (left y-axis). (F) B16OVA cells were plated in the presence of 4-day in vitro activated OT-I CD8 T cells at various E:T ratios for 12 hours. TNFα was measured in the supernatant by ELISA. (G) 24 hours following the plating of B16OVA cells in both upper and lower chambers of transwells, 2 day activated OT-I T cells were added to the upper chambers at E:T ratios of 0:1; 10:1; 5;1 or 1:1. (H,I) 24 hours post co-culture medium TNFα was measured by ELISA in the media from both chambers and 72 hours later, both upper and lower chambers were washed three times with PBS and the number of surviving cells in both upper or lower chambers were counted as shown. (J) In separate plates, B16OVA cells recovered from both upper and lower chambers at 12 hours post co-culture with OT-I in the upper chambers were recovered and levels of mAPOBEC3 expression measured by qrtPCR. (K) B16OVA cells transfected 48 hours previously with a plasmid expressing GFP or mAPOBEC3 (~60% transfection efficiency), or B16OVA cells recovered from the lower chambers of the experiment in H above, were co-cultured with 4 day activated OT-I T cells at an E:T ratio of 10:1 in triplicate. The number of surviving cells 48 hours after co-culture is shown. (L) qrtPCR for levels of mAPOBEC3 expression in the B16OVA cells used in K above (transfected 48 hours previously with a plasmid expressing GFP or APOBEC3). Means±SD of triplicate wells are shown. ns P>0.05; *P≤0.05; P≤0.01; *P≤0.001.

FIG. 14. GL2610VA cells (A) or LLCOVA cells (B) were plated in triplicate wells for 12 hours in the presence of no added CD8 T cells, CD8 T cells from naïve C57BL/6 mice (effector to target ratio of 10:1), or 4 day in vitro activated OT-I CD8 T cells at E:T ratios of 10:1 or 1:1 with either control IgG or the anti-TNFα antibody (0.5 μg/mL). The concentration of IFNγ was measured in the supernatants by ELISA (right y-axis). Cells were washed three times in PBS to remove T cells, and the levels of APOBEC3 in tumor cells lysate were measured by ELISA (left y-axis). Means±SD of triplicate wells are shown. ns P>0.05; *p≤0.05; P≤0.01; *P≤0.001.

FIG. 15. mAPOBEC3 is induced by T cells in an MHC class I, PKC and TNFα dependent manner. (A) B16TK cells were co-cultured for 24 hours with GCV and purified naïve or T.E. CD8 T (E:T ratio 10:1) in the presence or absence of the anti-H-2 Kb antibody (AF6-88.5; 0.5 μg/ml), the inhibitor of PKC signaling (AEB071;10 μM) or the anti-TNFα antibody (AF-410-NA; 0.5 μg/ml). Levels of cell associated mAPOBEC3 were measured by ELISA. Means±SD of triplicate wells are shown. (B) B16TK cells were cultured with the GCV, PBS, GCV regimen in FIG. 9C for 21 days either with no added CD8 T cells or with naïve or T.E. CD8 T cells (E:T ratio 10:1). The blocking agents described in panel A were used between days 0-7 and 14-21. Micrographs were taken on day 15. Scale bar=250 μm. (C) Expression of mAPOBEC3 was assessed by western blot in B16TK cells treated with PMA (25 ng/ml) or with purified T.E. CD8 T cells (E:T ratio 10:1) alone or with T.E. CD8 T cells in the presence of the anti-IFNγ antibody (MAB485; 0.5 μg/mL), anti-H-2 Kb antibody AF6-88.5, the inhibitor of PKC signaling AEB071 or the anti-TNFα antibody (AF-410-NA). (D) B16TK cells were grown in the presence of various concentrations of TNFα for 12 hours and the expression of mAPOBEC3 was assessed by western blot. (E) B16TK cells were grown in triplicate well for 24 hours with no added TNFα or with 10 ng/ml TNFα and/or AB071 (10 μM). mAPOBEC3 levels were assessed by ELISA. ns P>0.05; *P≤0.05; P≤0.01; *P≤0.001.

FIG. 16. (A) B16TK cells were co-cultured for 24 hours with purified CD8 T cells from naïve C57BL/6 mice (Naïve) or from mice which had previously rejected B16TK tumors by in vivo treatment with GCV (Tumor-Experienced; T.E.) (E:T ratio of 10:1) in the presence of DMSO (0.001 v/v), the solvent used for AEB071, or the control IgG 0.5 μg/ml. Levels of cell associated murine APOBEC3 were measured by ELISA. Means±SD of triplicate wells are shown. (B) $10^4$ B16TK cells were cultured for 72 hours in the presence or absence of the anti-H-2 Kb antibody (AF6-8S.5; 0.5 μg/ml), the inhibitor of PKG signaling (AEB071; 10 μM) or the antiTNFα antibody (AF-410-NA; 0.5 μg/ml). Surviving cells were counted. Means±SD of triplicate wells are shown. (C) $10^4$ B16 cells (not expressing the HSV TK gene and therefore not sensitive to GCV) were co-cultured for 72 hours with purified CD8 T cells from untreated C57Bl/6 mice (Naïve) or from mice that had previously rejected B16TK tumors following treatment with GCV (Tumor Experienced; T.E.) at an effector to target ratio of 10:1 with or without DMSO or AEB071. At the end of the 72 hour co-culture, cells were washed three times to remove T cells and surviving tumor cells counted (left y-axis). IFNγ in the supernatant was measured by ELISA (right y-axis). Means±SD of triplicate wells are shown. ns P>0.05; *p≤0.05; p≤0.01; *p≤0.001.

FIG. 17. APOBEC3 Mediates T cell-driven mutator activity in tumor cells. (A) B16TK (shRNA mAPOBEC3) cells or B16TK (scrambled shRNA) were cultured for 12 or 48 hours in serum-free medium with, or without, the addition of PMA (25 ng/ml) and APOBEC3 expression was assessed by qRT-PCR. mAPOBEC3 expression levels were normalized to GAPDH and presented as fold change relative to untreated cells±SD. Parental B16TK, B16TK (scrambled shRNA) or B16TK (shRNA mAPOBEC3) were cultured with the GCV regimen (B,D) or the reovirus regimen (C) described in FIG. 9C for 21 days either with no added T cells, or with purified naïve or T.E. CD8 T cells or activated Pmel CD8 T cells at an E:T ratio of 10:1. All wells were washed with PBS to remove T cells and surviving cells were counted at the end of the 21 day culture period. Means±SD of triplicate wells are shown. C57Bl/6 mice were seeded with $2\times10^5$ to B16TK (scrambled shRNA) cells (E) or B16TK (shRNA APOBEC3) cells (F). Mice were treated with GCV (50 mg/kg) on days 5, 6, 7, 8, 9, 12, 13, 14, 15, and 16. Tumor volume over time is shown for each mouse (7 mice/group). (G) B16TK (shRNA mAPOBEC3) cells or B16TK (scrambled shRNA) cells were transfected with the plasmids pCMV-APOBEC3, pCMV-hAPOBEC3B or pCMV-hAPOBEC3B(MUT) (10 μg per $10^5$ cells). 72 hours later transfected cells were trypsinized and re-plated in the presence of GCV (5 μg/ml) for 7 days, washed 3 times in PBS, and then re-cultured in normal medium for a further 7 days. Following washing in PBS, cells were again cultured with GCV for a further 7 days, after which the number of surviving cells was counted as shown. Means±SD of triplicate wells are shown. ns P>0.05; *P≤0.05; * *P≤0.01; ***P≤0.001. (H) Genomic DNA was extracted from surviving tumor cells treated as in panels D and G at both 7 days, and 21 days, following the start of treatment and bulk Sanger sequencing performed on the HSV-TK gene.

FIG. 18. (A) (i) $10^4$ B16TK, B16 (scrambled shRNA) or B16TK (sh mAPOBEC3) cells were plated on day 1 in triplicate wells. Cell numbers were measured at 24 hour intervals. (ii) $10^4$ B16OVA, B16OVA (scrambled shRNA) or B16OVA (shAPOBEC3) cells were plated on day 1 in triplicate wells. On day 4 (96 hours) all the cells in each plate were trypsinized pelleted, wash three times in PBS and re-plated in a T175 flask. 3 days later (day 7) cell numbers were measured. (B) Parental B16OVA, B16OVA (scrambled sh RNA) or B16OVA (sh RNA mAPOBEC3) were cultured with 4 day activated OT-I T cells either with no added T cells, or with purified COB T cells from naïve C57B1/B mice (Naïve) or from mice which had previously rejected B16TK tumors following treatment with GCV (Tumor-Experienced; T.E.) at an effector to target ratio of 10:10:1 for 7 days. All wells were washed with PBS to remove T cells and surviving cell colonies were counted at the end of the culture period. (C) $3\times10^5$ B16OVA sh mAPOBEC3 or B16 scrambled shRNA cells were injected subcutaneously. Mice were sham treated with PBS IT 3 times per week for 3 weeks. Tumor volume was serially monitored. (D) $3\times10^5$ B16APOBEC3B or B16APOBEC3B MUT cells were injected subcutaneously. Mice were sham treated with PBS IT 3 times per week for 3 weeks. Tumor volume was serially monitored.

FIG. 19. (A) B16TK Parental, B16TK (shRNA mAPOBEC3), or B16TK (scrambled shRNA) were transfected with 10 μg of pCMV-APOBEC3 and lysates were harvested 48, 72 or 120 hours post transfection. mAPOBEC3 protein levels in freeze-thawed lysates were quantified by ELISA. (B) B16TK (shRNA mAPOBEC3) cells or B16TK (scrambled shRNA) cells were transfected with the plasmids pCMV-APOBEC3, pCMV-hAPOBEC3B or pCMV-hAPOBEC3B(MUT) (10 μg per $10^5$ cells). 72 hours later transfected cells were trypsinized and re-plated in the presence of GCV (5 μg/ml) for 7 days, washed 3 times in PBS, and then re-cultured in normal medium for a further 7 days. Following washing in PBS, cells were again cultured with GCV for a further 7 days, after which genomic DNA was extracted from surviving tumor cells and bulk Sanger sequencing performed on the HSV-TK gene. (C) Parental B16TK, B16TK (scrambled shRNA) or B16TK (shRNA mAPOBEC3) were cultured with the GCV regimen described in FIG. 9C for 21 days either with no added T cells, or with purified naïve activated Pmel CD8 T cells at an E:T ratio of 10:1. All wells were washed with PBS to remove T cells and surviving cells were counted at the end of the 21 day culture period. Genomic DNA was extracted from surviving tumor cells and bulk Sanger sequencing performed on the HSVTK gene.

FIG. 20. APOBEC3B over-expression drives tumor escape. B16TK cell lines were generated which stably overexpressed either hAPOBEC3B or a catalytically inactive form of hAPOBEC3B (MUT). Parental B16TK cells, B16TK (hAPOBE3B), and B16TK (hAPOBE3B MUT) were cultured with GCV (A) or reovirus (B) according to FIG. 9C. Parental B16TK cells were also co-cultured with purified naïve or T.E. CD8 T cells at an E:T ratio of 10:1. Surviving tumor cells were counted at the end of the 21 day culture period. Means±SD of triplicate wells are shown. ns $P>0.05$; *$P\leq0.05$; $P\leq0.01$; *$P\leq0.001$. (C) Intracranial B16TK, or B16TK (hAPOBEC3B), or B16TK (hAPOBEC3B MUT) tumors were established by injecting $1\times10^4$ cells into the frontal lobe of C57BL/6 mice. Mice were treated with GCV treatment (50 mg/kg) on days 6, 8, 10, 13, 15, 17, 20, 22, and 24 (n=10 mice/group) ***$P\leq0.001$. (D) 4 tumors from each of the B16TK (hAPOBEC3B) and B16TK (hAPOBEC3B MUT) groups were recovered and screened for expression of the HSVTK protein by Western Blot and sequenced (E). (F) Subcutaneous B16TK, or B16TK (hAPOBEC3B), or B16TK (hAPOBEC3B MUT) tumors were established by injecting $2\times10^5$ cells into the flank of C57BL/6 mice. Mice were treated with GCV (50 mg/kg) or PBS on days 6, 8, 10, 13, 15, 17, 20, 22, and 24 (n=10 mice/group). Tumor size over time is shown.

DETAILED DESCRIPTION

This document provides methods and materials for treating cancer. For example, this document provides methods and materials for treating cancer using viral nucleic acid (e.g., viral vectors) and/or viruses (e.g., oncolytic viruses) that encode (e.g., that are engineered to encode) one or more inhibitors of APOBEC3B polypeptide activity or expression. In some cases, this document provides engineered oncolytic viruses that contain nucleic acid encoding one or more inhibitors of APOBEC3B polypeptide activity or expression. For example, an oncolytic virus encoding one or more inhibitors of APOBEC3B polypeptide activity or expression can include nucleic acid encoding shRNA that can target APOBEC3B and inhibit its expression.

In some cases, this document provides methods for using viral nucleic acid (e.g., viral vectors) and/or viruses (e.g., oncolytic viruses) that encode (e.g., that are engineered to encode) one or more inhibitors of APOBEC3B polypeptide activity or expression to treat a mammal having, or at risk of developing, cancer. For example, engineered viral nucleic acid provided herein and/or oncolytic viruses provided herein encoding one or more inhibitors of APOBEC3B polypeptide activity or expression can be administered to a mammal having, or at risk of developing, cancer to reduce the number of cancer cells (e.g., by infecting cancer cells in the mammal and stimulating anti-cancer immune responses in the mammal) in the mammal (e.g., a human). In some cases, one or more viral vectors encoding one or more inhibitors of APOBEC3B polypeptide activity or expression and one or more oncolytic viruses can be administered to a mammal having, or at risk of developing, cancer to reduce the number of cancer cells in the mammal. In some cases, one or more oncolytic viruses encoding one or more inhibitors of APOBEC3B polypeptide activity or expression can be administered to a mammal having, or at risk of developing, cancer to reduce the number of cancer cells in the mammal. In some cases, one or more viruses encoding one or more inhibitors of APOBEC3B polypeptide activity or expression and one or more oncolytic viruses can be administered to a mammal having, or at risk of developing, cancer to reduce the number of cancer cells in the mammal.

Viral nucleic acid (e.g., a viral vector) encoding (e.g., engineered to encode) one or more inhibitors of APOBEC3B polypeptide activity or expression can be any appropriate nucleic acid (e.g., DNA, RNA, or a combination thereof). In some cases, viral nucleic acid encoding one or more inhibitors of APOBEC3B polypeptide activity or expression can be a nucleic acid construct.

A virus (e.g., an oncolytic virus particle) containing nucleic acid encoding (e.g., engineered to encode) one or more inhibitors of APOBEC3B polypeptide activity or expression can be any appropriate virus. For example, a virus having nucleic acid encoding one or more inhibitors of APOBEC3B polypeptide activity or expression as described herein can be an oncolytic virus or a non-oncolytic virus. Examples of types of viruses that can be designed to have nucleic acid encoding one or more inhibitors of APOBEC3B polypeptide activity or expression as described herein include, without limitation, retroviruses, lentiviruses, adenoviruses, adeno-associated viruses, rhabdoviruses (e.g., vesicular stomatitis virus (VSV) and Maraba virus (MARAV)), a herpes simplex virus (HSV), a vaccinia virus (VV), a measles virus (MV), and a poliovirus (PV), and hybrids thereof. Examples of oncolytic viruses that can be designed to encode one or more inhibitors of APOBEC3B polypeptide activity or expression as described herein include, without limitation, VSV, HSV, VV, MV, and PV.

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein can be (or can contain in the case of viruses) double stranded nucleic acid.

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein can be (or can contain in the case of viruses) single stranded nucleic acid.

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein can be replication competent.

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein can be replication defective.

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein can be non-pathogenic (e.g., to a mammal being treated as described herein). For example, a virus particle provided herein containing nucleic acid encoding one or more inhibitors of APOBEC3B polypeptide activity or expression can be genetically modified to render it non-pathogenic to a mammal to be treated.

In some cases, viruses (e.g., oncolytic viruses) provided herein encoding (e.g., engineered to encode) one or more inhibitors of APOBEC3B polypeptide activity or expression described herein can infect dividing cells (e.g., can infect only dividing cells).

In some cases, viruses (e.g., oncolytic viruses) provided herein encoding (e.g., engineered to encode) one or more inhibitors of APOBEC3B polypeptide activity or expression described herein can infect non-dividing cells (e.g., can infect only non-dividing cells).

In some cases, viral nucleic acid (e.g., viral vectors) provided herein and viruses (e.g., oncolytic viruses) provided herein encoding (e.g., engineered to encode) one or more inhibitors of APOBEC3B polypeptide activity or expression described herein are not destroyed a mammal's immune system. For example, viral nucleic acid provided herein and viruses provided herein encoding one or more inhibitors of APOBEC3B polypeptide activity or expression described herein are not destroyed by antigen presenting cells (APCs), macrophages, and/or other immune cells in a mammal that the viral nucleic acid provided herein and/or the viruses provided herein encoding one or more inhibitors of APOBEC3B polypeptide activity or expression are administered to.

Viral nucleic acid (e.g., viral vectors) provided herein and viruses (e.g., oncolytic viruses) provided herein encoding (e.g., engineered to encode) one or more inhibitors of APOBEC3B polypeptide activity or expression can encode any appropriate inhibitor(s) of APOBEC3B polypeptide activity or expression. An inhibitor of an APOBEC3B polypeptide activity or expression can be any molecule that inhibits (e.g., reduces or eliminates) APOBEC3B polypeptide activity or expression. An inhibitor of an APOBEC3B polypeptide activity or expression can be any appropriate type of molecule (e.g., nucleic acids such as siRNA molecules, shRNA molecules, antisense molecules, targeting guide RNA molecules of a clustered regularly interspaced short palindromic repeats (CRISPR)/Cas9 system, miRNAs (e.g., natural miRNA and artificial miRNA); and polypeptides such as antibodies and transcription activator-like effector nucleases (TALENs)).

In some cases, RNA interference can be used reduce or eliminate APOBEC3B polypeptide activity or expression. For example, nucleic acid molecules designed to induce RNA interference of APOBEC3B (e.g., a siRNA molecule or a shRNA molecule) can be used as described herein to reduce or eliminate APOBEC3B polypeptide expression. Examples of nucleic acid molecules that can be used as described herein to reduce or eliminate APOBEC3B polypeptide expression include, without limitation, nucleic acid sequences encoding shRNA molecules that can target nucleic acid encoding an APOBEC3B polypeptide. Exemplary shRNA molecules that can target nucleic acid encoding an APOBEC3B polypeptide include, without limitation, those sequences set forth Table 1.

TABLE 1

Examples of sequences that can encode shRNA molecules that can target nucleic acid encoding an APOBEC3B polypeptide.

| Sequence encoding shRNA | SEQ ID NO: |
|---|---|
| GAGCAGATAGTAAGGTTCCTGGCTACACA | 1 |
| GCAGCCATCGCAAATGCTATTCACCGATC | 2 |
| AACCAACGAGTCAAGCATCTCTGCTACTA | 3 |
| GGAAAGGATTGGAGATAATCAGCAGGCGC | 4 |

In some cases, a CRISPR/Cas9 system can be used as described herein to reduce or eliminate APOBEC3B polypeptide activity or expression. For example, guide RNA molecules of a CRISPR-Cas9 system can be designed to target nucleic acid encoding an APOBEC3B polypeptide such that the Cas9 of the CRISPR/Cas9 system can cleave the nucleic acid that encodes an APOBEC3B polypeptide to reduce or eliminate APOBEC3B polypeptide activity or expression. The CRISPR/Cas9 system can be as described elsewhere (Adli, *Nat Commun.* 9(1):1911 (2018)).

In some cases, one or more TALENs can be used as described herein to reduce or eliminate APOBEC3B polypeptide activity or expression. For example, TALENs can be designed to target nucleic acid encoding an APOBEC3B polypeptide such that the TALENs cleave the nucleic acid encoding an APOBEC3B polypeptide to reduce or eliminate APOBEC3B polypeptide activity or expression. The nucleic acid or polypeptide sequence of such genome editing molecules can be as described elsewhere (Campbell et al., *Circulation Research,* 113:571-587 (2013)).

In some cases, viral nucleic acid (e.g., viral vectors) provided herein and viruses (e.g., oncolytic viruses) provided herein encoding (e.g., engineered to encode) one or more more inhibitors of APOBEC3B polypeptide activity or expression can be as described in Example 1 or Example 2. In some cases, viral nucleic acid provided herein and viruses provided herein encoding one or more inhibitors of APOBEC3B polypeptide activity or expression can be as described elsewhere (see, e.g., Huff et al., *Mol. Ther. Oncolytics,* 11:1-13 (2018)).

This document also provides methods for using viral nucleic acid (e.g., viral vectors) provided herein and viruses (e.g., oncolytic viruses) provided herein encoding (e.g., engineered to encode) one or more inhibitors of APOBEC3B polypeptide activity or expression provided herein. In some cases, viral nucleic acid provided herein and/or viruses provided herein encoding one or more inhibitors of APOBEC3B polypeptide activity or expression can be used to treat a mammal (e.g., a human) having, or at risk of developing, cancer. For example, viral nucleic acid provided herein and/or viruses provided herein encoding one or more inhibitors of APOBEC3B polypeptide activity or expression can be administered to a mammal having, or at risk of developing, cancer to reduce the number of cancer cells (e.g., by infecting and killing cancer cells) in the mammal. For example, viral nucleic acid provided herein and/or viruses provided herein encoding one or more inhibitors of APOBEC3B polypeptide activity or expression can be administered to a mammal having, or at risk of developing, cancer to reduce the size (e.g., the volume) of one or more tumors in the mammal. In some cases, viral nucleic acid provided herein and/or viruses provided herein encoding one or more inhibitors of APOBEC3B polypeptide activity or expression can be administered to a mammal having, or at risk of developing, cancer such that cancer cells within the mammal can develop resistance to an oncolytic virus at a reduced level (e.g., as compared to a level that develops in a comparable mammal administered a comparable oncolytic virus in the absence of any inhibitor of APOBEC3B polypeptide activity or expression). For example, when oncolytic viruses provided herein encoding one or more inhibitors of APOBEC3B polypeptide activity or expression are administered to a mammal having, or at risk of developing, cancer, the level of cancer cell resistance development to the oncolytic virus within the mammal can be reduced (e.g., as compared to a level that develops in a comparable mammal administered a comparable oncolytic virus lacking nucleic acid encoding an inhibitor of APOBEC3B polypeptide activity or expression).

In some cases, methods described herein also can include identifying a mammal as having, or at risk of developing, cancer. Examples of methods for identifying a mammal as having, or at risk of developing, cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests.

Once identified as having, or at risk of developing, cancer, a mammal can be administered or instructed to self-administer viral nucleic acid (e.g., viral vectors) provided herein and/or viruses (e.g., oncolytic viruses) provided herein encoding (e.g., engineered to encode) encoding one or more inhibitors of APOBEC3B polypeptide activity or expression described herein (e.g., one or more oncolytic viruses encoding one or more inhibitors of APOBEC3B polypeptide activity or expression). In some cases, one or more viral vectors encoding one or more inhibitors of APOBEC3B polypeptide activity or expression and one or more oncolytic viruses can be administered to a mammal having, or at risk of developing, cancer to treat the mammal. In some cases, one or more oncolytic viruses and one or more viruses encoding one or more inhibitors of APOBEC3B polypeptide activity or expression can be administered to a mammal having, or at risk of developing, cancer to treat the mammal. In some cases, one or more oncolytic viruses encoding one or more inhibitors of APOBEC3B polypeptide activity or expression can be administered to a mammal having, or at risk of developing, cancer to treat the mammal.

In cases where one or more viral vectors and/or one or more non-oncolytic viruses encoding one or more inhibitors of APOBEC3B polypeptide activity or expression and one or more oncolytic viruses are administered to a mammal having, or at risk of developing, cancer to treat the mammal, the one or more viral vectors and/or one or more non-oncolytic viruses and the one or more oncolytic viruses can be administered at the same time or independently. For example, one or more viral vectors and/or one or more non-oncolytic viruses encoding one or more inhibitors of APOBEC3B polypeptide activity or expression and one or more oncolytic viruses can be administered to a mammal at the same time (e.g., can be formulated together to form a single composition to be administered to a mammal). In some cases, one or more viral vectors and/or one or more non-oncolytic viruses encoding one or more inhibitors of APOBEC3B polypeptide activity or expression can be administered first, and the one or more oncolytic viruses administered second, or vice versa.

In cases where one or more viral vectors and/or one or more non-oncolytic viruses encoding one or more inhibitors of APOBEC3B polypeptide activity or expression and one or more oncolytic viruses are administered to a mammal having, or at risk of developing, cancer to treat the mammal, the one or more viral vectors and/or one or more non-oncolytic viruses and the one or more oncolytic viruses can be administered in any appropriate ratio (e.g., a ratio of one or more viral vectors and/or one or more non-oncolytic viruses encoding one or more inhibitors of APOBEC3B polypeptide activity or expression to one or more oncolytic viruses). For example, one or more viral vectors and/or one or more non-oncolytic viruses encoding one or more inhibitors of APOBEC3B polypeptide activity or expression and one or more oncolytic viruses can be administered to a mammal having, or at risk of developing, cancer at a ratio of from about 0.001:1 to about 100:1.

Any appropriate mammal having, or at risk of developing, cancer can be treated as described herein (e.g., by administering viral nucleic acid such as viral vectors provided herein and/or viruses such as oncolytic viruses encoding one or more inhibitors of APOBEC3B polypeptide activity or expression). For example, humans, non-human primates (e.g., monkeys), horses, bovine species, porcine species, dogs, cats, mice, and rats having, or at risk of developing, cancer can be treated for cancer as described herein. In some cases, a human having cancer can be treated as described herein.

A mammal having any type of cancer can be treated as described herein. In some cases, a cancer can include one or more solid tumors. In some cases, a cancer can be a blood cancer. Examples of cancers that can be treated as described herein include, without limitation, breast cancers (e.g., estrogen receptor positive breast cancer or estrogen receptor negative breast cancer), brain cancers (e.g., glioma), prostate cancers, ovarian cancers, lung cancers, hepatocellular carcinomas, pancreatic cancers, kidney cancers, melanomas, bladder cancers, colorectal cancers, sarcomas (e.g., osteosarcomas), and blood cancers (e.g., myelomas, leukemias, lymphomas).

In some cases, when administering viral nucleic acid (e.g., viral vectors) provided herein and/or viruses (e.g., oncolytic viruses) provided herein encoding (e.g., engineered to encode) one or more inhibitors of APOBEC3B polypeptide activity or expression provided herein to a mammal (e.g., a human) as described herein, the viral nucleic acid and/or viruses encoding one or more inhibitors of APOBEC3B polypeptide activity or expression can stimulate anti-cancer immune responses in the mammal.

In some cases, when administering viral nucleic acid (e.g., viral vectors) provided herein and/or viruses (e.g., oncolytic viruses) provided herein encoding (e.g., engineered to encode) one or more inhibitors of APOBEC3B polypeptide activity or expression provided herein to a mammal (e.g., a human) as described herein, the viral nucleic acid and/or viruses encoding (e.g., engineered to encode) one or more inhibitors of APOBEC3B polypeptide activity or expression can stimulate an optimal T cell activation. For example, administering viral nucleic acid and/or viruses encoding one or more inhibitors of APOBEC3B polypeptide activity or expression provided herein to a mammal as described herein can be effective to stimulate T cell responses in the mammal that are cytotoxic. In some cases, T cell responses in a mammal that are stimulated by administering viral nucleic acid encoding one or more inhibitors of APOBEC3B polypeptide activity or expression to the mammal can be effective to kill greater than about 75% (e.g., 75%, 80%, 85%, 90%, 93%, 95%, 98%, 99%, or 100%) of cancer cells within the mammal. In some cases, less than about 1% (e.g., about 1%, about 0.7%, about 0.5%, about 0.25%, or 0%) of cancer cells within a mammal can escape T cell responses in the mammal (e.g., can escape T cell responses and form one or more recurrent tumors in the mammal) that are stimulated by administering viral nucleic acid provided herein and/or viruses provided herein encoding one or more inhibitors of APOBEC3B polypeptide activity or expression to the mammal.

In some cases, when administering viral nucleic acid (e.g., viral vectors) provided herein and/or viruses (e.g., oncolytic viruses) provided herein encoding (e.g., engineered to encode) one or more inhibitors of APOBEC3B polypeptide activity or expression provided herein to a mammal (e.g., a human) as described herein, the viral nucleic acid and/or viruses encoding (e.g., engineered to encode) one or more inhibitors of APOBEC3B polypeptide activity or expression can be effective to reduce or eliminate APOBEC3B polypeptide activity or expression in infected cells and/or uninfected nearby cells. For example, administering viral nucleic acid and/or viruses encoding one or more inhibitors of APOBEC3B polypeptide activity or expression provided herein to a mammal as described herein can be effective to reduce or eliminate APOBEC3B polypeptide activity or expression in infected cancer cells and to kill those infected cancer cells within the mammal. In some cases, administering viral nucleic acid and/or viruses encoding one or more inhibitors of APOBEC3B polypeptide activity or expression provided herein to a mammal as described herein can be effective to reduce or eliminate APOBEC3B polypeptide activity or expression in infected cancer cells and to kill those infected cancer cells within the mammal, while being effective to reduce or eliminate APOBEC3B polypeptide activity or expression in nearby uninfected cancer cells influenced by one or more of the inhibitor(s) generated within the infected cells.

In some cases, when administering viral nucleic acid (e.g., viral vectors) provided herein and/or viruses (e.g., oncolytic viruses) provided herein encoding (e.g., engineered to encode) one or more inhibitors of APOBEC3B polypeptide activity or expression provided herein to a mammal (e.g., a human) as described herein, the viral nucleic acid and/or viruses encoding one or more inhibitors of APOBEC3B polypeptide activity or expression can be effective to reduce or eliminate APOBEC3B polypeptide activity or expression in non-infected cells (e.g., non-infected bystander cells). In some cases, a non-infected bystander cell can be in direct contact (e.g., cell-cell contact) with an infected cell. In some cases, a non-infected bystander cell can be not in direct contact with an infected cell. When a non-infected bystander cell is not in direct contact with an infected cell, the non-infected bystander cell can in any appropriate location within a mammal (e.g., one or more inhibitors of APOBEC3B polypeptide activity or expression can be released from an infected cell and can travel anywhere in a mammals' body via, for example, the bloodstream to reduce or eliminate APOBEC3B polypeptide activity or expression in a bystander cell). For example, administering viral nucleic acid provided herein and/or viruses provided herein encoding one or more inhibitors of APOBEC3B polypeptide activity or expression to a mammal as described herein can be effective to reduce or eliminate APOBEC3B polypeptide activity or expression in non-infected cancer cells that can be killed via subsequent oncolytic infection or subsequent anti-cancer treatment.

In some cases, oncolytic viruses lacking nucleic acid encoding one or more inhibitors of APOBEC3B polypeptide activity or expression and viral nucleic acid (e.g., viral vectors) provided herein and/or non-oncolytic viruses provided herein encoding (e.g., engineered to encode) one or more inhibitors of APOBEC3B polypeptide activity or expression are administered to a mammal having, or at risk of developing, cancer to treat the mammal, the oncolytic viruses and the viral nucleic acid and/or non-oncolytic viruses encoding one or more inhibitors of APOBEC3B polypeptide activity or expression can be administered to the mammal at any appropriate time. In some cases, oncolytic viruses containing nucleic acid encoding one or more inhibitors of APOBEC3B polypeptide activity or expression can be used. In some cases, one or more viral vectors encoding one or more inhibitors of APOBEC3B polypeptide activity or expression and the one or more oncolytic viruses can be administered to the mammal at the same time. For example, one or more viral vectors encoding one or more inhibitors of APOBEC3B polypeptide activity or expression and one or more oncolytic viruses can be administered to the mammal at the same time. For example, one or more viral vectors encoding one or more inhibitors of APOBEC3B polypeptide activity or expression and including one or more oncolytic viruses can be administered (e.g., as a single composition) to the mammal. In some cases, one or more viral vectors encoding one or more inhibitors of APOBEC3B polypeptide activity or expression and the one or more oncolytic viruses can be administered to the mammal at the different times. For example, one or more viral vectors encoding one or more inhibitors of APOBEC3B polypeptide activity or expression can be administered to the mammal before or after the administration of one or more oncolytic viruses.

In some cases, viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be formulated into a composition (e.g., a pharmaceutically acceptable composition) for administration to a mammal (e.g., a human) having, or at risk of developing, cancer. For example, viral nucleic acid and/or viruses encoding one or more inhibitors of APOBEC3B polypeptide activity or expression can be formulated together with one or more pharmaceutically acceptable carriers (additives) and/or diluents. In some cases where viral nucleic acid and/or non-oncolytic viruses encoding one or more inhibitors of APOBEC3B polypeptide activity or expression and one or more oncolytic viruses are administered to a mammal, the viral nucleic acid and/or non-oncolytic viruses encoding one or more inhibitors of APOBEC3B polypeptide activity or expression and the one or more oncolytic viruses can be independently formulated with one or more pharmaceutically acceptable carriers (additives) and/or diluents in separate compositions (e.g., a first composition including viral nucleic acid and/or non-oncolytic viruses encoding one or more inhibitors of APOBEC3B polypeptide activity or expression and a second composition including one or more oncolytic viruses). In some cases where viral nucleic acid and/or non-oncolytic viruses encoding one or more inhibitors of APOBEC3B polypeptide activity or expression is a viral vector encoding one or more inhibitors of APOBEC3B polypeptide activity or expression and where one or more viral vectors encoding one or more inhibitors of APOBEC3B polypeptide activity or expression and one or more oncolytic viruses are administered to a mammal, both the viral nucleic acid and/or non-oncolytic viruses encoding one or more inhibitors of APOBEC3B polypeptide activity or expression and the one or more oncolytic viruses can be formulated together with one or more pharmaceutically acceptable carriers (additives) and/or diluents in a single composition (e.g., a composition including viral nucleic acid and/or non-oncolytic viruses encoding one or more inhibitors of APOBEC3B polypeptide activity or expression and including one or more oncolytic viruses). Pharmaceutically acceptable carriers, fillers, and vehicles that may be used in a pharmaceutical composition described herein include, without limitation, dimethyl sulfoxide (DMSO), ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and wool fat.

A composition including viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be designed for administered by any appropriate route. In some cases, administration can be local administration. In some cases, administration can be systemic administration. Examples of routes of administration include, without limitation, intravenous, intramuscular, subcutaneous, oral, intranasal, inhalation, transdermal, parenteral, and intratumoral administration. For example, a composition including viral nucleic acid and/or viruses encoding one or more inhibitors of APOBEC3B polypeptide activity or expression can be administered locally to a mammal having, or at risk of developing, cancer by injection into or near a tumor within the mammal. For example, a composition including viral nucleic acid and/or viruses encoding one or more inhibitors of APOBEC3B polypeptide activity or expression can be administered systemically by oral administration to a mammal having, or at risk of developing, cancer. In cases where multiple compositions are administered, a first composition and a second composition can be administered by the same route or can be administered by different routes. For example, a first composition including viral nucleic acid and/or non-oncolytic viruses encoding one or more inhibitors of APOBEC3B polypeptide activity or expression and a second composition including one or more oncolytic viruses described herein can be administered to the mammal by a same route (e.g., intratumorally). For example, a first composition including viral nucleic acid and/or non-oncolytic viruses encoding one or more inhibitors of APOBEC3B polypeptide activity or expression described herein can be administered to a mammal (e.g., a human) by a first route (e.g., intratumorally), and a second composition including one or more oncolytic viruses described herein can be administered to the mammal by a second route (e.g., intramuscularly).

A composition including viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be any appropriate route type of composition. Examples of compositions suitable for oral administration include, without limitation, liquids, tablets, capsules, pills, powders, gels, and granules. Examples of compositions suitable for parenteral administration include, without limitation, aqueous and non-aqueous sterile injection solutions that can contain anti-oxidants, buffers, bacteriostats, and solutes that render the formulation isotonic with the blood of the intended recipient.

A composition including viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk of developing, cancer in any appropriate amount (e.g., any appropriate dose). For example, any appropriate amount of oncolytic virus can be administered to a mammal as described herein. Effective amounts can vary depending on the severity of the cancer, the risk of developing cancer, the route of administration, the age and general health condition of the subject, excipient usage, the possibility of co-usage with other therapeutic treatments such as use of other agents, and the judgment of the treating physician. For example, in cases where a composition includes one or more oncolytic viruses, the composition can include from about $10^3$ plaque-forming units (PFUs) to about $10^{13}$ PFUs (e.g., from about $10^3$ to about $10^{13}$, from about $10^5$ to about $10^{13}$, from about $10^7$ to about $10^{13}$, from about $10^8$ to about $10^{13}$, from about $10^{10}$ to about $10^{13}$, from about $10^3$ to about $10^{10}$, from about $10^3$ to about $10^8$, from about $10^3$ to about $10^5$, from about $10^5$ to about $10^{10}$, from about $10^4$ to about $10^8$, from about $10^8$ to about $10^{10}$, or from about $10^{10}$ to about $10^{12}$ PFUs) of oncolytic viruses can be administered to a mammal as described herein. For example, in cases where a composition includes one or more oncolytic viruses, the composition can include oncolytic viruses at a multiplicity of infection (MOI) of from about 0.0000001 to about 10000 (e.g., from about 0.0000001 to about 1000, from about 0.0000001 to about 100, from about 0.0000001 to about 10, from about 0.0000001 to about 1, from about 0.000001 to about 10000, from about 0.00001 to about 10000, from about 0.0001 to about 10000, from about 0.001 to about 10000, from about 0.01 to about 10000, from about 0.1 to about 10000, from about 1 to about 10000, from about 10 to about 10000, from about 100 to about 10000, from about 1000 to about 10000, from about 0.001 to about 1000, or from about 0.1 to about 100) can be administered to a mammal as described herein. An effective amount of a composition including one or more oncolytic viruses can be any amount that reduces the severity of the cancer without producing significant toxicity to the mammal. The effective amount can remain constant or can be adjusted as a sliding scale or variable amount depending on the mammal's response to treatment. Various factors can influence the actual effective amount used for a particular application. For example, the frequency of administration, duration of treatment, use of multiple treatment agents, route of administration, severity of the cancer, and risk of developing cancer may require an increase or decrease in the actual effective amount administered.

A composition including viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk of developing, cancer in any appropriate frequency. The frequency of administration can be any frequency that reduces the severity of the cancer without producing significant toxicity to the mammal. For example, the frequency of administration can be from about once a day to about once a week, from about once a week to about once every two weeks, or from about once every two weeks to about once a month. The frequency of administration can remain constant or can be variable during the duration of treatment. As with the effective amount, various factors can influence the actual frequency of administration used for a particular application. For example, the effective amount, duration of treatment, use of multiple treatment agents, route of administration, severity of the cancer, and risk of developing cancer may require an increase or decrease in administration frequency.

A composition including viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk of developing, cancer for any appropriate duration. An effective duration for administering a composition including viral nucleic acid and/or viruses encoding one or more inhibitors of APOBEC3B polypeptide activity or expression can be any duration that reduces the severity of the cancer without producing significant toxicity to the mammal. For example, the effective duration can vary from several days to several months or years to a lifetime. In some cases, the effective duration for the treatment of a cancer can range in duration from about a month to about a year. Multiple factors can influence the actual effective duration used for a particular treatment. For example, an effective duration can vary with the frequency of administration, effective amount, use of multiple treatment agents, route of administration, severity of the cancer, and risk of developing cancer.

In some cases, viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk for developing, cancer as the sole active ingredient(s). For example, one or more viral vectors encoding one or more inhibitors of APOBEC3B polypeptide activity or expression and one or more oncolytic viruses can be administered to a mammal having, or at risk for developing, cancer as the sole active ingredients used to treat the mammal. For example, one or more oncolytic viruses encoding one or more inhibitors of APOBEC3B polypeptide activity or expression can be administered to a mammal having, or at risk of developing, cancer as the sole active ingredient used to treat the mammal.

In some cases, viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk for developing, cancer with one or more inhibitors of TNFα polypeptide activity or expression. For example, viral nucleic acid and/or viruses encoding one or more inhibitors of APOBEC3B polypeptide activity or expression can be administered with one or more inhibitors of TNFα polypeptide activity or expression to a mammal in need thereof. For example, viral nucleic acid and/or viruses encoding one or more inhibitors of APOBEC3B polypeptide activity or expression can be administered to a mammal having, or at risk for developing, cancer with one or more inhibitors of TNFα polypeptide activity or expression used to treat the mammal. The one or more inhibitors of TNFα polypeptide activity or expression used to treat a mammal having, or at risk of developing, cancer can include any appropriate inhibitor of TNFα polypeptide activity or expression. An inhibitor of TNFα polypeptide activity or expression can be any molecule that inhibits (e.g., reduces or eliminates) TNFα polypeptide activity or expression. An inhibitor of TNFα polypeptide activity or expression can be any appropriate type of molecule (e.g., nucleic acids such as siRNA molecules, shRNA molecules, antisense molecules, and targeting guide RNA molecules of a CRISPR/Cas9 system; and polypeptides such as antibodies and TALENs). For example, a mammal having cancer can be administered viral nucleic acid and/or viruses encoding one or more inhibitors of APOBEC3B polypeptide activity or expression and can be administered one or more additional cancer treatments. In cases where a mammal having cancer is treated with viral nucleic acid and/or viruses encoding one or more inhibitors of APOBEC3B polypeptide activity or expression and is treated with one or more inhibitors of TNFα polypeptide activity or expression, the one or more inhibitors of TNFα polypeptide activity or expression can be administered to a mammal at the same time or independently. For example, viral nucleic acid and/or viruses encoding one or more inhibitors of APOBEC3B polypeptide activity or expression and one or more inhibitors of TNFα polypeptide activity or expression can be administered to a mammal together (e.g., can be formulated together to form a single composition to be administered to a mammal). In some cases, viral nucleic acid and/or viruses encoding one or more inhibitors of APOBEC3B polypeptide activity or expression can be administered first, and the one or more inhibitors of TNFα polypeptide activity or expression administered second, or vice versa.

In some cases, viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk for developing, cancer together with one or more T cells and/or one or more agents that can stimulate one or more T cells. For example, viral nucleic acid and/or viruses encoding one or more inhibitors of APOBEC3B polypeptide activity or expression can be administered together with one or more T cells and/or one or more agents that can stimulate one or more T cells to a mammal in need thereof. For example, viral nucleic acid and/or viruses encoding one or more inhibitors of APOBEC3B polypeptide activity or expression can be administered to a mammal having, or at risk for developing, cancer together with one or more T cells and/or one or more agents that can stimulate one or more T cells to treat the mammal. The one or more T cells used to treat a mammal having, or at risk of developing, cancer can be any appropriate T cell. In some cases, a T cell can be a tumor reactive T cell. In some cases, a T cell can be a $CD8^+$ T cell or a $CD4^+$ T cell. In some cases, a T cell can be obtained from a mammal to be treated. In some cases, a T cell can be an engineered T cell. For example, a T cell can include (e.g., can be engineered to include) an engineered T cell receptor (TCR) such as a chimeric antigen receptor (CAR). A T cell including a CAR can also be referred to as a CAR T cell. When a T cell is a CAR T cell, the CAR T cell can be any appropriate CART cell (e.g., a CART cell targeting CD19, CD20, and/or CD22). An agent that can stimulate one or more T cells can include any appropriate agent. T cells can be stimulated (e.g., can be contacted with one more agents that can stimulate the T cells) in vivo or in vitro. For example, a mammal having cancer can be administered viral nucleic acid and/or viruses encoding one or more inhibitors of APOBEC3B polypeptide activity or expression and can be administered one or more T cells. In cases where a mammal having cancer is treated with viral nucleic acid and/or viruses encoding one or more inhibitors of APOBEC3B polypeptide activity or expression and is treated with one or more T cells, the one or more T cells can be administered to a mammal at the same time or independently. For example, viral nucleic acid and/or viruses encoding one or more inhibitors of APOBEC3B polypeptide activity or expression and one or more T cells can be administered to a mammal at the same time (e.g., can be formulated together to form a single composition to be administered to a mammal). For example, oncolytic viruses containing nucleic acid encoding one or more inhibitors of APOBEC3B polypeptide activity or expression and one or more CAR T cells can be administered to a mammal at the same time (e.g., can be formulated together to form a single composition to be administered to the mammal). In some cases, viral nucleic acid and/or viruses encoding one or more inhibitors of APOBEC3B polypeptide activity or expression can be administered first, and the one or more T cells administered second, or vice versa. For example, oncolytic viruses containing nucleic acid encoding one or more inhibitors of APOBEC3B polypeptide activity or expression can be administered first, and then the one or more CAR T cells administered second, or vice versa.

In some cases, when viral nucleic acid provided herein and/or viruses provided herein encoding one or more inhibitors of APOBEC3B polypeptide activity or expression are administered to a mammal having, or at risk of developing, cancer together with one or more T cells, cancer cells within the mammal can develop resistance to a T cell therapy at a reduced level (e.g., as compared to a level that develops in a comparable mammal administered a comparable T cell therapy in the absence of any inhibitor of APOBEC3B polypeptide activity or expression).

In some cases, when viral nucleic acid provided herein and/or viruses provided herein encoding one or more inhibitors of APOBEC3B polypeptide activity or expression are administered to a mammal having, or at risk of developing, cancer, cancer cells within the mammal can develop resistance to any other cancer treatment (e.g., radiation therapies, chemotherapies, hormone therapies, targeted therapies, and/or cytotoxic therapies) at a reduced level (e.g., as compared to a level that develops in a comparable mammal administered a comparable chemotherapy and/or a radiation therapy in the absence of any inhibitor of APOBEC3B polypeptide activity or expression).

In some cases, viral nucleic acid (e.g., viral vectors) provided herein and/or viruses (e.g., oncolytic viruses) provided herein encoding (e.g., engineered to encode) one or more inhibitors of APOBEC3B polypeptide activity or expression can be administered to a mammal (e.g., a human) having, or at risk for developing, cancer with one or more additional cancer treatments. For example, virus particles containing nucleic acid encoding one or more inhibitors of APOBEC3B polypeptide activity or expression can be administered with one or more additional cancer treatments to a mammal in need thereof. For example, virus particles containing nucleic acid encoding one or more inhibitors of APOBEC3B polypeptide activity or expression can be administered to a mammal having, or at risk for developing, cancer together with one or more additional cancer treatments used to treat the mammal. The one or more additional cancer treatments used to treat a mammal having, or at risk of developing, cancer can include any appropriate cancer treatment. In some cases, a cancer treatment can include surgery. In some cases, a cancer treatment can include radiation therapy. In some cases, a cancer treatment can include administration of one or more anti-cancer agents such as a chemotherapies, hormone therapies, targeted therapies, and/or cytotoxic therapies. For example, a mammal having cancer can be administered virus particles containing nucleic acid encoding one or more inhibitors of APOBEC3B polypeptide activity or expression and can be administered one or more additional cancer treatments. In cases where a mammal having cancer is treated with virus particles containing nucleic acid encoding one or more inhibitors of APOBEC3B polypeptide activity or expression and is treated with one or more additional cancer treatments, the one or more additional cancer treatments can be administered to a mammal at the same time or independently. For example, virus particles containing nucleic acid encoding one or more inhibitors of APOBEC3B polypeptide activity or expression and one or more anti-cancer agents can be administered to a mammal together (e.g., can be formulated together to form a single composition to be administered to a mammal). In some cases, virus particles containing nucleic acid encoding one or more inhibitors of APOBEC3B polypeptide activity or expression can be administered first, and the one or more additional cancer treatments administered second, or vice versa.

In certain instances, a course of treatment and the severity of a cancer can be monitored. Any appropriate method can be used to determine whether or not the severity of a cancer is reduced. For example, the severity of a cancer can be assessed using any appropriate methods and/or techniques, and can be assessed at different time points. For example, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests can be used to determine the severity of a cancer.

In some cases, the level of resistance development (if any) to a particular treatment (e.g., to oncolytic virus treatment or T cell therapy such as CAR T cell therapy) can be monitored following the treatment methods described herein.

The invention will be further described in the following examples, which do not limit the scope of the invention described in the claims.

Examples

Example 1: APOBEC3 Mediates Resistance to Oncolytic Viral Therapy

This Example identifies APOBEC3 as an important factor which restricts the potency of oncolytic Vesicular Stomatitis Virus (VSV) in oncolytic virus therapy.

Results

Resistant Tumor Cell Populations Emerge after Oncolytic Virus Treatment

Figure 1B:
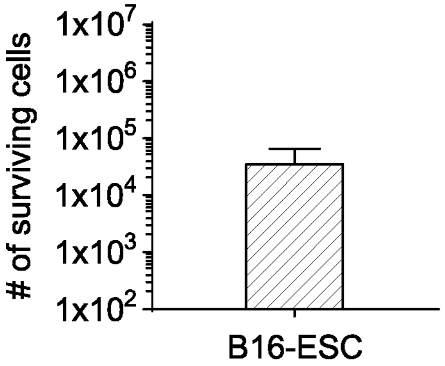
Figure 1C:
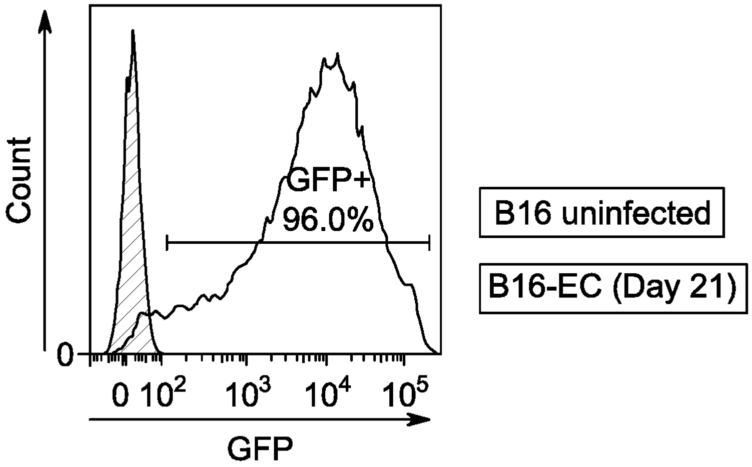
Figure 1D:
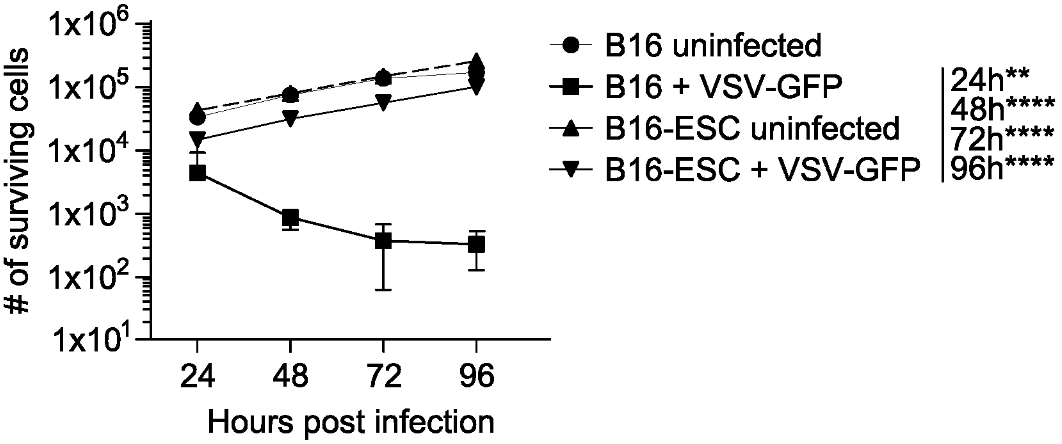

To investigate how tumor cells acquire resistance to viral therapy, murine B16 melanoma cells were infected with repetitive cycles of VSV-GFP at a low MOI (0.01) in vitro (FIG. 1A). Seven days after initial infection, surviving cells could be recovered, often as small, distinct colonies (FIG. 1A, inset). After two further rounds of infection at an MOI of 0.01, viable populations of VSV-resistant cells were recoverable by day 21 after the first infection (B16-ESC) (FIG. 1B). It was found that more than 95% of the live B16-ESC cells were positive for GFP expression indicating that they had been infected by the virus (FIG. 1C). The fact that the majority of the B16-ESC cells at day 21 were both infected and alive, suggests that the ESC population are significantly more resistant to VSV-mediated oncolysis than unselected parental B16 cells. To confirm that these colonies contained cells which were genuinely resistant to the oncolytic VSV, either B16 parental or B16-ESC cells were infected with VSV-GFP at an MOI of 0.01 and counted the number of surviving cells after infection. B16-ESC cells infected with VSV-GFP were able to resist infection and grew at a rate similar to uninfected controls (FIG. 1D).

Oncolytic VSV Resistance is Associated with an IFN-Dependent Upregulation of APOBEC3

Figures 2A, 2B, 2C, 2D, 2E, 2F:
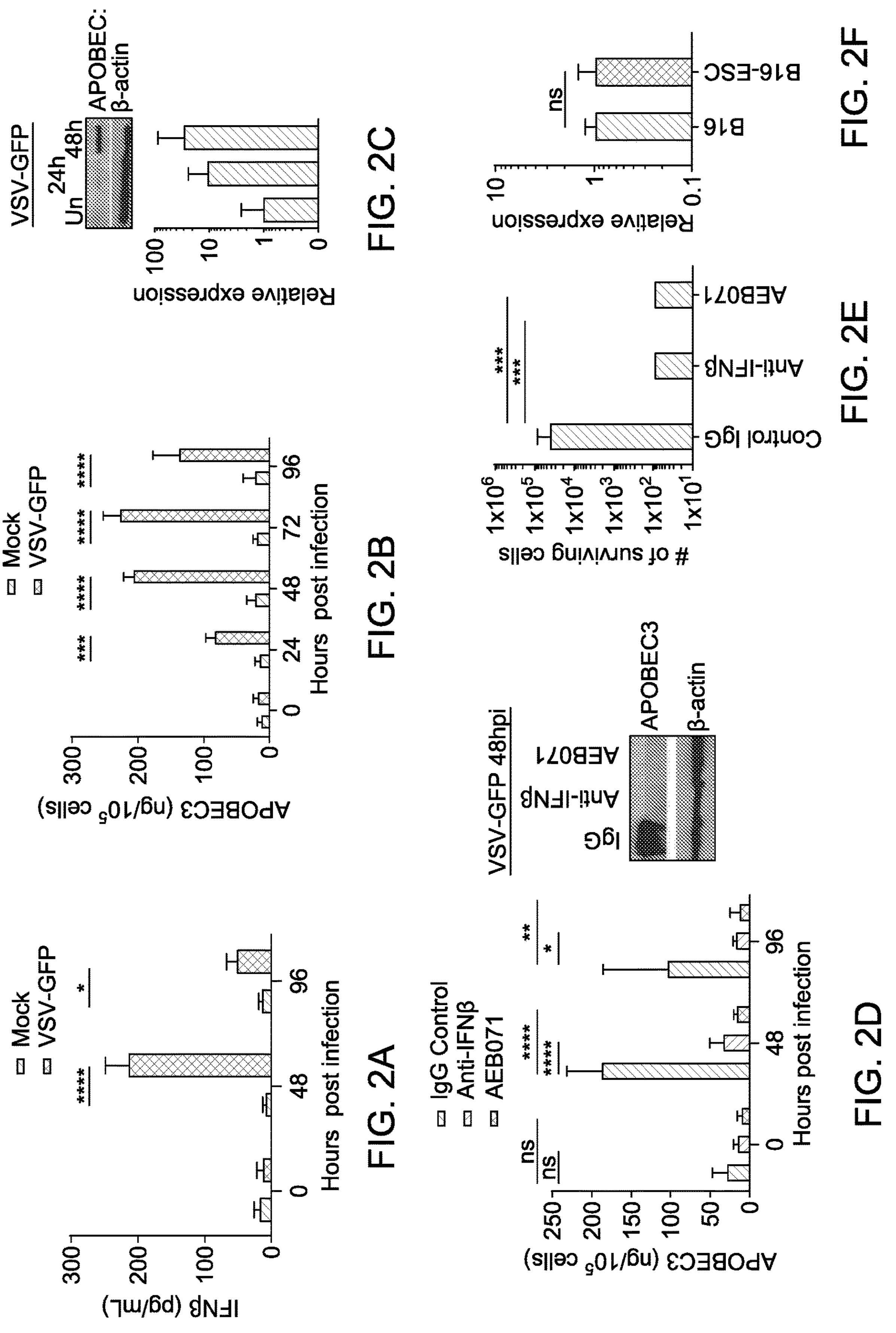

VSV-GFP infection of B16 cells induced moderate levels of type I IFN expression 48 hours post infection (FIG. 2A). Therefore, the acquisition of resistance to VSV oncolysis (FIG. 1) may be associated with the expression of IFN-inducible genes in infected cells. In this regard, the APOBEC3 family of cytosine deaminases are well-characterized as interferon inducible genes that can increase the mutational burden within tumor cells, allowing them to evolve and evade an applied therapy. Therefore, it was investigated whether APOBEC3 may play a role in the development of resistance to oncolytic VSV therapy. Interestingly, APOBEC3 was coordinately expressed with IFN-β following VSV infection as shown by ELISA and validated by western blot and qrtPCR (FIG. 2B, C). In addition, antibody-mediated blockade of IFN-β during VSV infection almost completely abolished APOBEC3 induction (FIG. 2D), as did the inhibitor of PKC/NF-κβ signaling, AEB071. The emergence of VSV-resistant cell populations (B16-ESC) was also significantly inhibited by either antibody blockade of IFN-β or PKC/NF-kβ signaling inhibition by AEB071 (FIG. 2E). Levels of murine APOBEC3 began to decline by 96 hours after infection (FIG. 2B), and were not significantly different in B16-ESC compared to B16 parental at a basal level (FIG. 2F). These data indicate that VSV induces a transient expression of APOBEC3 similar to that seen with classical interferon stimulated gene induction.

Taken together, these data led us to hypothesize that VSV-mediated induction of both type I interferon signaling and APOBEC3 expression is associated with enhanced tumor cell escape from viral oncolysis.

Increased IFN-β Expression Enhances Tumor Cell Resistance

Figures 3A, 3B, 3C, 3D, 3E, 3F:
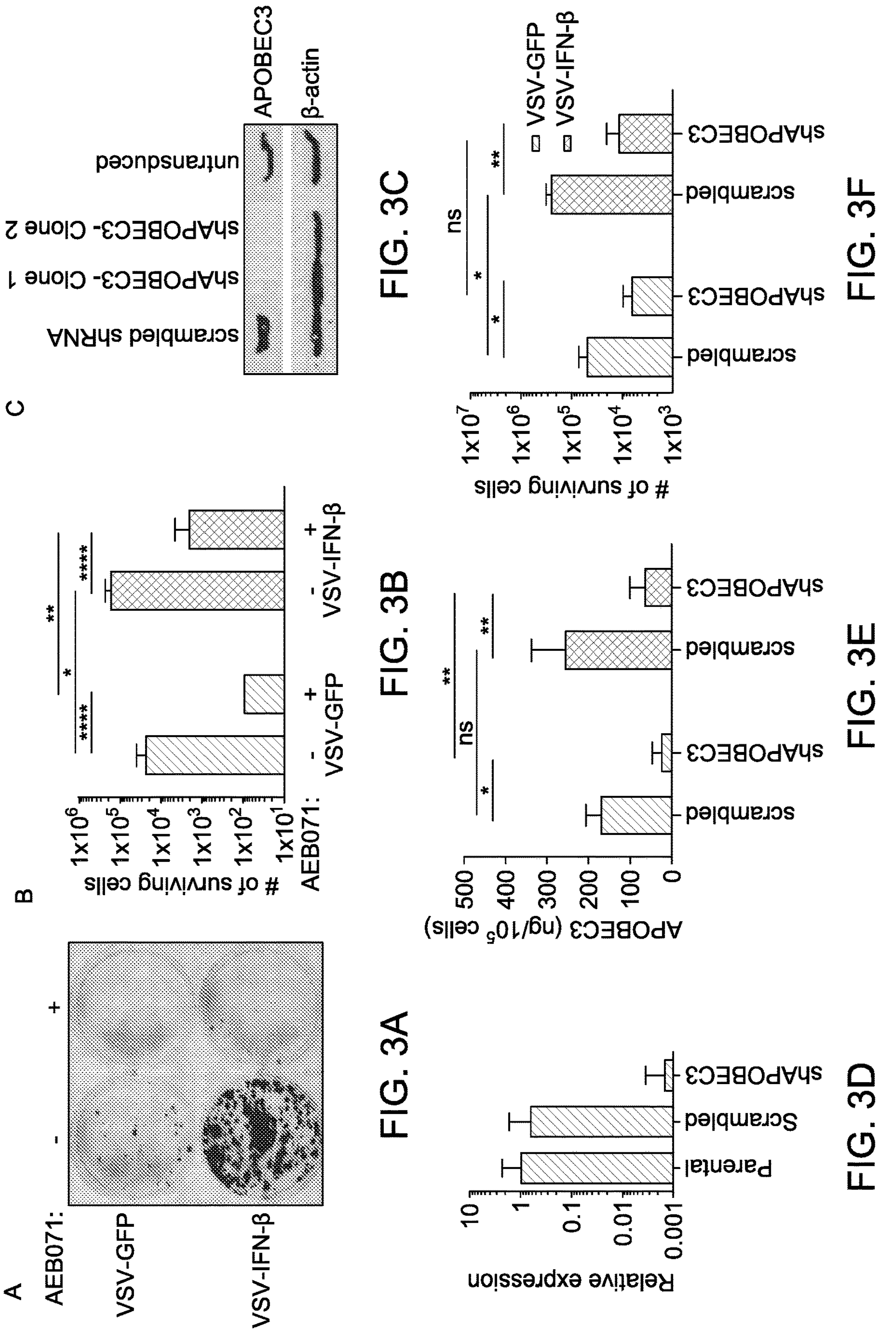

Consistent with a role for type I interferon induced genes being a key component in the de novo generation of oncolysis-resistant tumor cells, low MOI infection of B16 cells for 7 days with VSV-IFN-β generated more VSV-resistant colonies than did infection with VSV-GFP (FIG. 3A). Inhibition of PKC/NF-κβ signaling by AEB071 during VSV-GFP or VSV-IFN-β infection significantly inhibited the outgrowth of resistant colonies (FIG. 3A). More VSV-resistant cells were recovered from repeated virus infection, as in FIG. 1A, if cells were infected with VSV-IFN-β compared to VSV-GFP (FIG. 3B). Inhibition of PKC/NF-κβ signaling significantly inhibited escape from VSV-IFN-β and, more effectively, from VSV-GFP (FIG. 3B). These data show that IFN-β enhances the generation of B16-ESC populations through a signaling pathway that also induces APOBEC3 expression in infected tumor cells.

To demonstrate that APOBEC3 contributed to the acquisition of resistance to VSV infection, B16 cells in which expression of APOBEC3 had been knocked down with shRNA, as shown by ELISA and validated by western blot and qrtPCR (FIG. 3C,D, E), were infected with VSV-GFP or VSV-IFN-β. Overexpression of IFN-β from VSV led to increased, although not significant, levels of APOBEC3 (FIG. 3E), from that induced by VSV-GFP. The infection of B16(shAPOBEC3) cells with either VSV-GFP or VSV-IFN-β virus led to both significantly lower levels of APOBEC3 expression (FIG. 3E), as well as significantly fewer VSV-resistant B16-ESC VSV populations (FIG. 3F), than did infection of B16 cells transduced with a scrambled, control shRNA (FIG. 3C,F). These data indicate that, while APOBEC3 is unlikely to be the only interferon inducible response factor that contributes to viral resistance, it does have a significant impact on the generation of cells that are able to evade VSV therapy.

APOBEC3 Inhibition Reduces Escape from VSV Therapy

To investigate whether APOBEC3 played an important role in the in vivo generation of resistance to viral oncolytic therapy, mice bearing 3 day established B16 parental, B16 (scrambled RNA), or B16(shAPOBEC3) tumors were injected with nine doses of VSV-GFP at the site of tumor cell injection. Over two separate experiments, fewer than 10% of mice injected with B16(shAPOBEC3) tumors escaped VSV therapy to form recurrent tumors (FIG. 4). In contrast, 65% of mice with B16(scrambled) tumors escaped VSV treatment to form recurrent tumors (FIG. 4). All PBS injected mice developed tumors and required euthanasia by day 25. These data support the hypothesis that the expression of APOBEC3 contributes to the outgrowth of VSV resistant tumors.

Human APOBEC3B Plays a Role in Resistance to Oncolytic VSV Therapy

Figure 5B:
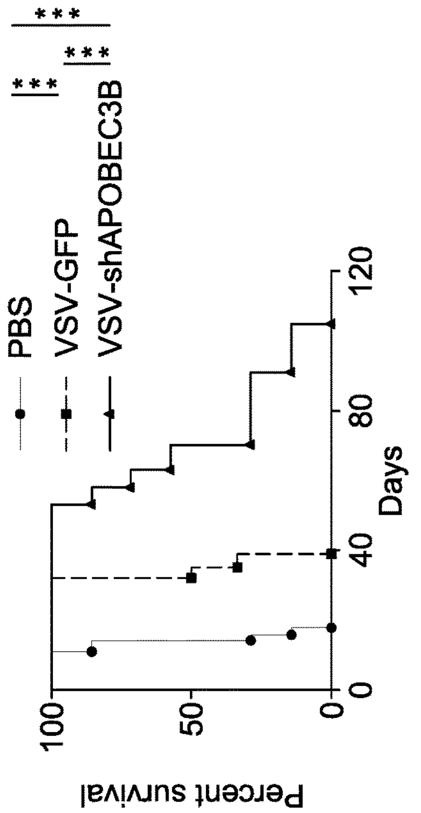
Figure 5A:
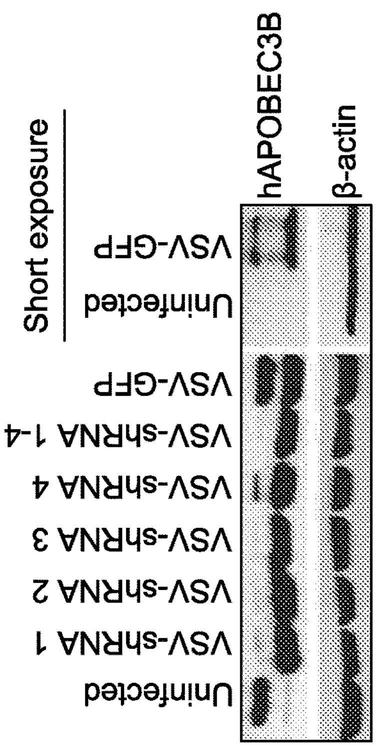
Figure 5C:
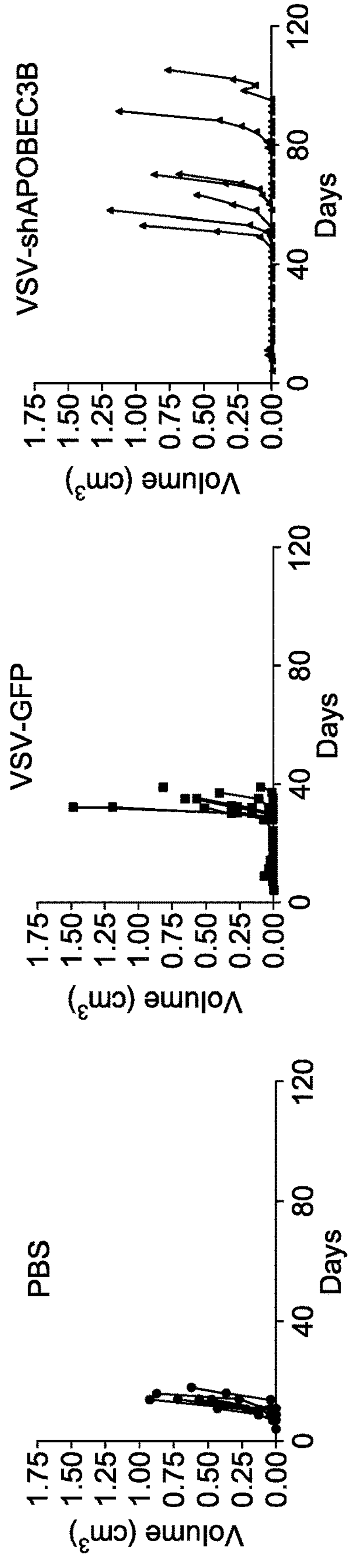

Whether human APOBEC3B may recapitulate the function of murine APOBEC3 to drive the development of VSV-resistant populations in a human Mel888 xenograft tumor model was examined. VSV vectors expressing four shRNAs against hAPOBEC3B individually, or in combination (shRNA 1-4), were generated and knock down of human APOBEC3B in Mel888 cells infected with each vector was confirmed by western blot (FIG. 5A). VSV expressing shRNA1-3, as well as the combination of all 4 shRNA, dramatically reduced the expression of hAPOBEC3B. A non-specific band (**) was observed in all VSV-infected cells suggesting cross reactivity of the antibody against a VSV antigen. Indeed, this was confirmed by infection with VSV-GFP which did not result in a reduction in hAPOBEC3B expression but did show the non-specific band (FIG. 5A). Similar to induction of mAPOBEC3 in B16 cells (FIG. 2), VSV-mediated induction of APOBEC3B in Mel888 cells was confirmed using a shorter exposure than that used in FIG. 5A, left panel which was overexposed to detect any APOBEC3B protein expressed after shRNA knock down (FIG. 5A, right panel). Treatment of mice bearing subcutaneous Mel888 tumors with nine doses of VSV expressing the combination of shRNAs (VSV-shAPOBEC3B) significantly improved survival compared to treatment with VSV-GFP or PBS (FIG. 5B). VSV-shAPOBEC3B treated mice had controlled tumor growth out to 50 days in contrast to VSV-GFP mice who all succumbed to tumor before day 40 (FIG. 5C). These data support a role for human APOBEC3B in promoting resistance to oncolytic VSV therapy.

Tumors Overexpressing hAPOBEC3B Readily Escape VSV Therapy

Figure 6B:
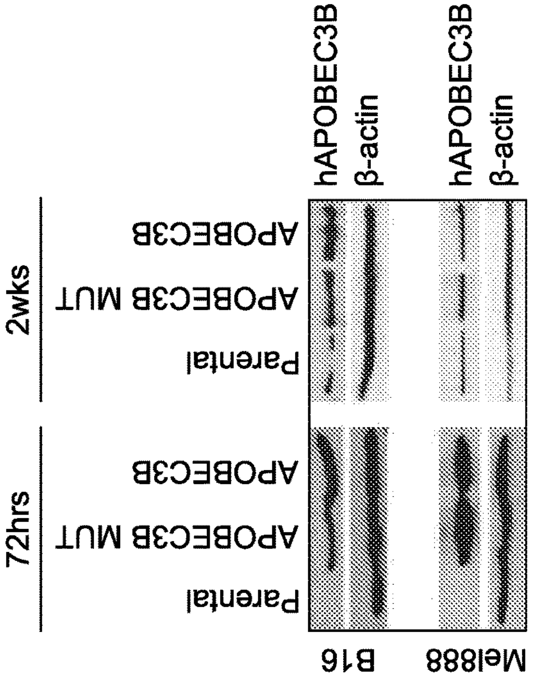
Figure 6D:
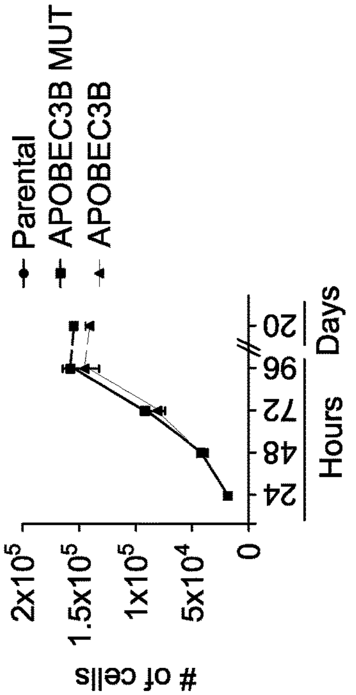

A mutated, enzymatically non-functional (FIG. 6A, lower), or a fully functional human APOBEC3B protein (FIG. 6A, upper) was overexpressed in tumor cells by transduction with a retroviral vector and expression was confirmed by western blot and qrtPCR (FIG. 6B, C). Robust hAPOBEC3B expression was observed 72 hours post transduction and decreased to a lower, yet still elevated level, compared to parental controls by 2 weeks. This could be due to toxicity associated with overexpression of hAPOBEC3B, which may act as a mutagen, selecting for cells which express a lower level of hAPOBEC3B. B16 cells overexpressing the mutated, non-functional APOBEC3B developed resistance to VSV following a low MOT infection with VSV-GFP over 21 days (FIG. 6E) at a similar rate to parental B16 cells. The growth rate of the B16-APOBEC3B cell line was not greater than that of the B16-APOBEC3B MUT or parental B16 cell lines after 5 repeated passages for 96 hours (out to day 20) indicating that the increased frequency of VSV escape in the B16-APOBEC3B cell line was not due to altered growth rates associated with overexpression of APOBEC3B (FIG. 6D). However, B16 cells overexpressing functional APOBEC3B were better able to resist VSV infection compared to either wild-type B16 or B16 (APOBEC3B MUT) (FIG. 6E). These effects were not specific to the B16 cell line as increased resistance to VSV oncolysis was observed in both the murine glioma GL261, and in the human melanoma Mel888 cell lines when engineered to overexpress APOBEC3B, after the 21 day treatment period (FIG. 6F, G). Transient overexpression of the APOBEC3B protein, but not the APOBEC3B MUT protein, was associated with a significant decrease in viability of infected B16 cells (FIG. 6H). These data show that the deaminase-competent APOBEC3B protein exerts significant toxicity—possibly through its geno-toxic, mutator activity—which is absent from the deaminase-incompetent APOBEC3B MUT protein. However, despite the toxicity of APOBEC3B expression, the fact that its expression allows for greater levels of cell survival upon VSV infection (FIGS. 6E-F) suggest that it allows for selection of a virus resistant phenotype.

Figure 6E:
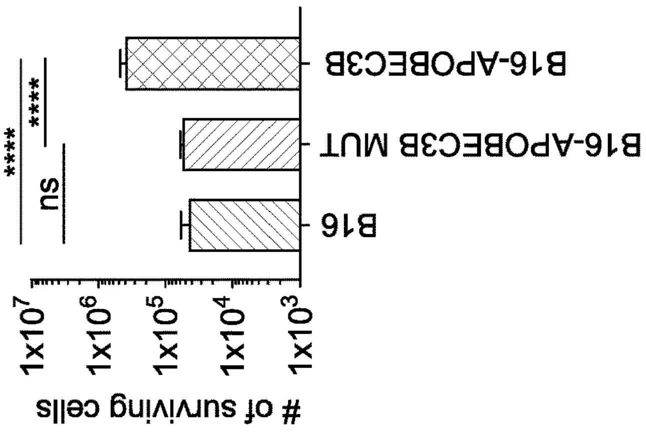
Figure 7C:
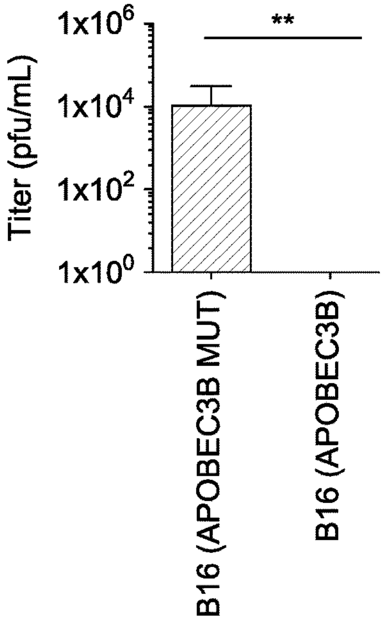

Consistent with the in vitro data (FIG. 6E), B16 tumors overexpressing human APOBEC3B treated with nine intratumoral injections of VSV-GFP escaped VSV therapy significantly more quickly than control tumors expressing the mutated APOBEC3B (FIG. 7A, B). B16-APOBEC3B MUT expressing cells were used as the negative control in these experiments as previous data indicated target cell killing are equivalent between B16 parental and B16-APOBEC3B MUT cell lines (FIG. 6E). In addition, low, but detectable, levels of VSV-GFP were recovered from most of the B16 (APOBEC3B MUT) tumors at sacrifice (FIG. 7C). In contrast, no virus was recovered from any of the B16 (APOBEC3B) treated tumors (FIG. 7C). These data confirm that overexpression of APOBEC3B in tumors increased the rate at which tumors escaped from oncolytic virotherapy, and suggested that it may also reduce the fitness of the oncolytic virus.

hAPOBEC3B Overexpression Reduces VSV Fitness

Figure 8A:
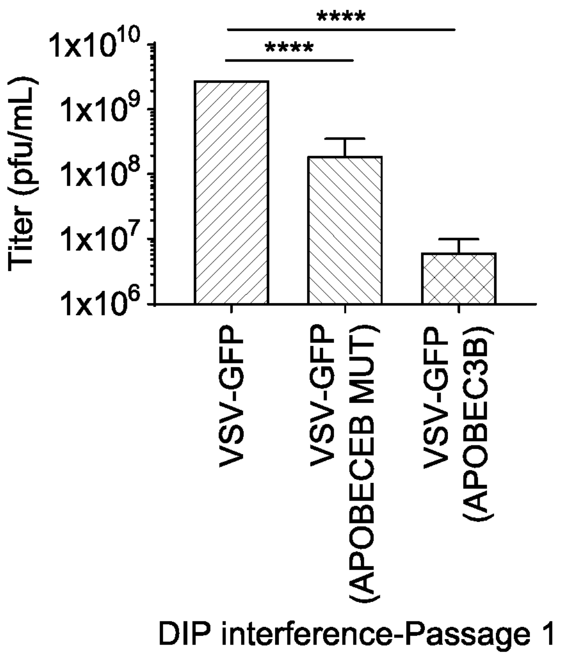
Figure 8B:
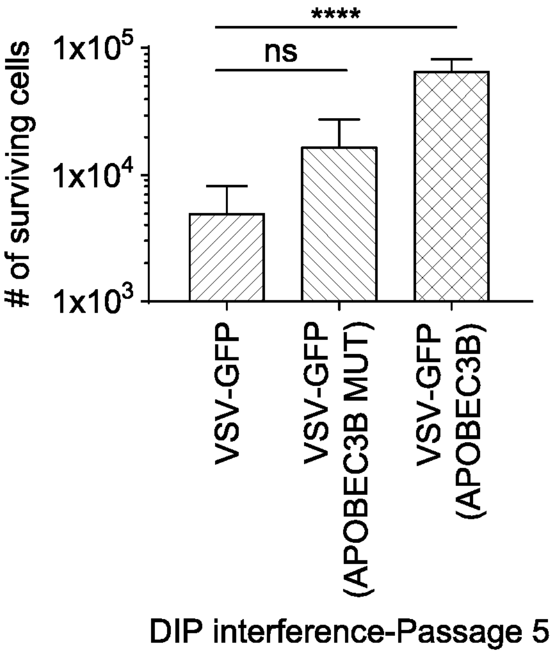
Figure 8C:
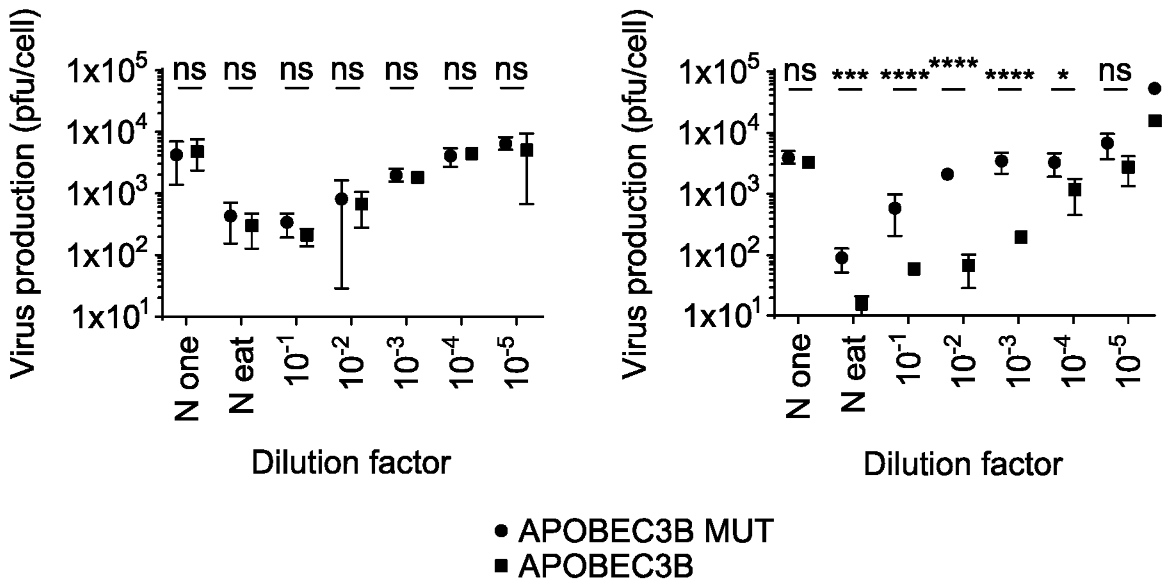

The data has shown that APOBEC3 contributed to generation of a virus-resistant phenotype of infected tumor cells (FIG. 4). In addition, given the lack of recoverable virus from APOBEC3B over-expressing tumors (FIG. 7C), and consistent with its role as a restriction factor against viral infection, upregulation or overexpression of APOBEC3/APOBEC3B respectively may also directly affect VSV fitness. Indeed, approximately 10 fold less virus was recovered after repeated passage through B16(APOBEC3B) cells compared to passage through B16(APOBEC3B MUT) cells (FIG. 8A). Moreover, when used to reinfect parental B16 cells at an MOI of 0.01, VSV recovered from 21 day passage through B16(APOBEC3B) cells was significantly less cytolytic than both the stock virus and virus recovered from the B16(APOBEC3B MUT) cells (FIG. 8B). To further characterize the loss of fitness of the virus recovered from APOBEC3B overexpressing cells the burden of defective interfering particles (DIPs) in the viral population following multiple passages through either B16(APOBEC3B MUT) or B16(APOBEC3B) cells was quantified. DIP content in each viral passage was quantified by measuring the ability of a viral preparation collected after passage to interfere with infection with a stock virus. After a single passage through either B16(APOBEC3B) or B16(APOBEC3B MUT) cell lines, virus recovered after passage interfered equally with infection of target cells by the stock virus indicating similar DIP contents (FIG. 8C). However, following five in vitro passages, virus recovered from B16(APOBEC3B) cells contained significantly more interfering DIPs than did virus recovered from B16(APOBEC3B MUT) cells (FIG. 8C). These data showed that there are more non-functional particles in the supernatant recovered from APOBEC3B overexpressing cells, suggesting that APOBEC3B may directly mutate the virus genome. Taken together, these data suggest that APOBEC3B results in decreased oncolytic activity both by facilitating the emergence of tumor cells resistant to oncolytic virus activity, and restricting the fitness of the virus directly by altering the viability of progeny particles.

Materials and Methods

Cell Lines

Murine melanoma B16 cells were cultured in DMEM supplemented with 10% Fetal Bovine Serum (FBS). B16TK cells were derived from a B16.F1 clone transfected with a plasmid expressing the Herpes Simplex Virus thymidine kinase (HSV-1 TK) gene. Following stable selection in 1.25 μg/mL puromycin, these cells were shown to be sensitive to Ganciclovir (Cymevene) at 5 μg/ml. B16-APOBEC3B and B16-APOBEC3B MUT cells were maintained in DMEM 10% FBS at 37° C. 10% $CO_2$, and selected in hygromycin (200 μg/mL). Baby hamster kidney (BHK) cells were cultures in DMEM supplemented with 10% Fetal Bovine Serum (FBS). All cell lines were maintained at 37° C. 10% $CO_2$ and regularly shown to be free of *Mycoplasma* infection.

Mice 6-8 week old female C57BL/6 mice were purchased from Jackson Laboratories (Bar Harbor, Me.).

Viruses

VSV was generated from pXN2 cDNA plasmid using the established reverse genetics system in BHK cells as described elsewhere (see, e.g., Whelan et al., *Proc Natl Acad Sci USA* 92:8388-8392 (1995)). All transgenes were inserted between the viral G and L protein using the XhoI and NheI restriction sites. Virus titers were determined by plaque assay on BHK cells.

Generation of Virus Resistant Cell Lines

B16 cells were infected at an MOI of 0.01 (VSV) for 1 hour, washed with phosphate buffer (PBS), and then incubated for 7 days. Dead cells were removed every 2 days by washing with PBS. After 7 days, the cells were collected by detachment with trypsin, and replated. These cells were subjected to two repeated rounds of infection as previously described. After 21 days, or three total rounds of infection, the remaining virus-escape cells were collected. This protocol was performed in the presence or absence of anti-IFNβ antibody (Rabbit polyclonal anti-mouse interferon beta, (01 interferon source, Piscataway, N.J.), PKC signaling inhibitor (AEB071; 10 μM) (MedChemExpress, Monmouth Junction, NJ), or control IgG (Chrome Pure anti-rabbit IgG; catalog no. 011-000-003; The Jackson Laboratory).

Protein Quantification

Murine APOBEC3 was measured by Western Blot using a rabbit monoclonal anti-APOBEC3 (184990, Abcam, San Francisco, Calif.); human APOBEC3B was measured by Western Blot using a rabbit polyclonal anti APOBEC3B PA5-11430 (Thermo Fisher). Murine APOBEC3 was measured by rabbit monoclonal anti-human APOBEC3B ELISA (Abcam, San Francisco, Calif.) which reacts with both human APOBEC3B and murine APOBEC3 according to the manufacturer's instructions. Murine IFN-β was measured by direct ELISA (R&D systems) according to the manufacturer's instructions.

Quantitative RT-PCR

RNA was prepared with the QIAGEN-RNeasy-MiniKit (Qiagen, Valencia, Calif.). 1 μg total RNA was reverse-transcribed in a 20 μl volume using oligo-(dT) primers using the First Strand cDNA Synthesis Kit (Roche, Indianapolis, Ind.). A cDNA equivalent of 1 ng RNA was amplified by PCR with gene-specific primers using GAPDH as loading control (mgapdh sense: TCATGACCACAGTCCATGCC (SEQ ID NO:5); mgapdh antisense: TCAGCTCTGG-GATGACCTTG (SEQ ID NO:6); APOBEC3 sense: ATGGGACCATTCTGTCTGGGA (SEQ ID NO:7); APOBEC3 antisense: TCAAGACACGGGGGTCCAAG (SEQ ID NO:8)). qRT-PCR was carried out using a LightCycler480 SYBRGreenI Master kit and a LightCycler480 instrument (Roche) according to the manufacturer's instructions. The $\Delta\Delta C_T$ method was used to calculate the fold change in expression level of APOBEC3 relative to GAPDH and normalized to an untreated calibrator sample.

APOBEC Knockdown and Overexpression

Four separate mouse unique 29mer shRNA retroviral constructs, or a single scrambled shRNA encoding retroviral construct (Origene Technologies, Rockville, Md.) were transfected into the GP+E86 ecotropic packaging cell line and supernatant was used to infect B16TK cells to generate the B16TK (shRNA APOBEC3) and B16TK scrambled shRNA populations, respectively. In addition, a single scrambled negative control non-effective shRNA cassette was similarly packaged and used to infect B16TK cells to generate B16TK (scrambled shRNA) cells.

Figure 6A:
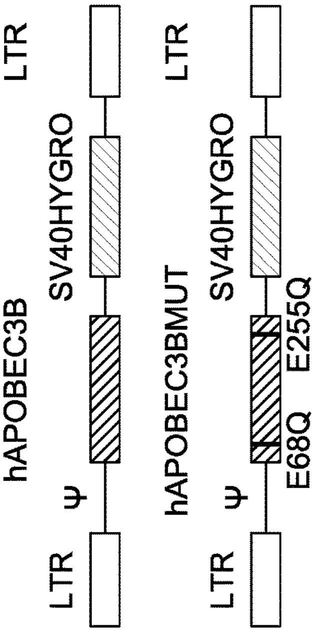
Figure 6C:
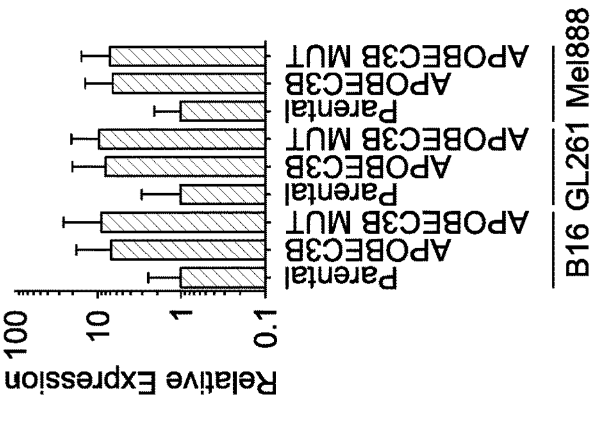
Figure 6F:
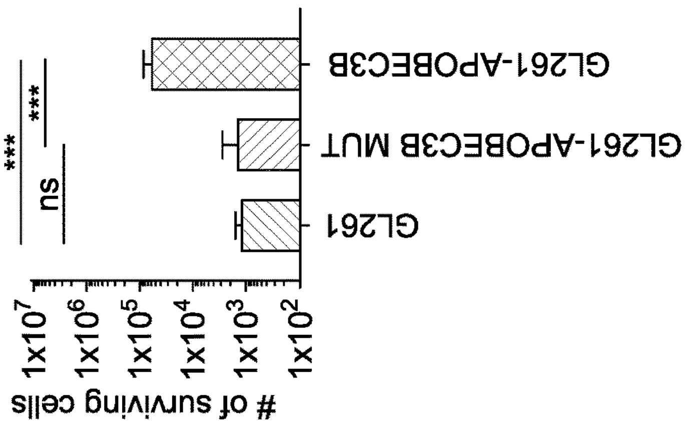
Figure 6G:
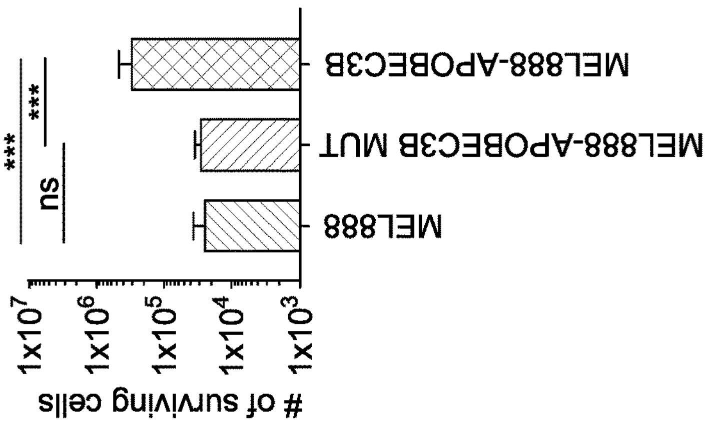
Figure 6H:
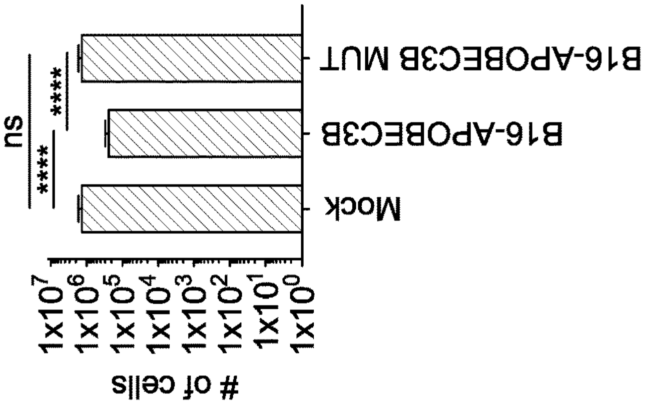

B16TK tumor cell lines were engineered to over express human APOBEC3B, or a catalytically inactive form of the protein APOBEC3B MUT, following infection with either pBABE-Hygro APOBEC3B or pBABE-Hygro APOBEC3B MUT (see, e.g., Pak et al., *J Virol* 85:8538-8547 (2011)) (See FIG. 6A). Forty-eight hours post infection, bulk populations of cells were selected in hygromycin for 2 weeks and used for experiments.

Defective Interfering Particle Assay

B16-APOBEC3B MUT or B16-APOBEC3B overexpressing cells were infected with VSV-GFP at an MOI of 0.01 and incubated for 24 hours. Supernatant was collected and 1 mL of supernatant was used to infect a fresh monolayer of cells. This was repeated out to five passages. The DIP assay was done by serially diluting passage 1 and passage 5 of VSV-GFP from B16-APOBEC3B MUT or B16-APOBEC3B cells (1:10 to 1:100,000). Fresh BHK cells were seeded the day before in triplicate wells, and diluted viral supernatants were allowed to adsorb for 1 hour. Stock VSV-GFP virus was then added at an MOI of 20 ($8\times10^5$ pfu/well) and incubated for 1 hour. Cells were then washed 3× in PBS and fresh supernatant was added. Supernatant was collected 24 hours post infection and tittered by plaque assay by limiting dilution on BHK cells.

In Vivo Experiments

All in vivo studies were approved by the Institutional Animal Care and Use Committee at Mayo Clinic. Mice were challenged subcutaneously with $2\times10^5$ B16TK melanoma cells, in 100 μL PBS (HyClone, Logan, Utah). All virus injections were delivered intratumorally in 50 μl volume. Tumors were measured 3 times per week, and mice were euthanized when tumors reached 1.0 cm in diameter. Mice were sacrificed upon emergence of neurological symptoms or weight loss.

Statistics

Survival curves were analyzed by the Log-Rank test. Student's T tests, one way ANOVA and two way ANOVA were applied for in vitro assays as appropriate. Statistical significance was set at $p\leq0.05$ for all experiments.

Summary

These results show that oncolytic viral infection with VSV induces a type I IFN-dependent upregulation of APOBEC3 that promotes the generation of virus-resistant tumor cell populations and reduces the oncolytic fitness of the virus itself. For example, these results identify APOBEC3 as a target to improve the efficacy of oncolytic platforms and other viral based therapies. APOBEC3 overexpression generates significant levels of cellular genomic mutations and at least some of these can act to decrease viral replication. Accordingly, APOBEC3 can be targeted during virus infection to improve the therapeutic outcome of oncolytic viral therapy.

Example 2: Sub-Optimal T Cell Therapy Drives a Tumor Cell Mutator Phenotype that Promotes Escape from Frontline Treatment This Example shows that weak affinity/low frequency T cell responses against tumor antigens may actively contribute to the ability of tumor cells to evolve away from frontline therapies. Therefore, immunotherapies need to be optimized as early as possible so that, if they do not kill the tumor completely, they do not promote treatment resistance.

Results

Tumor Cell Escape from Therapy is Enhanced by the Presence of Tumor Reactive CD8 T Cells.

Figure 9A:
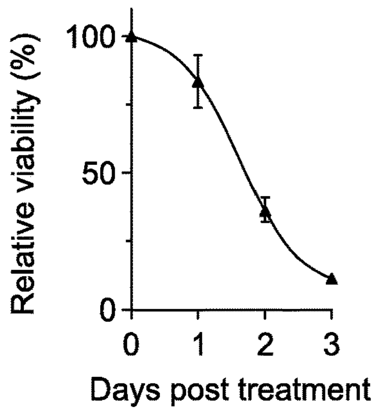
Figure 9B:
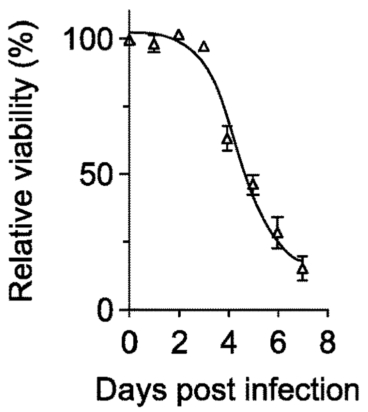
Figure 9C:
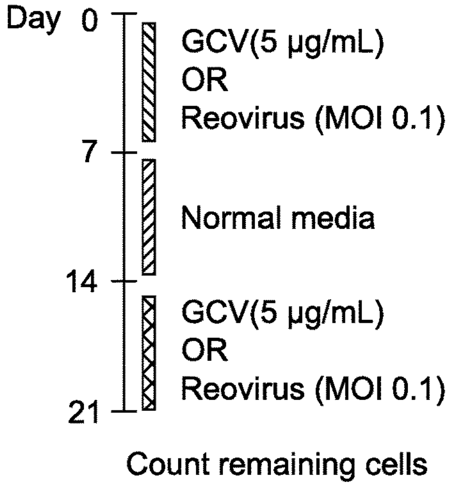
Figure 9D:
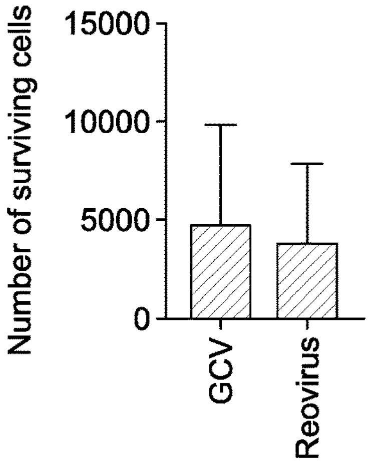
Figure 9E:
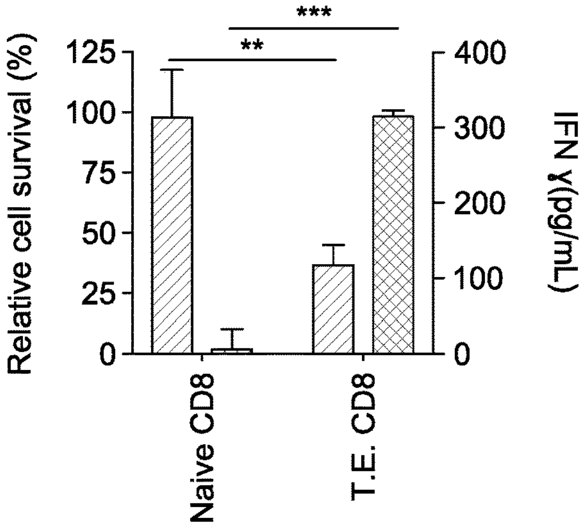
Figure 9F:
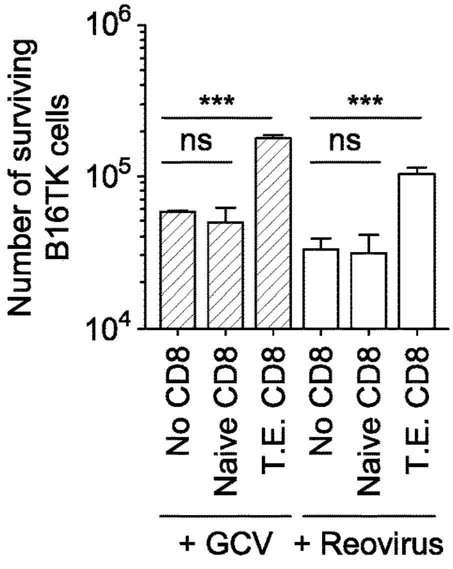
Figure 10A:
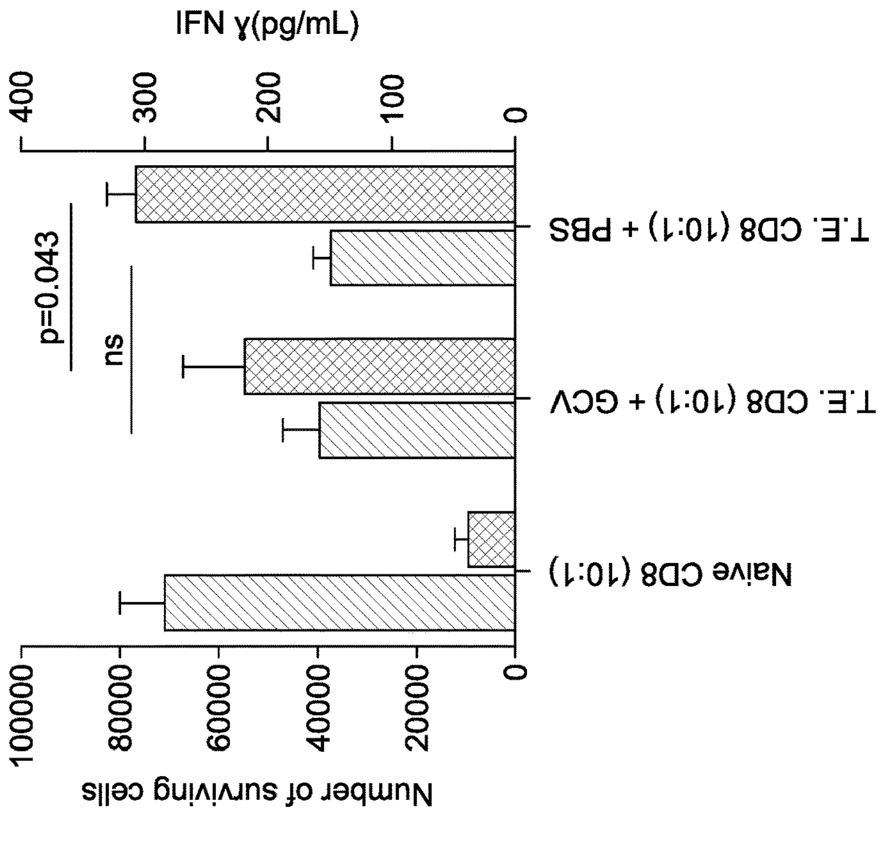

B16 cells expressing the HSV-1 thymidine kinase (B16TK) were sensitive to treatment with ganciclovir (GCV) at 5 μg/mL (FIG. 9A) or reovirus at an MOI of 0.1 (FIG. 9B). However, despite the induction of significant cell death, a small proportion of cells survived as escape variants following two consecutive weekly cycles of treatment with GCV or reovirus (FIG. 9C, D). Clearance of B16TK tumors by GCV in immune competent mice is dependent upon CD8 T cells, and tumor-cured mice have significant CD8 T cell responses against parental B16 cells. Purified CD8 T cells from mice which had rejected B16TK tumors following GCV therapy (tumor experienced CD8; T.E. CD8) killed target B16TK cells and produced IFNγ at low levels in vitro when cultured at an effector to target (E:T) ratio of 10:1 (FIG. 9E). It was reasoned that the combination of GCV, or reovirus, with T.E. CD8 T cells would lead to enhanced cumulative cell killing. However, when purified T.E. CD8 T cells were co-cultured with B16TK cells at an E:T ratio of 10:1 at the time of treatment with GCV or infection with reovirus, a significant increase in the number of B16TK cells which survived was observed compared to those treated in the absence of T cells. In contrast, this enhanced outgrowth was not observed when B16TK cells were treated with GCV or reovirus in the presence of CD8 T cells purified from naïve C57/BL6 mice (FIG. 9F). It was confirmed that the functionality of the T.E. CD8 T cells was not compromised by GCV. The cytotoxicity of the T.E. CD8 T cells was unaffected, and the secretion of IFNγ was only modestly reduced in the presence of GCV when they were co-cultured with parental B16 cells, as opposed to B16TK cells (FIG. 10A). In addition, the activation of OT-I CD8 T cells was increased in the presence of reovirus (FIG. 10B) showing that the virus does not diminish CD8 T to cell function and cannot explain the increased survival of the target cells.

Figure 12B:
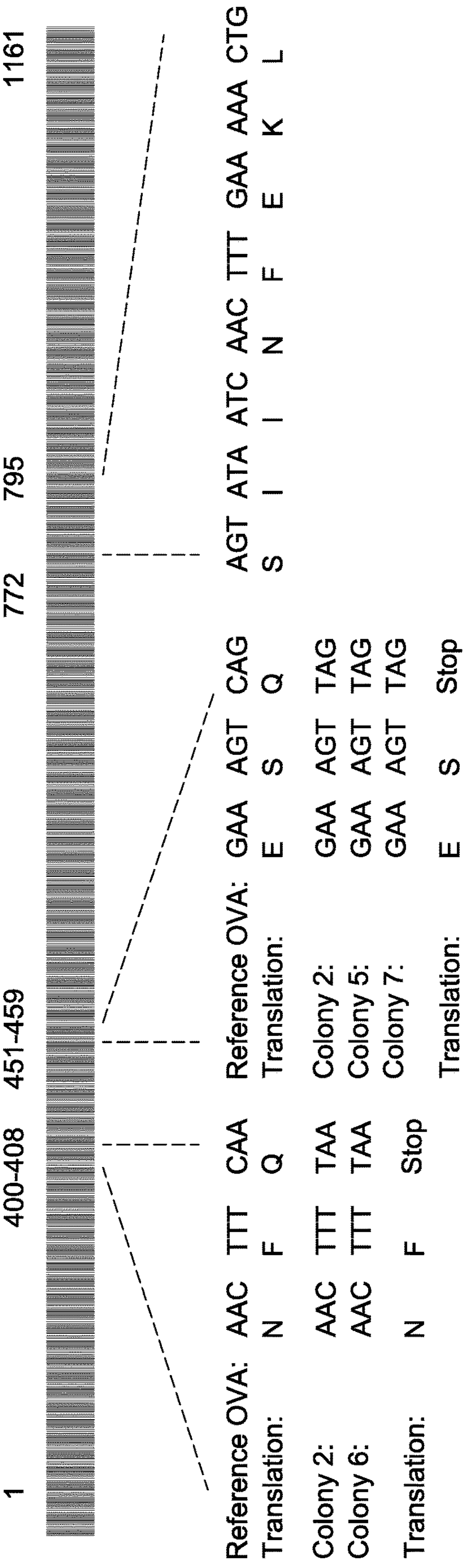

A CD8 T Cell Mutator Phenotype is Associated with C-T Mutation of Target Antigen To investigate this phenomenon in a model with a defined antigenic target, the potential of B16OVA cells to escape therapy when co-cultured with in vitro activated CD8 OT-I T cells was evaluated. At high E:T ratios (50:1 and 10:1), no discrete surviving escape colonies of B16OVA were observed (Table 2). At lower ratios (5:1 and 1:1) individual colonies of B16OVA cells could be isolated as escape variants, and were subsequently resistant to further OT-I killing, even at high E:T ratios (FIG. 11). B16TK cells do not express the ova gene and were therefore not targeted by OT-I T cells. Either naïve or T.E. CD8 T cells were introduced into the OT-I CD8 T cell-B16OVA co-culture system at an T.E. effector to OT-I effector to target ratio of 10:10:1, and emerge of escape variant B16OVA clones was observed (Table 3, timeline outlined in FIG. 12A). In contrast, when B16OVA cells were co-cultured with activated CD8 OT-I T cells, or activated CD8 OT-I T cells in combination with naïve CD8 T cells at an E:E:T ratio of 10:10:1, complete target cell killing was observed. 15 clones from the T.E. CD8 and OT-I co-culture condition were isolated and expanded. Ten of these clones showed complete loss of the ova gene. However, 5 of 15 escape B16OVA clones retained the ova gene. Sequencing revealed that 4 of 5 clones contained a TC to TT conversion in two locations (positions 406 and 457), both of which generated a premature STOP codon upstream of the immunodominant MHC class I binding SIINFEKL (SEQ ID NO:9) epitope (FIG. 12B). The B16OVA cells used in the experiment of FIG. 12 and Table 3 were originally derived from a single cell clone of B16OVA selected for high level recognition by OT-I T cells and with a fully sequenced ova gene. In addition, none of the mutant OVA-containing clones emerged from co-culture with OT-I alone or OT-I with naïve CD8 T cells (Table 3). Taken together, these data suggest that these OVA mutant-containing B16OVA cells were selected for by a gain of mutation induced in the OT-I/T.E. CD8 T co-cultures.

TABLE 2

Generation of escape variants in a co-culture system with OT-I T cells.

| | Number of colonies | |
|---|---|---|
| Effector: target ratio | B16OVA | B16TK |
| 50:1 | 0; 0; 0 | Confluent |
| 10:1 | 0; 0; 0 | Confluent |
| 5:1 | 7; 19; 12 | Confluent |
| 1:1 | 33; 50; 17 | Confluent |
| 1:5 | Confluent | Confluent |

TABLE 3

Generation of B16OVA escape variants in a co-culture system with OT-I T cells and T.E. CD8 T cells.

Number of colonies

| OT-I only (E:T is 10:1) | OT-I + Naïve CD8 T cells (E:E:T is 10:10:1) | OT-I + T.E. CD8 T cells (E:E:T is 10:10:1) |
|---|---|---|
| 0; 0; 0 | 0; 0; 0 | 3; 15; 1 |

Weak T Cell Responses Induce APOBEC3 Expression

Figure 13A:
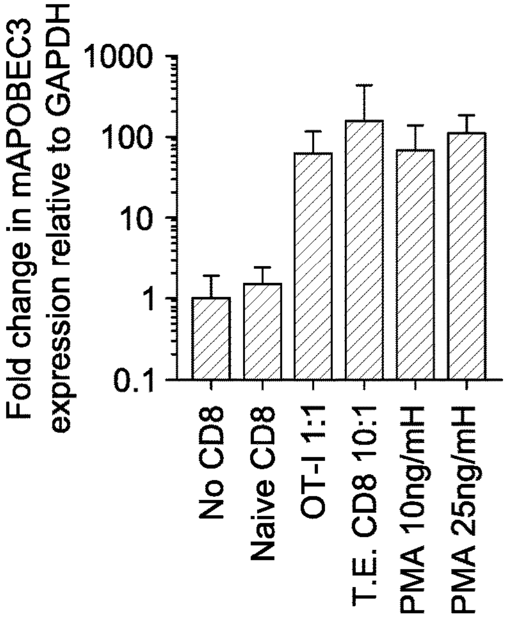
Figure 13B:
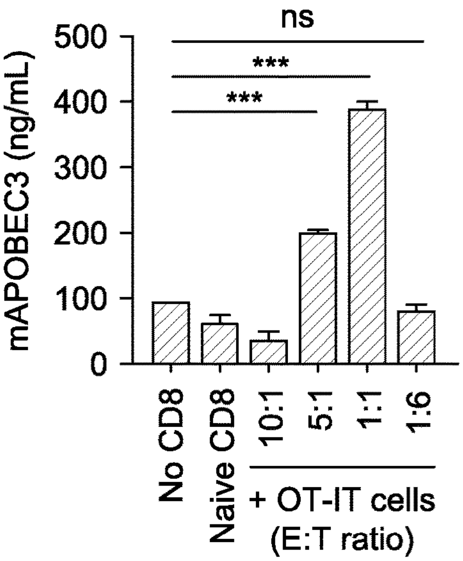
Figure 13C:
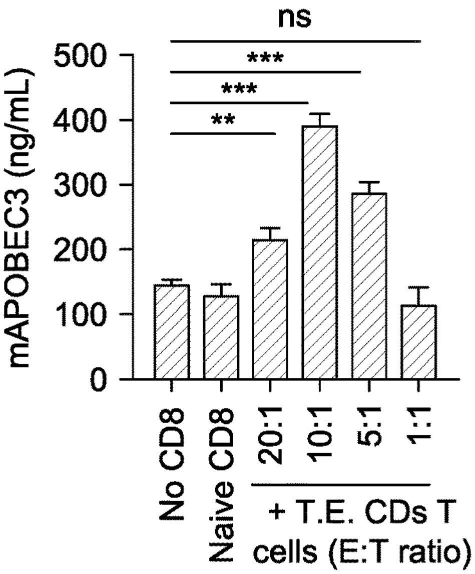
Figure 13D:
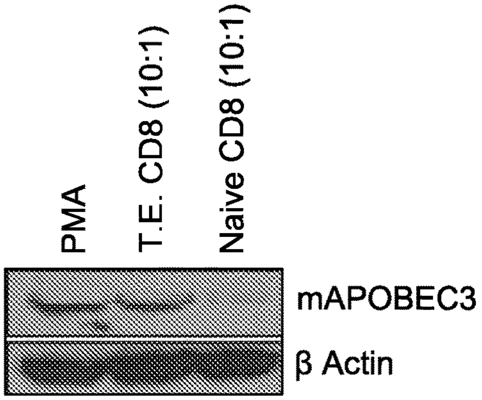

The first hotspot C to T transition mutation in the ova gene was consistent with the previously reported murine APOBEC3 motif TXC, and both hotspots were consistent with that of the APOBEC3B cytosine deaminase with an A in the +1 position (TCA) (Roberts et al., *Nat Genet.* 45(9): 970-6 (2013); MacMillan et al., *J Virol.* 87(9):4808-17 (2013); Shi et al., *Nat Struct Mol Biol.* 24(2):131-139 (2017); Nair et al., *J Virol.* 88(7):3850-60 (2014); and Chen et al., *PLoS Comput Biol.* 13(3):e1005471 (2017)). It was therefore hypothesized that T cell interaction may induce an equivalent murine APOBEC3B-like activity in tumor cells, which plays a role in generating cellular mutations that allow for escape from therapy. The expression of mAPOBEC3 was evaluated by qRT-PCR in tumor cells following co-culture with tumor reactive T cells at effector to target ratios at which escape variants were observed.

mAPOBEC3 mRNA expression rose sharply after 12 hours of co-culture with OT-I or T.E. CD8 T cells, as well as following treatment with the PKC activator PMA (FIG. 13A). Similarly, mAPOBEC3 protein was induced in B16OVA cells at suboptimal E:T ratios with OT-I CD8 T cells (5:1 and 1:1), but not at a high E:T ratio (10:1) (FIG. 13B), consistent with the outgrowth of escape variants (Table 3). This same effect was observed in B16TK cells co-cultured with T.E. CD8 T cells at low E:T ratios, with maximal upregulation of mAPOBEC3 at a ratio of 10:1 (FIG. 13C). The different T.E. CD8 and OT-I E:T ratios required for maximal mAPOBEC3 induction likely reflects the lower frequency of antigen-specific T cells in the T.E. CD8 population. The upregulation of mAPOBEC3 was also confirmed by western blot at the respective suboptimal T cell effector to target ratios (FIG. 13D).

Figure 13E:
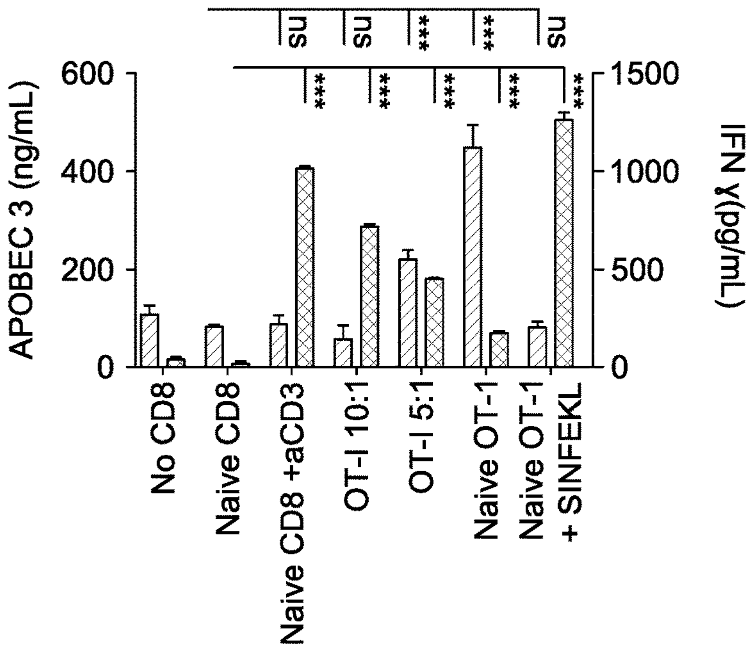

Upregulation of APOBEC3 in tumor cells at suboptimal effector to target ratios inversely correlated with the secretion of the effector cytokine IFNγ (FIG. 13E). Co-culture of CD8 OT-I cells with B16OVA cells at an E:T ratio of 10:1 induced robust IFN-γ production, but little mAPOBEC3 expression, and as the ratio was reduced, APOBEC3 expression rose. Naïve OT-I cells that had not previously been activated in vitro, but which express a transgenic TCR specific for the SIINFEKL (SEQ ID NO:9) epitope of OVA, produced low levels of IFNγ when co-cultured with B16OVA cells (which present SIINFEKL (SEQ ID NO:9) at low levels to the OT-I T cells), and stimulated high levels of mAPOBEC3 expression from the target cells. Conversely, naïve OT-I cells co-cultured with B16OVA cells in the presence of exogenous SIINFEKL (SEQ ID NO:9) peptide produced high IFNγ, and low levels of mAPOBEC3 induction. High E:T ratios were also associated with high levels of TNFα secretion from OT-I T cells (FIG. 13F), which decreased as the number of activated T cells was reduced.

Figure 13G:
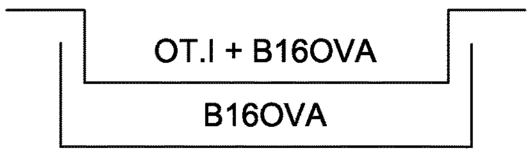
Figure 13F:
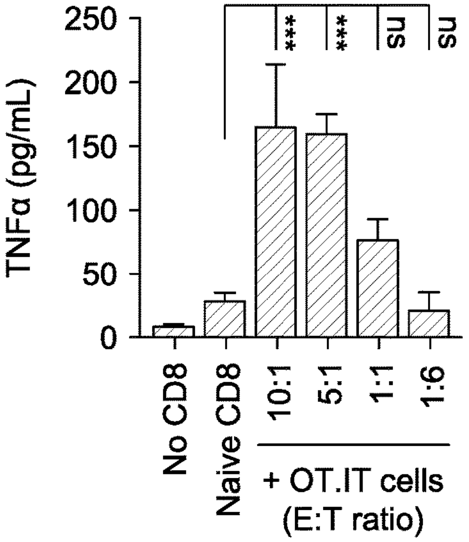
Figure 13H:
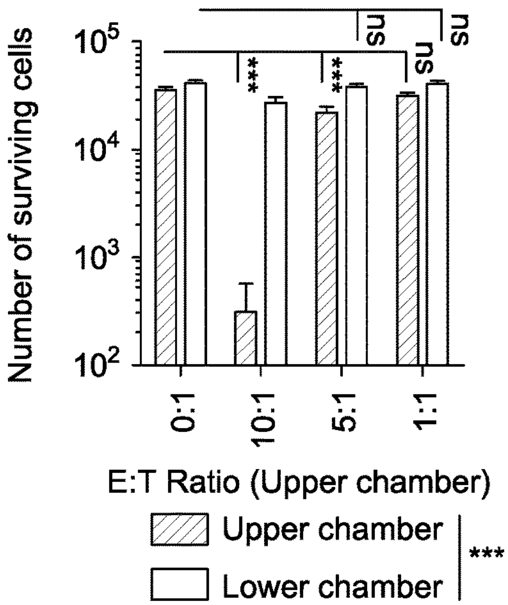
Figure 131:
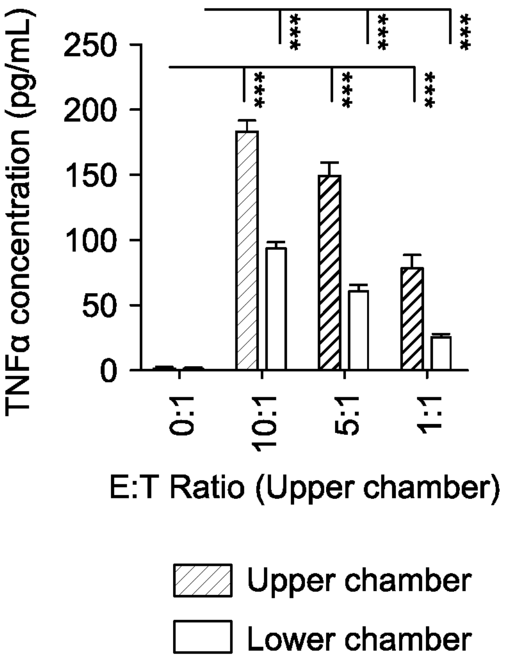
Figure 13J:
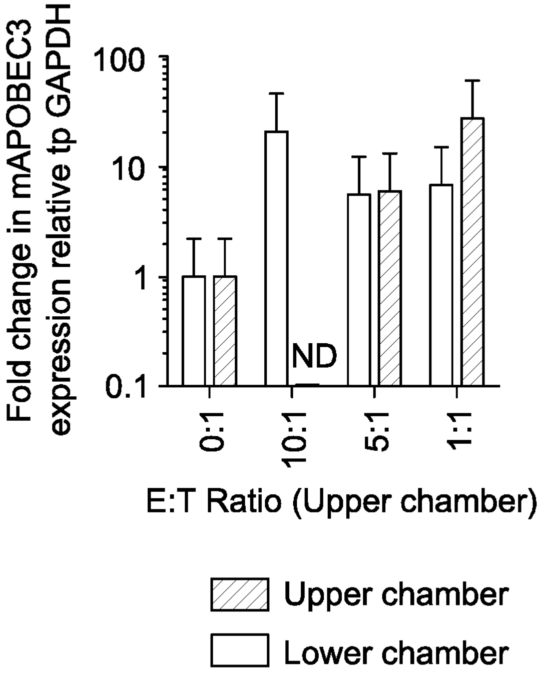

To show the relationship between the E:T ratio of T cell killing, TNF-α levels, and mAPOBEC3 induction, a transwell co-culture system was used in which B16OVA target tumor cells were co-cultured with effector OT-I T cells in the upper chambers, and (bystander) B16OVA cells were plated in the lower chambers (FIG. 13G). In the upper chamber, at the high E:T ratio of 10:1 OT-I: tumor cells, most of the target B16OVA tumor cells were killed (FIG. 13H), with correspondingly high levels of T cell activation-associated TNFα in the cultures (FIG. 13I), such that levels of mAPOBEC3 could not be measured because of a lack of surviving cells (FIG. 13J). At the lower E:T ratios of 5:1 and 1:1 direct T cell-mediated tumor cell killing was greatly reduced (FIG. 13H). However, in these surviving tumor cells, levels of APOBEC3 were significantly elevated (FIG. 13J), and were associated with high levels of TNFα induced by the T cell co-cultures (even though these E:T ratios were not able directly to kill B16OVA at high levels) (FIG. 13I). At all E:T ratios of T cell co-cultures in the upper chambers, the bystander B16OVA tumor cells not directly exposed to T cells in the lower chambers survived at high levels (FIG. 13H). However, as a result of the T cell activity in the upper chambers, TNFα was still detected at significant levels above background in the lower chambers (FIG. 13I), and this was associated with induction of mAPOBEC3 in the bystander B16OVA cells (FIG. 13J).

Figure 13K:
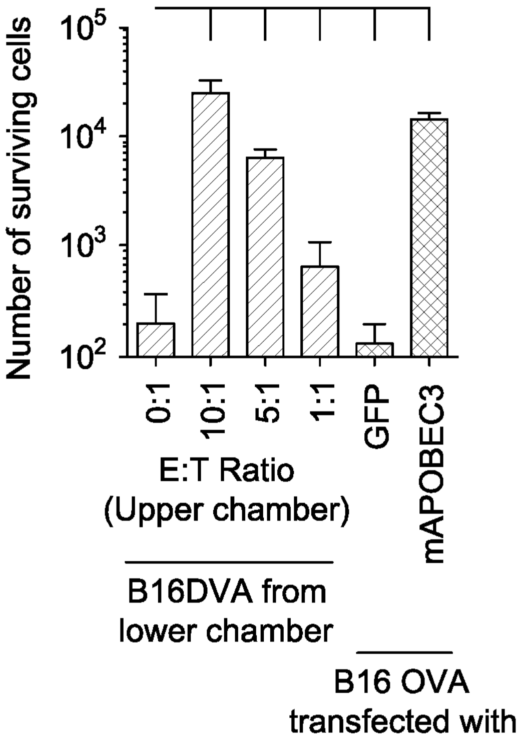
Figure 13L:
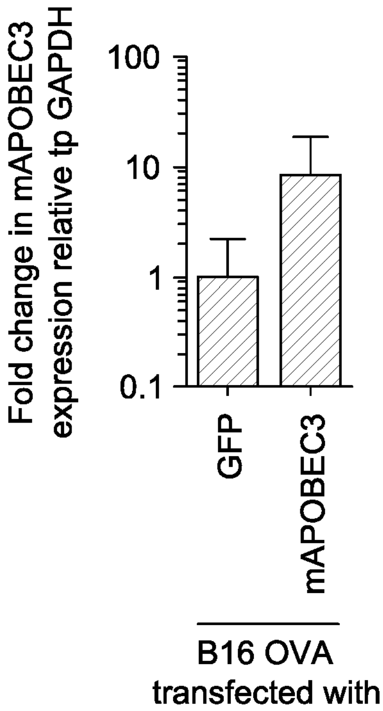

Those bystander B16OVA cells which survived in the lower chambers following exposure to TNFα, and in which mAPOBEC3 had been induced (FIGS. 13H-J), were significantly more resistant to killing by OT-I T cells when re-plated in fresh co-cultures than were parental B16OVA cells (FIG. 13K). The bystander B16OVA cells recovered from the lower chambers of the E:T 10:1 co-cultures were the most resistant to subsequent OT-I cell killing (FIG. 13K). These bystander B16OVA cells had been exposed to the highest levels of TNFα as a result of T cell activation and killing in the upper chambers (FIG. 13I, lower chambers) and had the highest levels of mAPOBEC3 induction (FIG. 13J, lower chambers). The levels of resistance to OT-I T cell killing in these bystander B16OVA cells were equivalent to that induced by de-novo over-expression of mAPOBEC3 in B16OVA cells (FIGS. 13K&L), suggesting that mAPOBEC3 is a major mediator of the T cell induced, bystander tumor cell escape from therapy. Taken together, these data show that when ineffective T cell killing clears only a proportion of tumor cells, bystander cells, either directly in contact with T cell activity, or which are physically separated from the T cells themselves yet are exposed to T cell-derived factors such as TNFα, can upregulate mAPOBEC3 expression and acquire mutations which may provide them with a selective advantage.

Figure 14B:
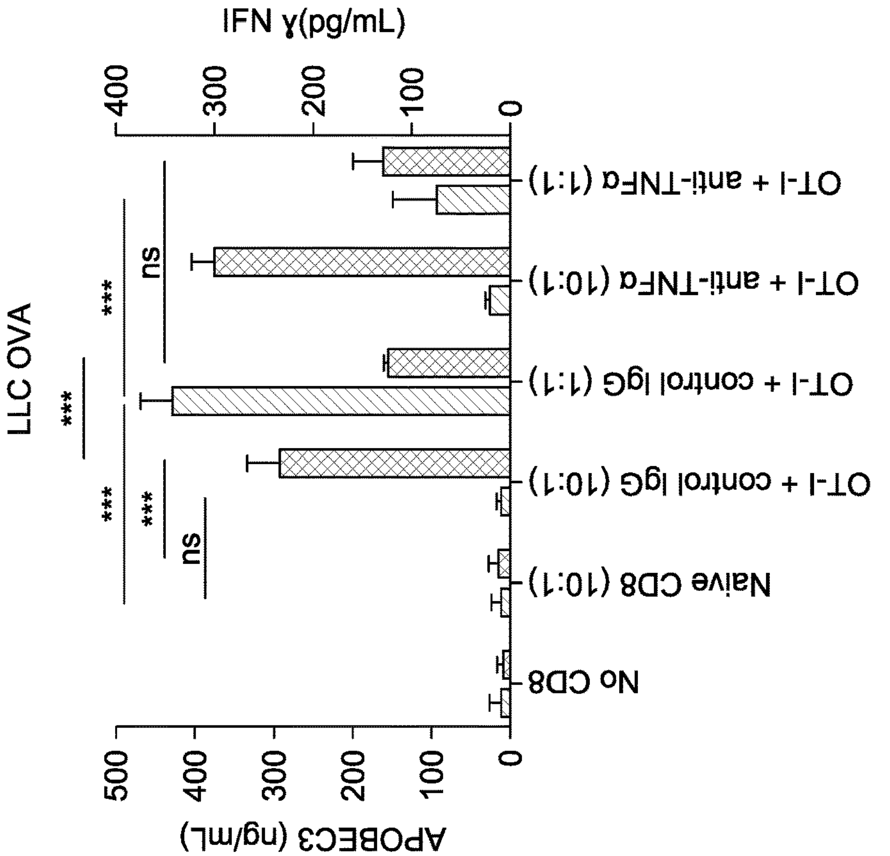
Figure 14A:
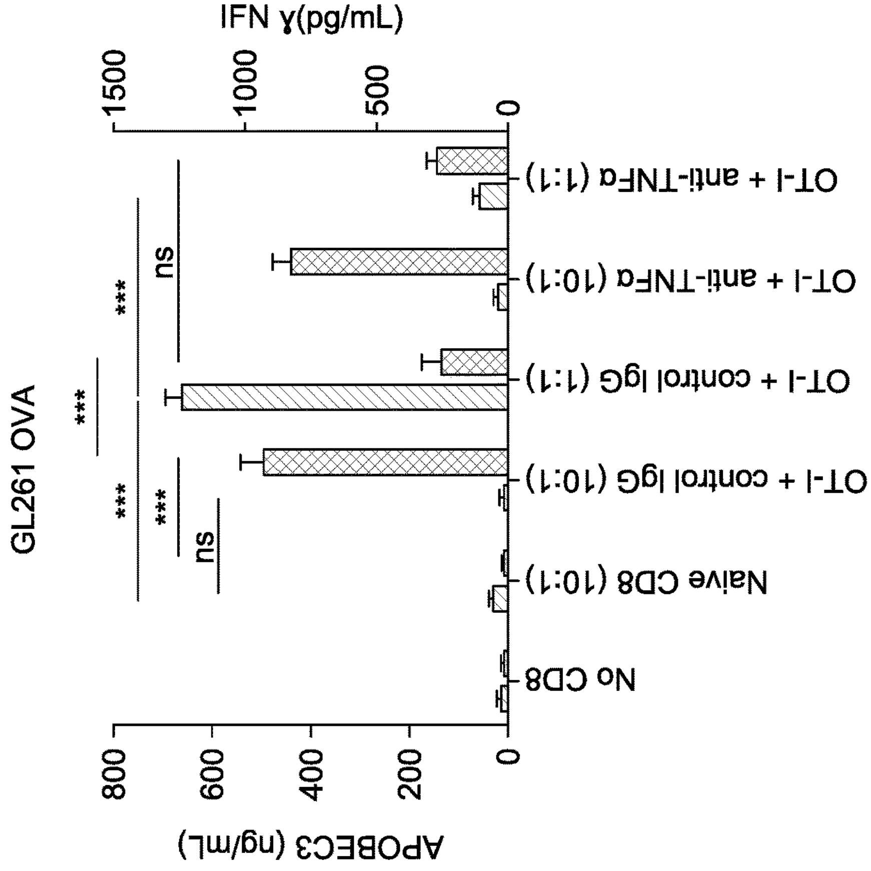
Figure 15A:
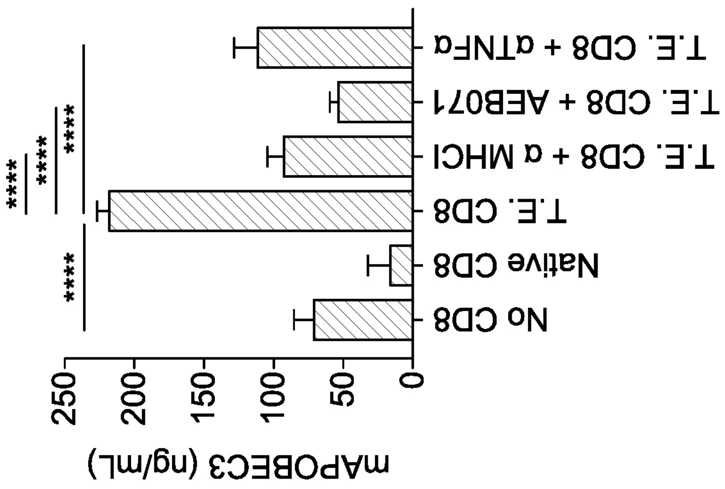
Figure 15B:
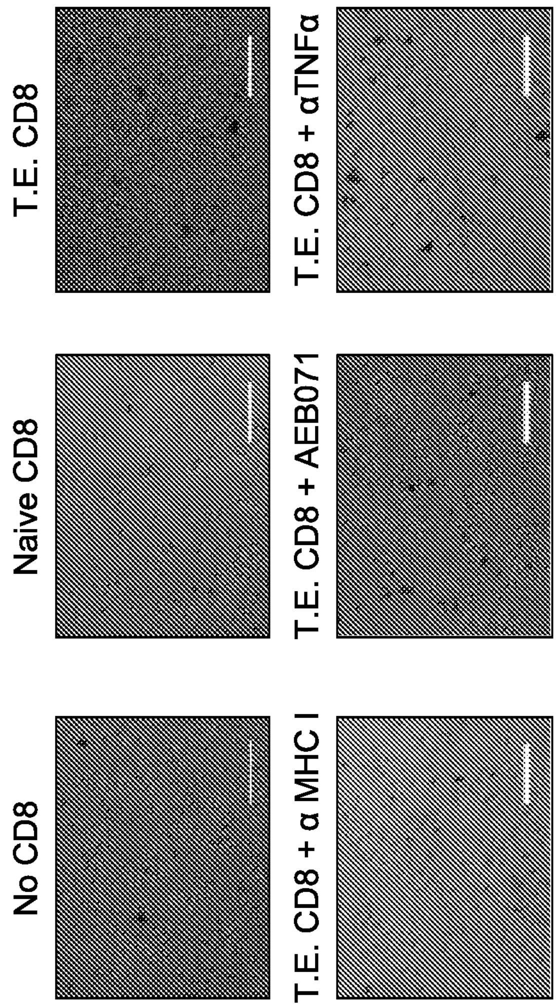
Figure 15E:
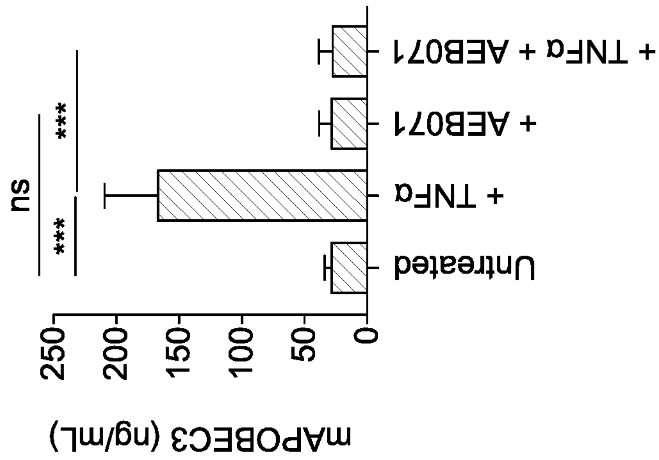
Figure 15D:
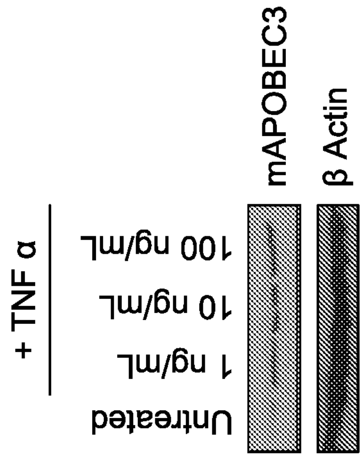
Figure 15C:
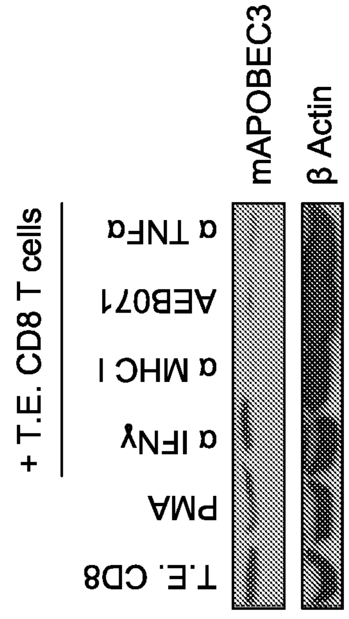
Figure 16C:
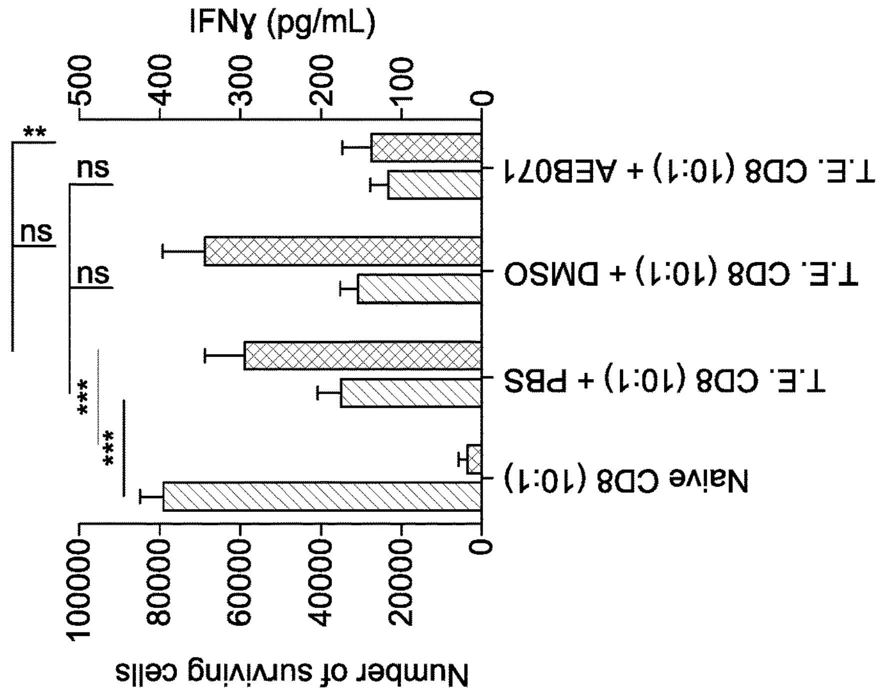
Figure 16B:
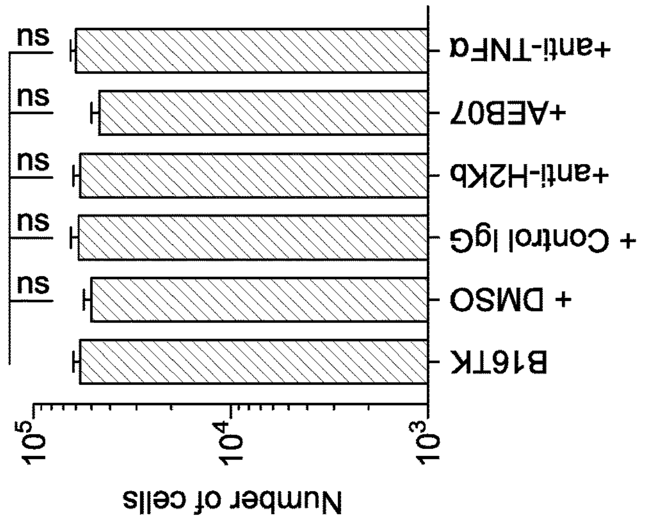
Figure 16A:
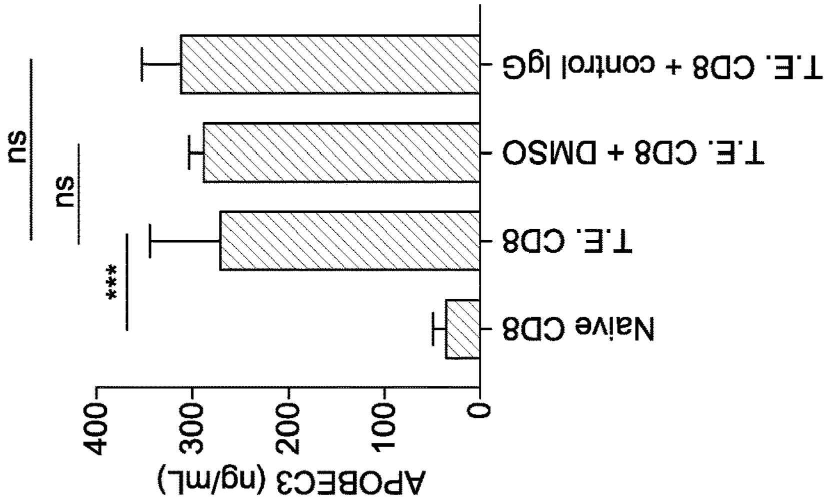

It was also confirmed that a low E:T ratio of tumor antigen specific T cells to tumor cells induced mAPOBEC3 not only in the B16 cell line but also in both the GL261 glioma line (FIG. 14A) and the lung carcinoma LLC line (FIG. 14B). Taken together, these data show that there is a threshold where suboptimal T cell activation and limited effector function induces APOBEC3 upregulation in tumor cells.

mAPOBEC3 induction and tumor cell outgrowth from GCV and T cell therapy was dependent on MHC class I recognition of tumor cells, TNFα secretion, and activation of PKC signaling, as antibody blockade of H-2 Kb, TNFα, or pharmacologic inhibition of PKC by AEB071 ablated the effect (FIGS. 15A, B). In contrast, an IFNγ blocking antibody had no significant effect on tumor cell mAPOBEC3 expression following CD8 T cell co-culture (FIG. 15C). mAPOBEC3 induction in B16TK cells was not affected by the DMSO solvent used to dilute the AEB071 drug or by the IgG control antibody (FIG. 16A). None of the treatments in FIG. 15A significantly inhibited the growth of B16TK cells alone (FIG. 16B). Consistent with a role for TNFα in T cell mediated mAPOBEC3 induction in tumor cells, exogenous TNFα was sufficient to induce mAPOBEC3 (FIGS. 15D and E), an effect which was almost completely inhibited by AEB071 action upon the tumor cells themselves (FIG. 15E). Although the cytotoxicity of the T.E. CD8 T cells was not significantly altered in the presence of AEB071 compared to PBS, the levels of IFNγ were significantly decreased in the presence of AEB071 (FIG. 16C). Therefore, the attenuated induction of mAPOBEC3 seen in the presence of T.E. CD8 T cells and AEB071 in FIG. 15A may indeed be the result of reduced induction of APOBEC3 in the tumor cells through inhibition of PKC signaling (FIG. 15E), and/or the result of partial inhibition of CD8 T cell function by AEB071.

The CD8 T Cell Induced Mutator Activity is Dependent on APOBEC3

Figure 17A:
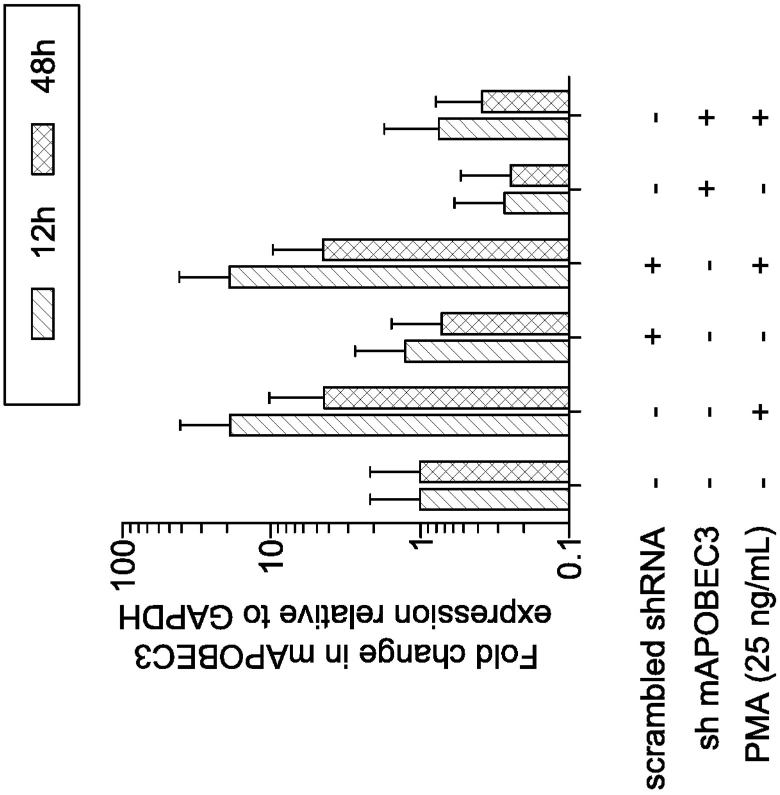
Figures 17B, 17C, 17D:
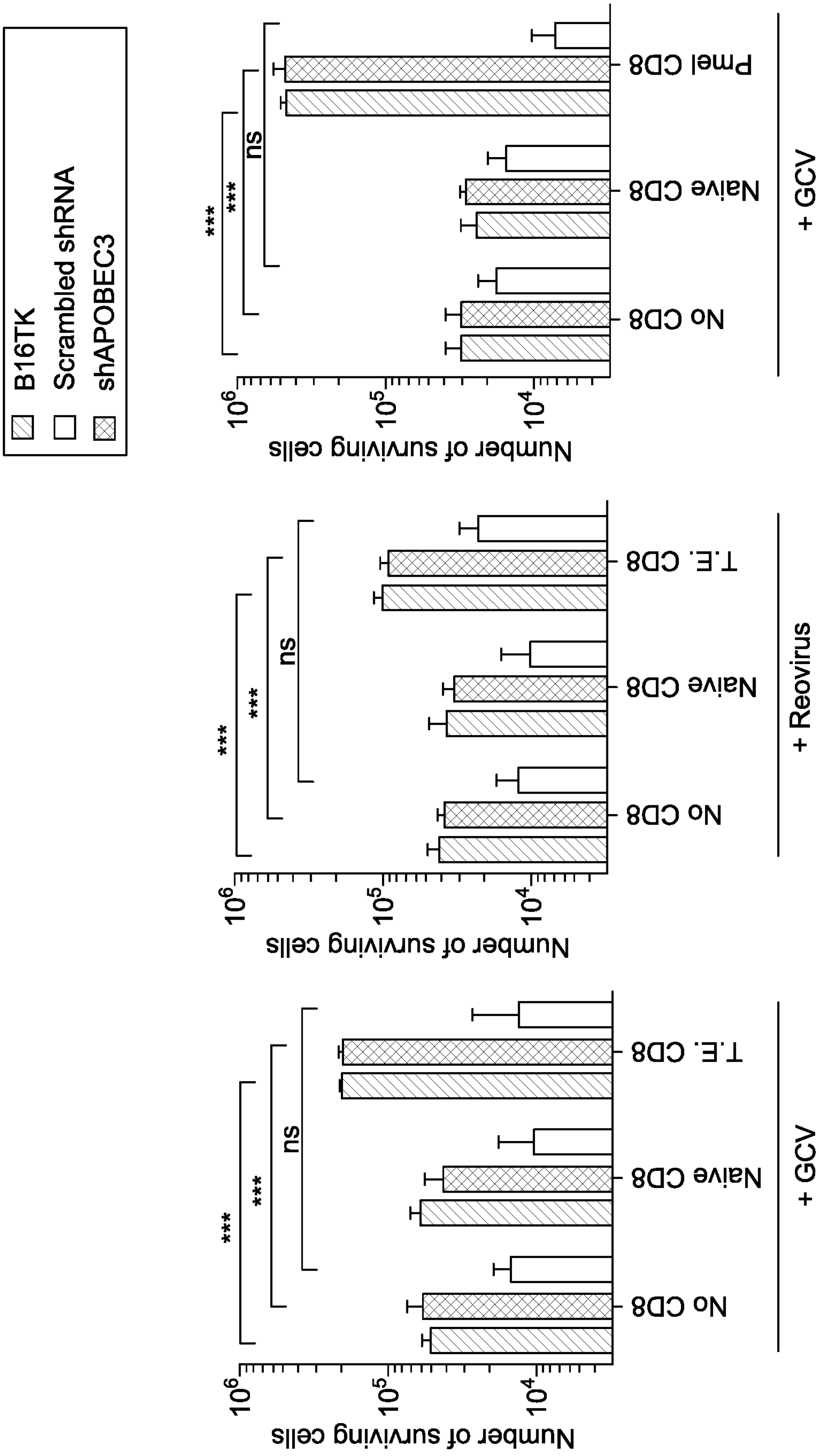
Figure 17E:
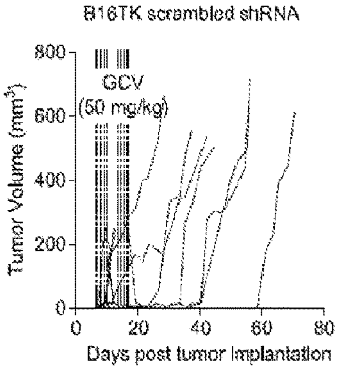
Figure 18B:
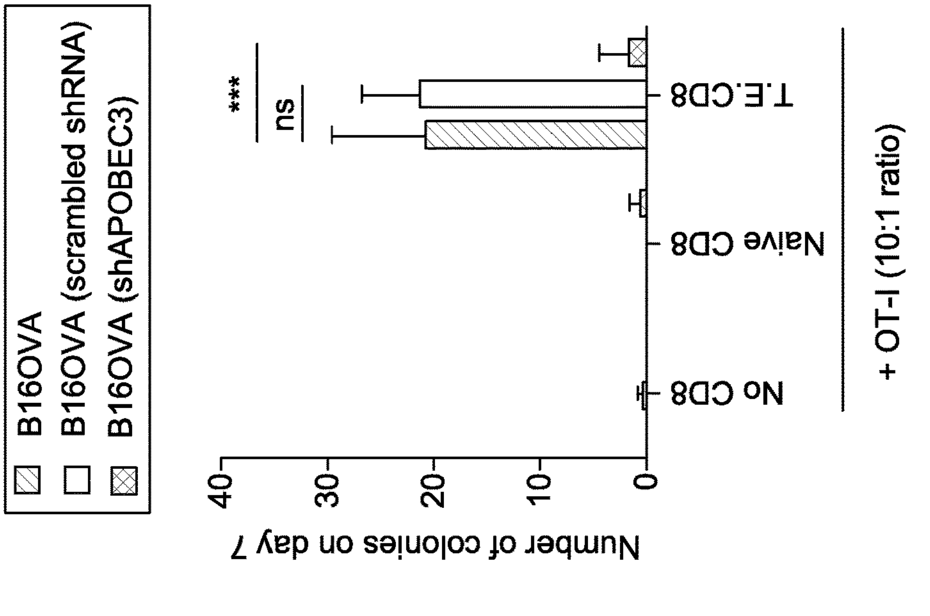
Figure 18A:
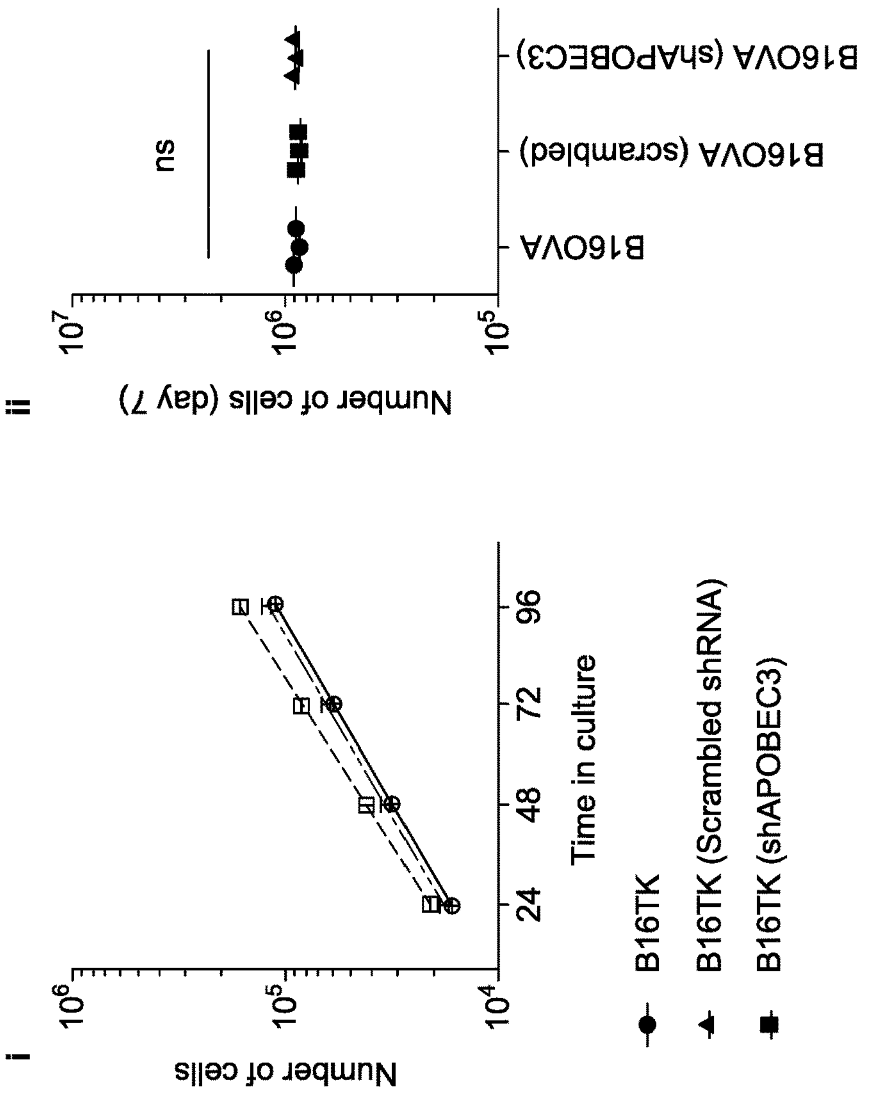

To confirm that mAPOBEC3 was required for the outgrowth of escape variants in this model, a stable B16TK cell line was generated expressing 4 unique 29mer shRNA constructs targeting mAPOBEC3 as well as a stable B16TK cell line with a single scrambled shRNA construct. mAPOBEC3 expression was significantly reduced in B16TK shRNA mAPOBEC3 cells, both at basal levels, and upon induction with PMA (FIG. 17A). In cultures treated with no CD8 T cells, or with naïve CD8 T cells, fewer B16TK sh mAPOBEC3 cells survived either GCV or reovirus treatments compared to parental B16TK or B16TK (scrambled shRNA) cells (FIGS. 17B & C). A statistically significant increase was not observed in the number of surviving B16TK sh mAPOBEC3 cells treated with GCV or reovirus when cells were co-cultured with T.E. CD8 T cells according the schedule in FIG. 12A (FIGS. 17B & C). B16TK parental or B16TK scrambled shRNA cells treated with GCV and co-cultured with T.E. CD8 exhibited the pattern of enhanced escape, in contrast to co-culture with naïve CD8 T cells. These results were recapitulated with reovirus infection, where more treatment resistant clones arose from parental B16TK and B16TK cells with scrambled shRNA than from B16TK sh mAPOBEC3 cells co-cultured with T.E. CD8 T cells (FIG. 17C). This same pattern of escape that was prevented with shRNA to mAPOBEC3 was also seen when B16TK cells were cocultured with activated Pmel T cells cultured in the presence of GCV (FIG. 17D). The three B16TK, B16TK sh mAPOBEC3 and B16TK scrambled shRNA cell lines grew at similar rates in vitro (FIG. 18A), therefore confirming that these results were not attributable to different rates of cell growth. In addition, more treatment-resistant clones could be isolated from parental B16OVA and from B16OVA cells with scrambled shRNA, than from B16OVA sh mAPOBEC3 cells co-cultured with OT-I CD8 T cells (FIG. 18B).

Figure 17F:
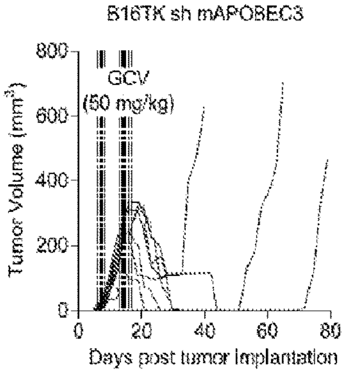
Figure 18C:
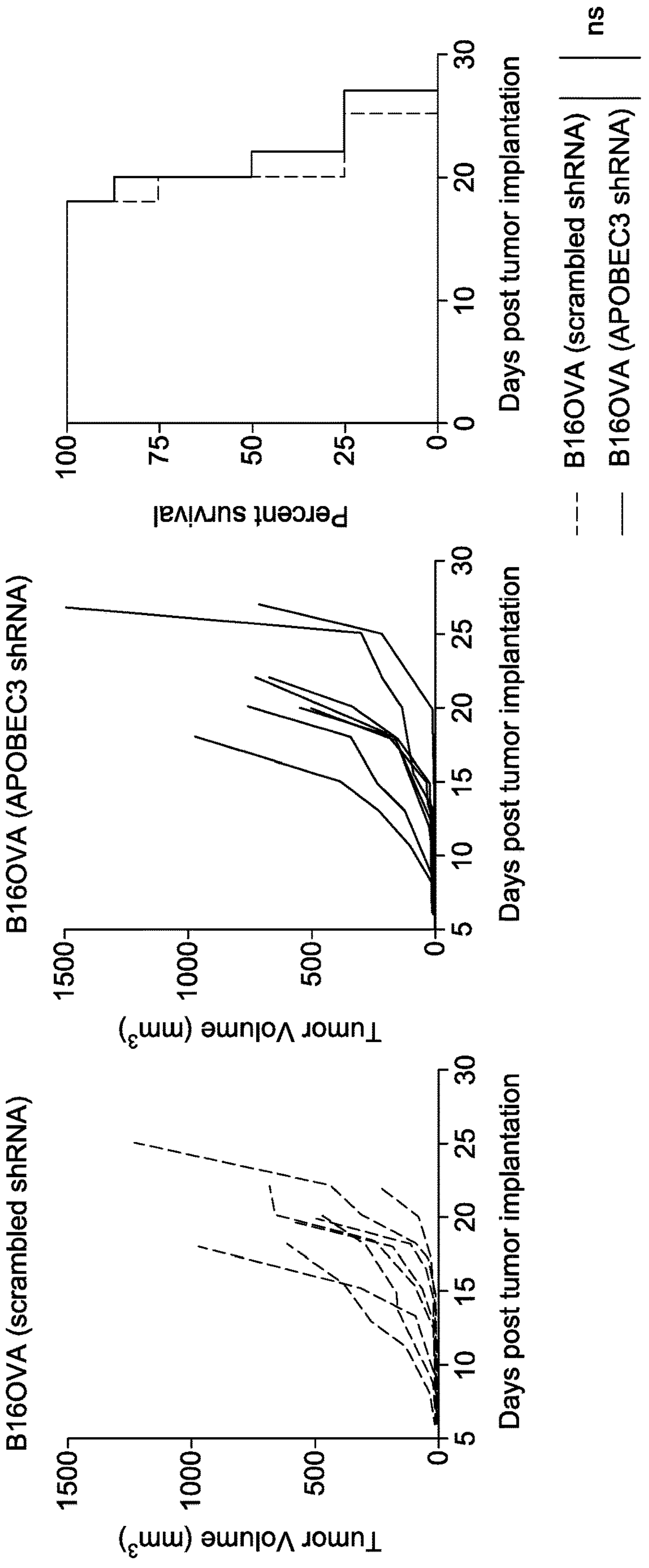

These results were validated in vivo where B16TK cells transduced with the scrambled shRNA or the mAPOBEC3-targeting shRNA were implanted subcutaneously and treated with a suboptimal course of GCV. While B16TK (scrambled shRNA) tumors all eventually escaped therapy (0/7 long term survivors) (FIG. 17E), recurrence was delayed, or did not occur, in B16TK tumors transduced with mAPOBEC3 shRNA (4/7 long term survivors) (FIG. 17F). These results could not be attributed to different growth rates of the tumors, as untreated tumors which expressed either scrambled shRNA or sh mAPOBEC3 grew at equivalent rates (FIG. 18C). This confirms that mAPOBEC3 expression after sub-optimal therapies can contribute to the generation of treatment-resistant clones in vivo.

Figure 17G:
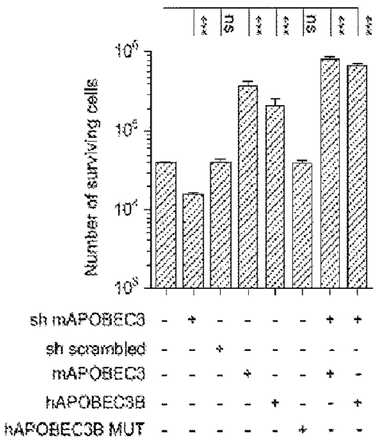
Figure 17H:
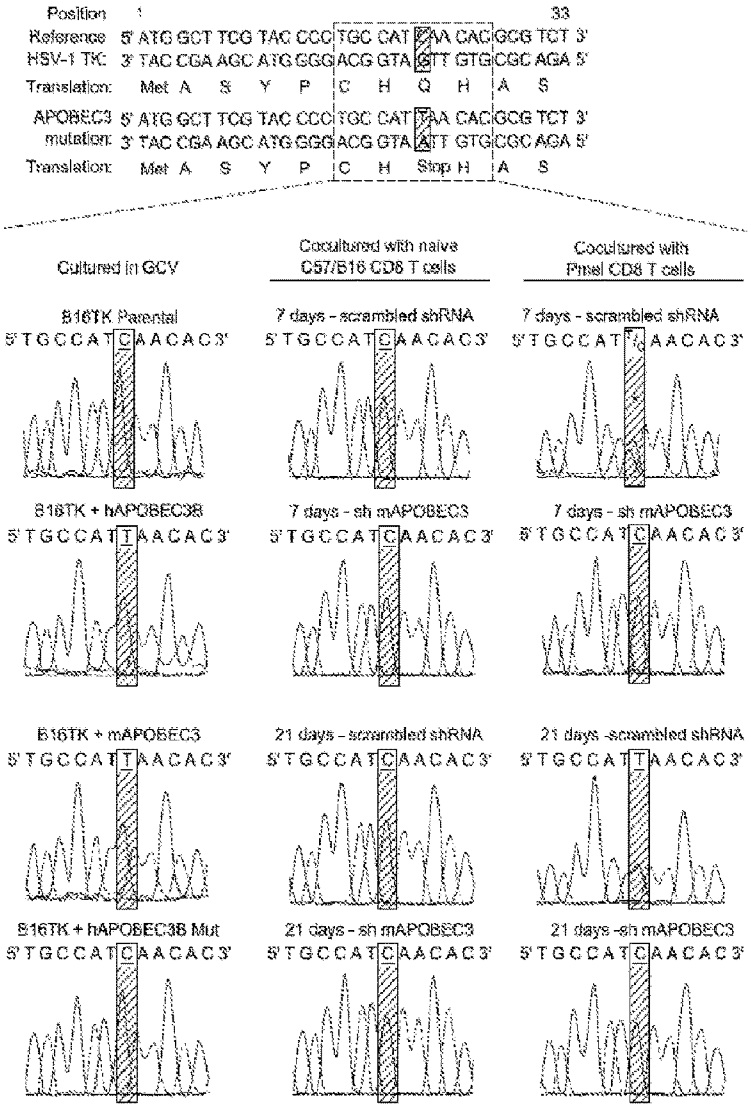
Figure 19A:
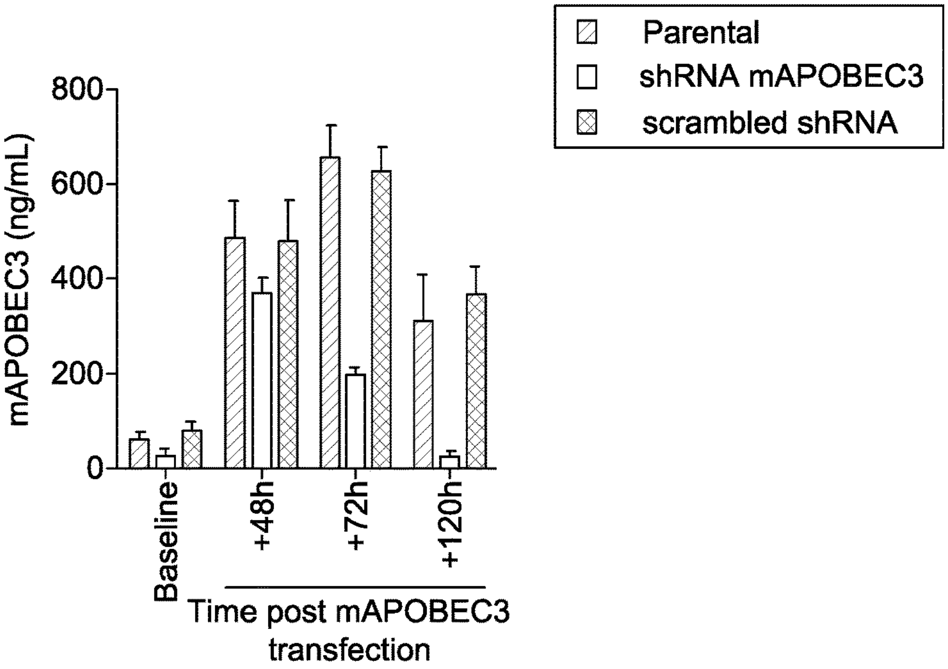

As the knockdown of mAPOBEC3 significantly reduced the ability of B16TK cells to escape GCV treatment (FIG. 17B-F), it was evaluated how the overexpression of mAPOBEC3 could promote therapeutic escape in the previously described 21-day treatment cycle (FIG. 17G). The T cell mediated induction of a TCA-TTA mutation in the OVA gene which allowed escape from OT-I T cell therapy (FIG. 12) suggested that mAPOBEC3 may have overlapping functionality and specificity with its human APOBEC3B counterpart, and therefore we additionally overexpressed hAPOBEC3B in B16TK cells. It was observed that overexpression of either mAPOBEC3 or hAPOBEC3B both promoted the outgrowth of treatment resistant clones compared to unmodified B16TK cells. Moreover, overexpressed mAPOBEC3 or hAPOBEC3B was able to rescue the phenotype induced by shRNA knockdown of APOBEC3 in B16TK cells treated with GCV. In contrast, overexpression of a catalytically inactive form of the protein, hAPOBEC3B MUT, did not promote resistance. Although the anti-mAPOBEC3 shRNA expressed in the B16TK (shRNA mAPOBEC3) cells was able to target the pCMV-APOBEC3 plasmid used for over-expression of mAPOBEC3 in these experiments, it was unable to prevent its induction, especially at early time points (FIG. 19A). Parental B16TK cells transfected with the pCMV-APOBEC3 plasmid over-expressed mAPOBEC3 which peaked at >655 ng/ml by 72 hours post transfection and fell to ~311 ng/ml by 120 hours post transfection. In contrast, B16TK (shRNA mAPOBEC3) cells, transfected under identical conditions, over-expressed mAPOBEC3 to a peak of only ~370 ng/ml at 48 hours and fell to undetectable levels by 120 hours. Taken together, these data confirm that mouse APOBEC3 activity, as shown to be induced through T cell derived TNFα (FIG. 13), can explain the induction of resistance to GCV killing observed.

Figure 19B:
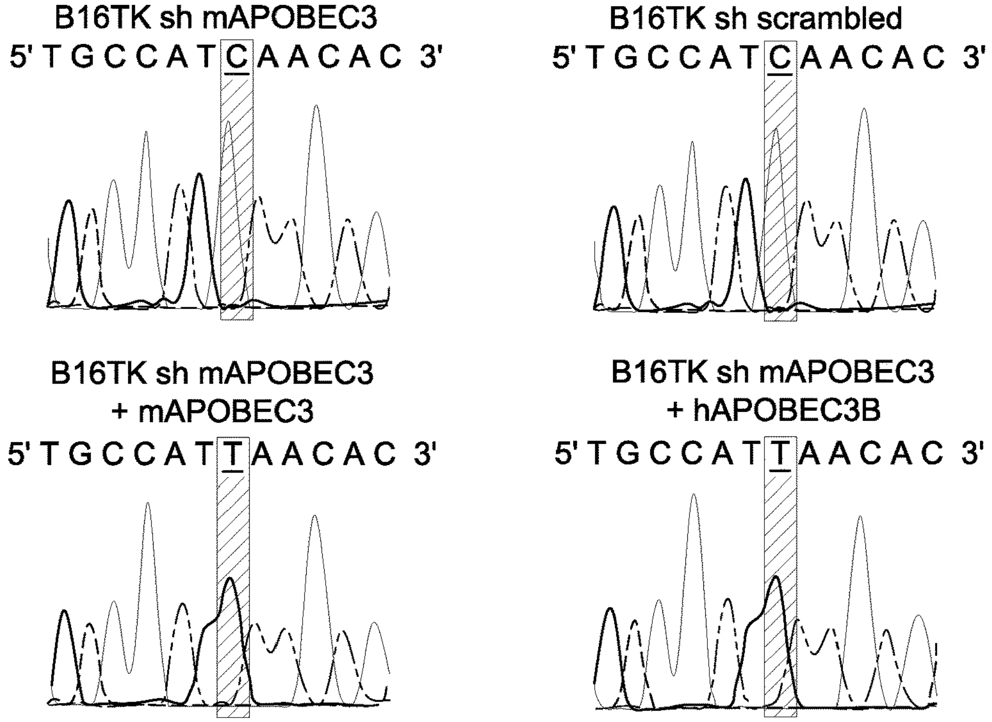
Figure 19C:
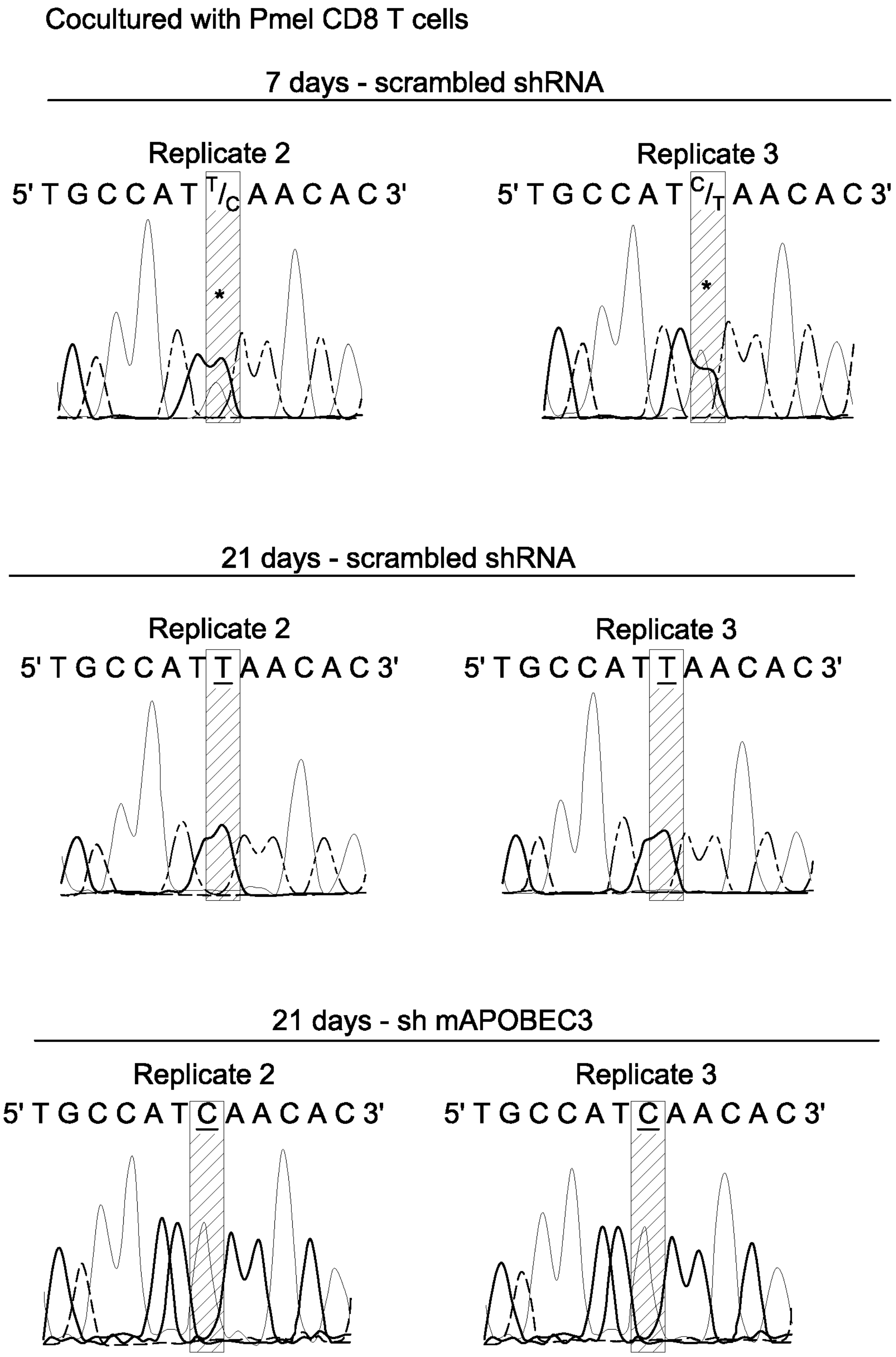

The mechanism of GCV escape was investigated by sequencing the bulk populations from each condition in FIGS. 17 D and G. B16TK parental cells that escaped GCV treatment in vitro retained the wild type HSV-TK sequence, suggesting that failure to eradicate these cells was not due to mutation of the therapeutic gene (FIG. 17H). In contrast, B16TK cells engineered to overexpress either hAPOBEC3B, or mAPOBEC3, both selected populations of cells in which the HSV-TK gene contained an AT$\overline{\text{C}}$A-AT$\overline{\text{T}}$A mutation (FIG. 17H). This mutation introduced a ST$\overline{\text{O}}$P codon in the first 8 amino acids of the protein, thereby preventing expression of functional HSV-TK protein to maintain susceptibility to GCV therapy. This mutation was not observed in the B16TK sh mAPOBEC3 cells, but the shRNA knockdown could be overwhelmed by the plasmid overexpression of mAPOBEC3 (FIG. 19B). Whether the CD8 T cell-mediated mutator phenotype, which we have shown to be at least partly dependent upon APOBEC3 activity, was also associated with this mAPOBEC3-driven mutation signature was also investigated by sequencing surviving cells from FIG. 17D. B16TK cells which survived the 21 day GCV selection regimen during co-culture with either no CD8+ T cells, or with naïve CD8+ T cells from C57Bl/6 mice, showed no evidence of the APOBEC3-driven AT$\overline{\text{C}}$A-AT$\overline{\text{T}}$A mutation in the HSV-TK gene which induced a ST$\overline{\text{O}}$P codon, at either an early time point (7 days) or late time point (21 days) in the selection process (FIG. 17H), indicating that resistance to GCV in these cells was not associated with this particular mechanism of escape. GCV-resistant B16TK cell populations selected in the presence of tumor-specific CD8 T cells consisted of a mixed population of HSV-TK wild type (AT$\underline{\text{C}}$A) and HSV-TK-mutated (AT$\underline{\text{T}}$A) cells 7 days after co-application of both T cell and GCV selective pressure. Once this pool of potentially GCV-resistant cells had been generated, 2 further weeks of GCV therapy forced the evolution of a completely clonal population of B16TK ESC cells, at least with respect to the HSV-TK[22] gene mutation. In contrast, knockdown of mAPOBEC3 prevented both the induction of the AT$\underline{\text{C}}$A-AT$\underline{\text{T}}$A mutation within 7 days of co-culture and selection/fixation of the mutation by day 21. These results were confirmed in two replicate experiments (FIG. 19C). Taken together, these results show that suboptimal T cell therapy can promote the emergence of resistance to a co-applied frontline therapy through an APOBEC-driven mutational mechanism. These data provide strong evidence that mAPOBEC3 has overlapping mutational specificity with hAPOBEC3B and provide a direct mechanism by which resistance to GCV therapy can be acquired.

hAPOBEC3B Overexpression Drives Tumor Escape

Figure 20A:
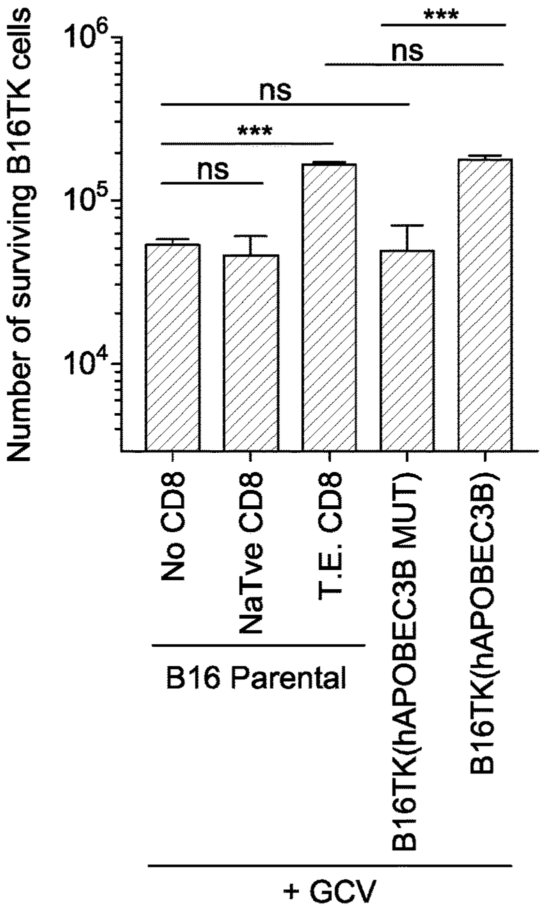
Figure 20B:
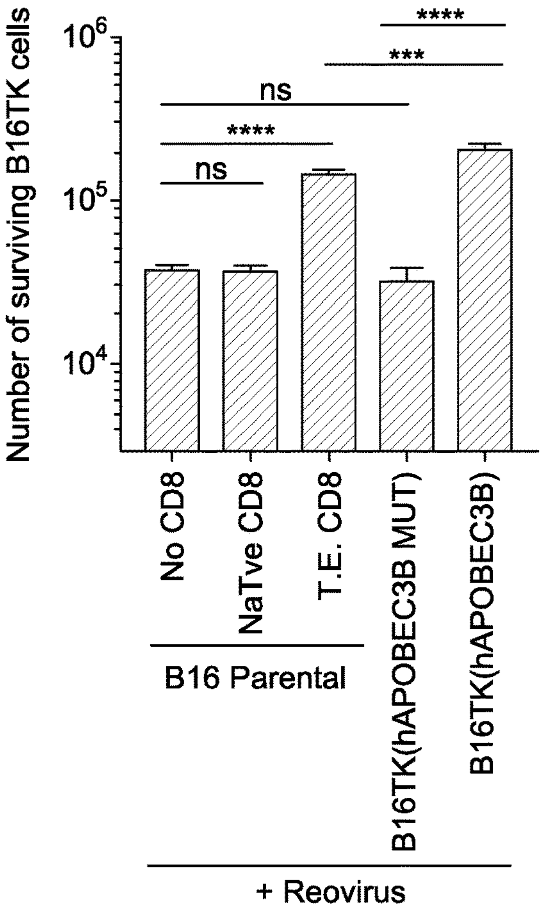

The role of APOBEC3B in the acquisition of therapeutic resistance was evaluated using the retroviral overexpression system of human APOBEC3B used in FIG. 17F. B16 tumor cell lines were engineered to overexpress hAPOBEC3B, or a catalytically inactive form of the protein hAPOBEC3B MUT. 48 hours post transduction, bulk populations of cells were selected in hygromycin for 2 weeks and used for experiments. It was observed that over-expression of hAPOBEC3B is toxic in that elevated levels of hAPOBEC3B are seen within 72 hours post transfection/infection and then return to similar levels to that seen in parental unmodified cells. In other cells, overexpression of hAPOBEC3B may not reach the threshold, or mutations may not be induced in critical genes, allowing those cells to survive carrying the hAPOBEC3B induced mutations. The increased frequency of GCV resistant tumor cell outgrowth that had previously been seen when B16TK cells were co-cultured with T.E. CD8 T cells was recapitulated by the overexpression of hAPOBEC3B in B16TK cells (FIG. 20A). In contrast, an increase was not observe in the number of treatment-resistant cells derived from B16TK cells expressing a catalytically inactive mutant hAPOBEC3B. In parallel, hAPOBEC3B overexpression in B16TK cells increased the rate of outgrowth following reovirus infection (FIG. 20B). Together, these experiments demonstrate that hAPOBEC3B function is sufficient to support therapeutic escape.

Figure 18D:
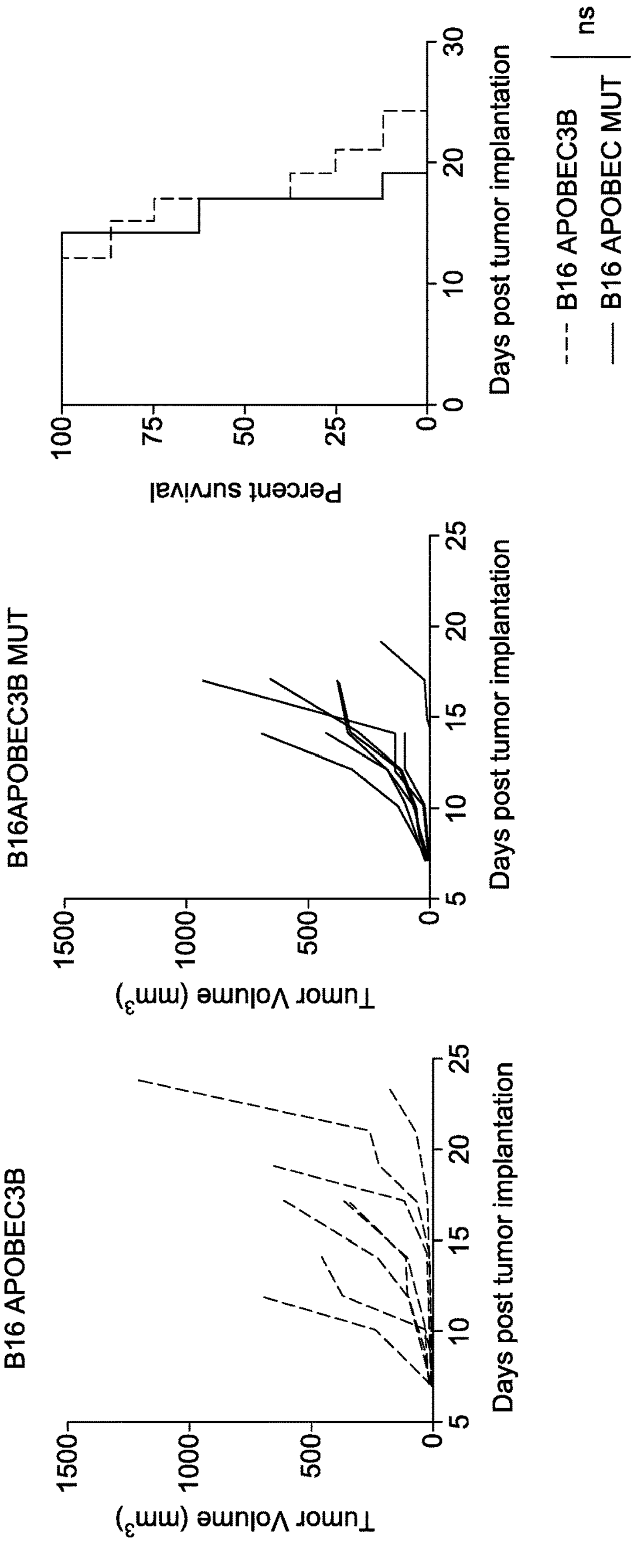
Figure 20C:
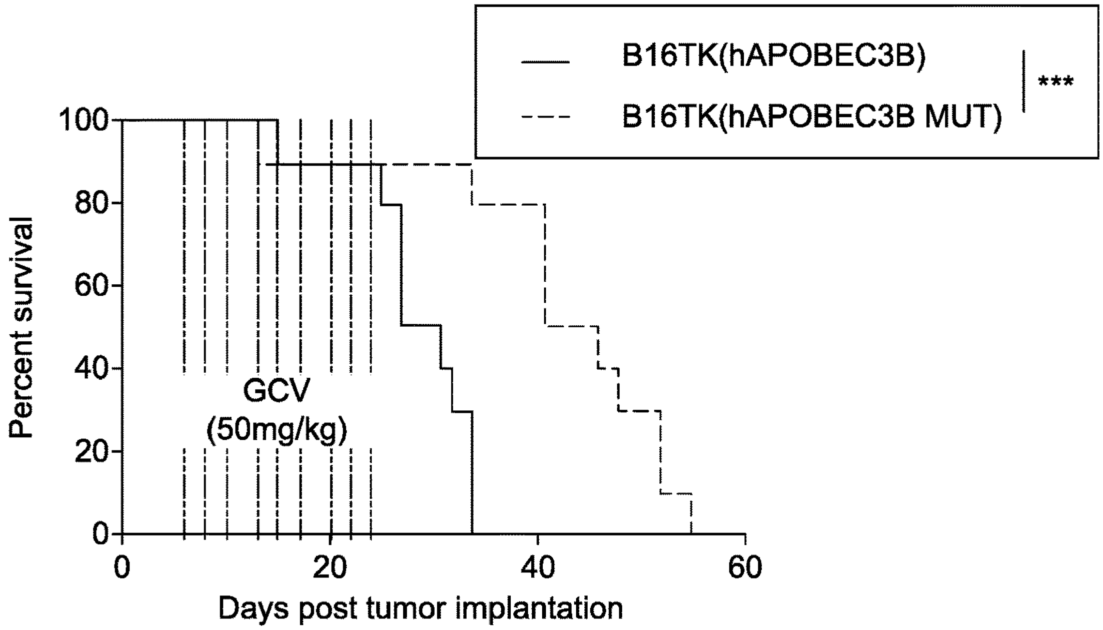
Figure 20F:
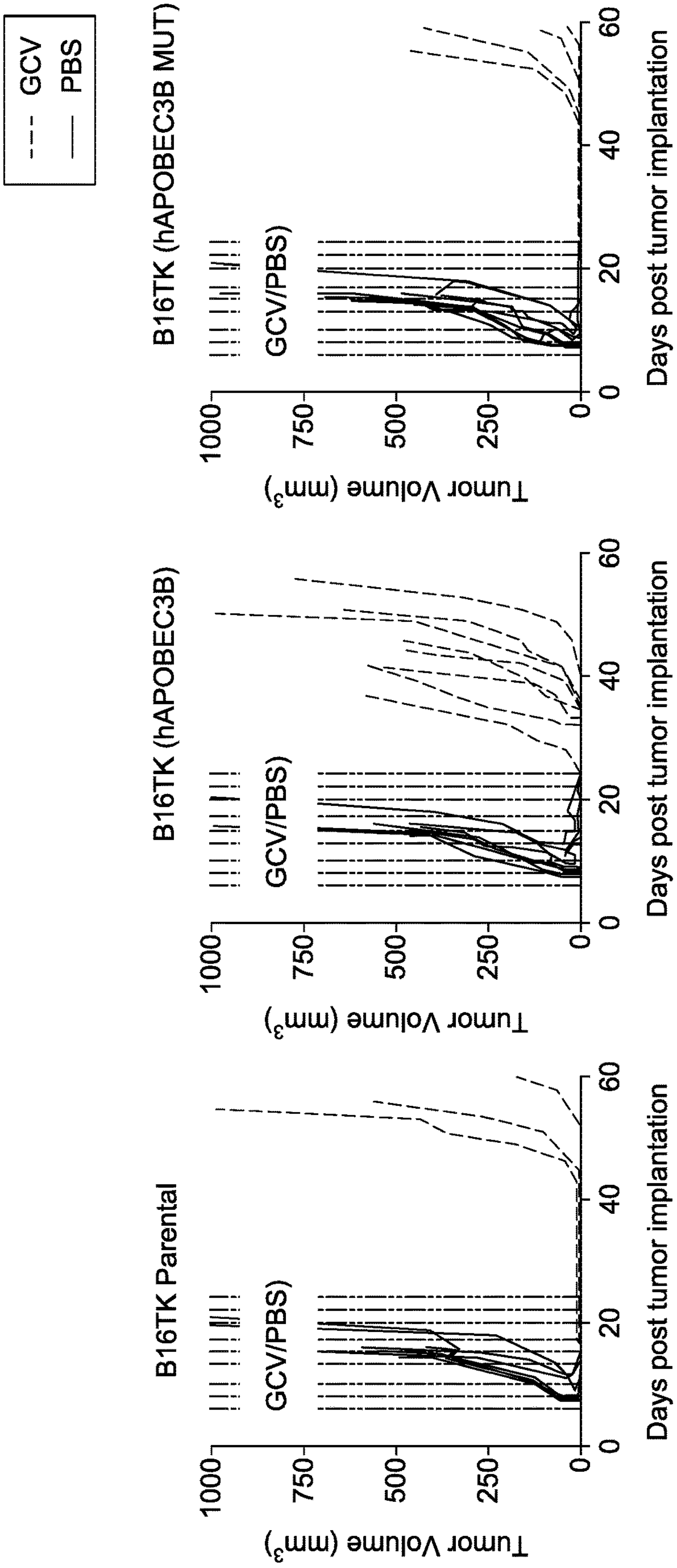

Finally, when implanted intracranially in a model of metastatic melanoma, B16TK-hAPOBEC3B tumors grew significantly more quickly following GCV treatment compared to B16TK-hAPOBEC3B MUT tumors (FIG. 20C). These results could not be attributed to different growth rates of the tumors, as untreated tumors which overexpressed either hAPOBEC3B or mutated APOBEC3B grew at equivalent rates (FIG. 18D). Western blot analysis of intracranial tumors recovered from mice showed that 4/4 B16TK-hAPOBEC3B MUT tumors continued to express the HSV TK protein, despite eventually failing therapy, whereas 0/4 B16TK hAPOBEC3B tumors continued to express HSV TK protein (FIG. 20D). Sequencing of the HSV TK gene identified a C to T mutation in the coding region at position 22 within the characteristic hAPOBEC3B TCA motif in all four B16TK hAPOBEC3B tumors that was not observed in the parental B16TK cell line (FIG. 20E). This mutation converted a (CAA) glutamine to a (TAA) stop codon within the first 10 amino acids of the protein and was the same mutation observed in vitro (FIG. 17F). None of the B16TK-APOBEC3B MUT tumors contained this mutation, or any detectable characteristic APOBEC3 C to T mutation within the TCW motif in the HSV TK gene. Finally, B16TK-hAPOBEC3B subcutaneous tumors also grew significantly more quickly following GCV treatment compared to parental B16TK or B16TK-hAPOBEC3B MUT tumors, even though untreated tumors grew at equivalent rates (FIG. 20F). These data strongly support the hypothesis that hAPOBEC3B expression drives a mutator phenotype in tumor cells which allows for selection of a tumor cell clone that can resist treatment and emerge in vivo despite powerful treatment pressure.

Materials and Methods

Cell Lines

B16 murine melanoma cells were obtained from the ATCC prior to being modified with the relevant transgenes. Cell lines were authenticated by morphology, growth characteristics, PCR for melanoma specific gene expression (gp100, TYRP-1 and TYRP-2) and biologic behavior, tested mycoplasma-free and frozen. Cells were cultured less than 3 months after thawing. The B16OVA cell line was derived from a B16.F1 clone transfected with a pcDNA3.1ova plasmid described elsewhere (see, e.g., Kaluza et al., *Hum Gene Ther.* 131:844-854 (2012); and Kaluza et al., *Int J Cancer.* 131(4):844-54 (2012)). B16OVA cells were grown in DMEM (HyClone, Logan, Utah, USA)+10% FBS (Life Technologies)+5 mg/mL G418 (Mediatech, Manassas, Va., USA) until challenge. GL2610VA was obtained by transfection of parental GL261 cells with pcDNA3.1 OVA. LLCOVA was obtained by transfection of parental LLC cells with pcDNA3.1 OVA. B16TK cells were derived from a B16.F1 clone transfected with a plasmid expressing the Herpes Simplex Virus thymidine kinase (HSV-1 TK) as described elsewhere (see, e.g., Boichard et al., *Oncoimmunology.* 6(3):e1284719 (2017)). Following stable selection in 1.25 μg/mL puromycin, these cells were shown to be sensitive to Ganciclovir (Cymevene) at 5 μg/ml. Cells were tested for *mycoplasma* using the MycoAlert *Mycoplasma* Detection Kit (Lonza Rockland, Inc. ME, USA).

Mice 6-8 week old female C57BL/6 mice were purchased from Jackson Laboratories (Bar Harbor, Me.). The OT-I mouse strain is on a C57Bl/6 background and expresses a transgenic T cell receptor Vα2/Vβ5 specific for the SIINFEKL (SEQ ID NO:9) peptide of ovalbumin in the context of MHC class I, H-2 Kb. The Pmel mouse strain is on a C57Bl/6 background and express a transgenic T cell receptor Vα1/Vβ13 that recognizes amino acids 25-33 of gp100 presented by H2-db.

Viruses

Wild-type Reovirus type 3 (Dearing strain) was obtained from Oncolytics Biotech (Calgary, AB, Canada) and stock titers were measured by plaque assay on L929 cells.

Viability Assays

B16TK cells were seeded in 96 well plates in triplicate and treated with reovirus (MOI 0.1) or with GCV (Cymevene) at 5 μg/ml. Cell titer blue (Promega, Madison, Wis.) was added to wells at 10% v/v and fluorescence was measured after approximately 4 hours incubation ($560_{Ex}/590_{Em}$). Relative viability of experimental conditions was normalized to untreated cells.

CD8 T Cell Preparation

Spleens were immediately excised from euthanized C57Bl/6, OT-I mice and dissociated in vitro to achieve single-cell suspensions. Red blood cells were lysed with ACK lysis buffer. CD8 T cells were prepared using the CD8α T Cell Isolation kit (Miltenyi, Auburn, CA) and co-cultured with target tumor cells at various effector to target ratios as described in the text. Supernatants were assayed for IFNγ by ELISA as directed in the manufacturer's instructions (Mouse IFN-γ ELISA Kit, OptEIA, BD Biosciences, San Diego, CA).

In Vitro T Cell Activation

OT-I or Pmel T cells were activated in IMDM (Gibco, Grand Island, N.Y., USA)+5% FBS+1% Pen/Strep+40 μM 2-ME. Media was supplemented with the SIINFEKL (SEQ ID NO:9) or KVPRNQDWL (SEQ ID NO:10) peptides respectively at 1 μg/mL and human IL2 at 50 U/mL. Cells were used for in vitro assays following 4 days of activation.

Generation of Tumor Experienced B16TK (T.E.) CD8 T Cells

CD8 T cells were prepared as described above from C57BL/6 mice that had been cured of subcutaneous B16TK tumors following three weekly courses of GCV (50 mg/kg on days 5-9, 12-16, and 19-23). Cells were harvested between 60 and 80 days post tumor implantation.

In Vitro Selection of Therapy Resistant Populations

B16TK or B16OVA cells were plated in triplicate wells in the presence of GCV (Cymevene) at 5 μg/ml, reovirus (MOI 0.1) or 4-day in vitro activated OT-I CD8T cells or T.E. CD8 T cells (E:T ratio of 5:1) for 7 days in Iscove's Modified Dulbecco's Medium (IMDM; Gibco, Grand Island, NY)+5% FBS+1% Pen-Strep+40 μL β-mercaptoethanol. Wells were washed 3 times with PBS and cultured in normal medium for a further 7 days. Surviving cells were then cultured again in the presence of PBS, GCV, reovirus (MOI 0.1) or 4-day in vitro activated OT-I CD8 T cells or T.E. CD8 T cells (various effector to target ratios) for 7 days.

These co-culture systems were also performed with the anti-H-2 Kb antibody (AF6-88.5; 0.5 μg/mL) (Biolegend, San Diego, CA), the inhibitor of PKC signaling (AEB071; 10 μM) (MedChemExpress, Monmouth Junction, NJ) or the anti-TNFα antibody (AF-410-NA; 0.5 μg/ml) (R&D Systems; Minneapolis, MN) or the anti-IFNγ antibody (MAB485; 0.5 μg/ml) (R&D Systems; Minneapolis, MN).

Quantitative RT-PCR and Sequencing

RNA was prepared with the QIAGEN-RNeasy-MiniKit (Qiagen, Valencia, CA). 1 μg total RNA was reverse-transcribed in a 20 μl volume using oligo-(dT) primers using the First Strand cDNA Synthesis Kit (Roche, Indianapolis, IN). A cDNA equivalent of 1 ng RNA was amplified by PCR with gene-specific primers using GAPDH as loading control (mgapdh sense: TCATGACCACAGTCCATGCC (SEQ ID NO:5); mgapdh antisense: TCAGCTCTGGGATGACCTTG (SEQ ID NO:6); APOBEC3 sense: ATGGGACCATTCTGTCTGGGA (SEQ ID NO:7); APOBEC3 antisense:

TCAAGACACGGGGGTCCAAG (SEQ ID NO:8)). qRT-PCR was carried out using a LightCycler480 SYBRGreenI Master kit and a LightCycler480 instrument (Roche) according to the manufacturer's instructions. The $\Delta\Delta C_T$ method was used to calculate the fold change in expression level of APOBEC3 and GAPDH as an endogenous control for all treated samples relative to an untreated calibrator sample.

The OVA transgene was sequenced using the following primers:

Sense: ATGGGCTCCATCGGCGCAGC (SEQ ID NO:11) and antisense: CCGTCTACACAAAGGGGAATT (SEQ ID NO:12) and aligned to the reference sequence CAA23682.1. The HSV TK transgene was sequenced using the following primers: CACGCA-GATGCAGTCGGGGCGGCG (SEQ ID NO:13) (Downstream of the EcoR1 site in the 5'UTR), CTGGTGGCCCTGGGTTCGCGCGA (SEQ ID NO:14), GCGTTCGTGGCCCTCATCCC (SEQ ID NO:15), GCCTGGGCCTTGGACGTCTTGG (SEQ ID NO:16), and AGGGCGCAACGCCGTACGTCG (SEQ ID NO:17) and aligned to the reference sequence AB009254.2.

APOBEC3 and HSV TK Protein Quantification

Murine APOBEC3 was measured by western blotting with a rabbit polyclonal (PA511430, Thermo Fisher) or a rabbit monoclonal anti-human APOBEC3B (184990, Abcam, San Francisco, CA) which react with both human APOBEC3B and murine APOBEC3 (Thermo Fisher) or by ELISA according to the manufacturer's instructions (Antibody Research Corporation, St Charles, MO). B16TK cells were treated with recombinant murine TNFα (R&D Systems, Minneapolis, MN). HSV TK protein was detected by western blotting tumor cell lysates with a goat polyclonal antibody (28038; Santa Cruz, Dallas, TX). β-actin was detected using an HRP conjugated mouse monoclonal antibody (clone AC-15; Sigma, St. Louis, MO).

APOBEC3 Knockdown and Overexpression.

Mouse unique 29mer shRNA retroviral constructs (Origene Technologies, Rockville, MD) were tested individually, or as a combination, for their ability to reduce expression of murine APOBEC3 in B16 cells compared to a single scrambled shRNA encoding retroviral construct. Optimal knockdown for periods of more than two weeks in culture was achieved using all four constructs pre-packaged as retroviral particles in the GP+E86 ecotropic packaging cell line and used to infect B16 cells at an MOI of ~10 per retroviral construct. In addition, a single scrambled negative control non-effective shRNA cassette was similarly packaged and used to infect B16TK cells to generate B16TK (scrambled shRNA) cells.

B16TK cells were infected with a retroviral vector encoding either full length functional APOBEC3B or a mutated, non-functional form of APOBEC3B as a negative control. Infected populations were selected for 7 days in hygromycin to generate B16TK (APOBEC3B) or B16TK (APOBEC3B MUT) cell lines and used for experiments as described. In populations of B16TK (APOBEC3B) cells selected for more than 7-10 days in hygromycin expression of APOBEC3B returned to basal levels associated with the toxicity of prolonged APOBEC3B expression. Murine APOBEC3 (Accession: BC003314) was expressed from the pCMV-SPORT6 plasmid obtained from Dharmacon, Lafayette, CO)

In Vivo Experiments

All in vivo studies were approved by the Institutional Animal Care and Use Committee at Mayo Clinic. Mice were challenged subcutaneously with $2\times10^5$ B16TK melanoma cells, in 100 μL PBS (HyClone, Logan, Utah, USA) or with $1\times10^4$ cells in 2 uL intracranially into the frontal lobe as described elsewhere (see, e.g., Carlson et al., *Curr Protoc Pharmacol*. Chapter 14:Unit 14-16 (2011)). Subcutaneous tumors were treated with a two or three-week course of GCV (50 mg/kg) administered IP daily. Tumors were measured 3 times per week, and mice were euthanized when tumors reached 1.0 cm in diameter. Intracranial tumors were treated with a three-week courses of GCV (50 mg/kg) administered IP daily. Mice were sacrificed upon emergence of neurological symptoms or weight loss.

Statistics

Survival curves were analyzed by the Log-Rank test. Student's T tests, one-way ANOVA and two-way ANOVA were applied for in vitro assays as appropriate. Statistical significance was set at $p \leq 0.05$ for all experiments.

Summary

These results suggest that the generation of weak affinity and/or low frequency, sub-optimal T cell responses against TAAs may actively drive a mutator phenotype in tumors through APOBEC3 activity and promote the emergence of treatment resistant tumor populations. Hence, whenever potentially immunogenic frontline therapies are being administered to patients, it will be important to try to optimize the generation of potent CD8 T cell responses, with high frequencies of high affinity circulating anti-tumor T cells in order to reduce any T cell mediated induction of tumor escape and recurrence.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cancer, wherein said method comprises systemically administering a composition comprising an oncolytic virus to said mammal, thereby reducing the number of cancer cells within said mammal, wherein said oncolytic virus comprises nucleic acid encoding a short hairpin RNA (shRNA) that is composed of SEQ ID: 1, SEQ ID: 2, SEQ ID: 3, or SEQ ID: 4, wherein the short hairpin RNA can interfere with nucleic acid encoding a APOBEC3B polypeptide and reduce APOBEC3B polypeptide expression in the mammal.

2. The method of claim 1, wherein said mammal is a human.

3. The method of claim 1, where said cancer is selected from the group consisting of breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, and lymphoma.

4. The method of claim 1, wherein said oncolytic virus is selected from the group consisting of a vesicular stomatitis virus (VSV), a Maraba virus (MARAV), a herpes simplex virus (HSV), a vaccinia virus (VV), a measles virus (MV), and a poliovirus (PV).

5. The method of claim 1, wherein said composition comprises from about $10^3$ plaque-forming units (PFUs) to about $10^{13}$ PFUs of said oncolytic viruses.

6. The method of claim 1, wherein said composition comprises said oncolytic viruses at a multiplicity of infection (MOI) of from about 0.0000001 to about 10000.

7. A method for treating a mammal having cancer, wherein said method comprises systemically administering an oncolytic virus to said mammal, thereby reducing the number of cancer cells within said mammal, and systemically administering nucleic acid encoding a short hairpin RNA (shRNA) that is composed of SEQ ID: 1, SEQ ID: 2, SEQ ID: 3, or SEQ ID: 4, wherein the short hairpin RNA can interfere with nucleic acid encoding a APOBEC3B polypeptide and reduce APOBEC3B polypeptide expression in the mammal.

8. The method of claim 7, wherein said mammal is a human.

9. The method of claim 7, where said cancer is selected from the group consisting of breast cancer, brain cancer, prostate cancer, ovarian cancer, lung cancer, hepatocellular carcinoma, pancreatic cancer, kidney cancer, melanoma, bladder cancer, colorectal cancer, osteosarcoma, myeloma, leukemia, and lymphoma.

10. The method of claim 7, wherein said nucleic acid encoding said nucleic acid molecule is administered in a virus, and wherein said virus is selected from the group consisting of a retrovirus, a lentivirus, an adenoviruses, an adeno-associated virus, vesicular stomatitis virus (VSV), a Maraba virus (MARAV), a herpes simplex virus (HSV), a vaccinia virus (VV), a measles virus (MV), and a poliovirus (PV).

11. The method of claim 7, wherein said oncolytic virus is selected from the group consisting of a VSV, a HSV, a VV, an adenovirus, a MV, and a PV.

12. The method of claim 7, wherein said composition comprises from about $10^3$ PFUs to about $10^{13}$ PFUs of said oncolytic viruses.

13. The method of claim 7, wherein said composition comprises said oncolytic viruses at a MOI of from about 0.0000001 to about 10000.

* * * * *